(12) United States Patent
Packard et al.

(10) Patent No.: US 7,312,302 B2
(45) Date of Patent: *Dec. 25, 2007

(54) COMPOSITIONS FOR THE DETECTION OF ENZYME ACTIVITY IN BIOLOGICAL SAMPLES AND METHODS OF USE THEREOF

(75) Inventors: Beverly S. Packard, Potomac, MD (US); Akira Komoriya, Potomac, MD (US)

(73) Assignee: OncoImmunin, Inc., Gaithersburg, MD (US)

( * ) Notice: Subject to any disclaimer, the term of this patent is extended or adjusted under 35 U.S.C. 154(b) by 859 days.

This patent is subject to a terminal disclaimer.

(21) Appl. No.: 09/874,350

(22) Filed: Jun. 4, 2001

(65) Prior Publication Data

US 2004/0096926 A1 May 20, 2004

Related U.S. Application Data

(63) Continuation-in-part of application No. PCT/US00/24882, filed on Sep. 11, 2000, which is a continuation-in-part of application No. 09/394,019, filed on Sep. 10, 1999, now Pat. No. 6,936,687, which is a continuation-in-part of application No. PCT/US98/03000, filed on Feb. 20, 1998, which is a continuation-in-part of application No. 08/802,981, filed on Feb. 20, 1997, now Pat. No. 6,037,137.

(51) Int. Cl.
*C12Q 1/37* (2006.01)
*C07K 7/00* (2006.01)

(52) U.S. Cl. ............... 530/300; 530/324; 530/326; 514/2; 514/13; 435/23; 435/24; 435/7.72

(58) Field of Classification Search ................ 514/13, 514/2; 530/300, 324, 326; 435/23, 24, 7.72
See application file for complete search history.

(56) References Cited

U.S. PATENT DOCUMENTS

| | | |
|---|---|---|
| 4,557,862 A | 12/1985 | Mangel et al. |
| 4,648,893 A | 3/1987 | Roux |
| 4,708,929 A | 11/1987 | Henderson |
| 4,780,421 A | 10/1988 | Kameda et al. |
| 4,897,444 A | 1/1990 | Brynes et al. |
| 5,011,910 A | 4/1991 | Marshall et al. |
| 5,110,801 A | 5/1992 | Leveen et al. |
| 5,118,801 A | 6/1992 | Lizardi et al. |
| 5,212,298 A | 5/1993 | Rademacher et al. |
| 5,312,728 A | 5/1994 | Lizardi et al. |
| 5,506,115 A | 4/1996 | Toth et al. |
| 5,539,082 A | 7/1996 | Nielsen et al. |
| 5,605,809 A | 2/1997 | Komoriya et al. |
| 5,652,107 A | 7/1997 | Lizardi et al. |
| 5,698,411 A | 12/1997 | Lucas et al. |
| 5,714,342 A | 2/1998 | Komoriya et al. |
| 5,714,392 A | 2/1998 | Dawson et al. |
| 5,723,288 A | 3/1998 | Dykstra et al. |
| 5,759,773 A | 6/1998 | Tyagi et al. |
| 5,776,720 A | 7/1998 | Jaffe et al. |
| 5,804,395 A | 9/1998 | Schade et al. |
| 5,807,674 A | 9/1998 | Tyagi et al. |
| 5,871,946 A | 2/1999 | Lucas et al. |
| 5,912,137 A | 6/1999 | Tsien et al. |
| 5,925,517 A | 7/1999 | Tyagi et al. |
| 5,925,558 A | 7/1999 | Tsien et al. |
| 5,998,204 A | 12/1999 | Tsien et al. |
| 6,037,130 A | 3/2000 | Tyagi et al. |
| 6,037,137 A | 3/2000 | Komoriya et al. |
| 6,103,476 A | 8/2000 | Tyagi et al. |
| 6,150,097 A | 11/2000 | Tyagi et al. |
| 6,410,255 B1 | 6/2002 | Pollok et al. |

FOREIGN PATENT DOCUMENTS

| | | |
|---|---|---|
| EP | 0 242 095 A | 10/1987 |
| WO | WO 96/13607 | 5/1996 |
| WO | WO 98/10096 | 3/1998 |
| WO | WO 98/37226 A1 | 8/1998 |
| WO | WO 00/06778 | 2/2000 |
| WO | WO 00/71562 A1 | 11/2000 |
| WO | WO 00/71740 A1 | 11/2000 |
| WO | WO 01/18238 A1 | 3/2001 |
| WO | WO 01/31062 A1 | 5/2001 |

OTHER PUBLICATIONS

Harvey et al. "Caspase-dependent Cdk Activity is a Requisite Effector of Apoptitic Death Events" Jol. Of Cell Biol. vol. 148, No. 1, Jan. 10, 2000, p. 59-72.
Ekert et al. "Inhibition of Apoptisis and Clonogenic Survival of Cells Expressing crmA Variants: Optimal Caspase Substrates are Not Necessarily Optimal Inhibitors" EMBO Jol. vol. 18, No. 2, 330-338, (1999).
Robles et al. "Localization, Regulation and Possible Consequences of Apoptic Protease-Activating Factor-1 (Apaf-1) Expression in Granulosa Cells of the Mouse Ovary" Abstract Endocinology Jun. 1999 140(6), p. 2641-2644.

(Continued)

*Primary Examiner*—Chih-Min Kam
(74) *Attorney, Agent, or Firm*—Beyer Weaver LLP; Tom Hunter

(57) ABSTRACT

The present invention provides for novel reagents whose fluorescence increases in the presence of particular proteases. The reagents comprise a characteristically folded peptide backbone conjugated to two fluorophores such that the fluorophores are located opposite sides of a cleavage site. When the folded peptide is cleaved, as by digestion with a protease, the fluorophores provide a high intensity fluorescent signal at a visible wavelength. Because of their high specificity and their high fluorescence signal in the visible wavelengths, these protease indicators are particularly well suited for detection of protease activity in biological samples, in particular in frozen tissue sections. Thus this invention also provides for methods of detecting protease activity in situ in frozen sections.

37 Claims, 11 Drawing Sheets

OTHER PUBLICATIONS

Perez et al. "Fragmentation and Death (aka apoptisis) of Ovulated Oocytes" Molecular Human Reproduction vol. 5, No. 5, 414-420, (1999).

Zapata et al. "Granzyme Release and Caspase Activation in Activated Human T-Lymphocytes" Jol. Of Biol. Chem. vol. 273,No. 12, pp. 6916-6920 (1998).

Siegel et al. "Death-Effector Filaments: Novel Cytoplasmic Structures that Recruit Caspases and Trigger Apoptisis" Jol. Of Cell Biol. vol. 141, No. 5, Jun. 1, 1998.

Hirata et al. "Caspases Are Activated in a Branched Protease Cascade and Control Distinct Downstream Processes in Fas-Induced Apoptosis" J. of Exp. Med. vol. 187, No. 4, Feb. 16, 1998, p. 587-600.

Komoriya et al. "Assessment of Caspase Activities in Intact Apoptotic Thymocytes Using Cell-Permeable Fluorogenic Caspase Substrates" J. of Exp. Med. vol. 191, No. 11, 1819-1828, Jun. 5, 2000.

Packard et al. "Intramolecular Excitonic Dimers in Protease Substrates: Modification of the Backbone Moiety to Probe the H-Dimer Structure" J. Phys. Chem. B pp. 1820-1827 1998.

Pacard et al. "Intramolecular Resonance Dipole-Dipole Interactions in a Profluoescent Protease" J. Phys. Chem. B. pp. 752-758, 1998.

Packard et al. "Characterization of Fluorescence Quenching in Bifluorophoric Protease Substrates", Biochysical Chemistry 67 (1997) 167-176.

Packard et al. "Structural Charactristics of Fluorophores that Form Intramolecular H-Type Dimers in a Protease in a Protease Substrate", J. Phys. Chem. B (1997) 101, 5070-5074.

Packard et al. "Design of Profluorescent Protease Substrates Guided by Exciton Theory", Methods in Enzymology, vol. 278, 15-28, (1997).

Packard et al. "Profluorenscent Protease Substrates: Intramolecular Dimers Described by the Exciton Model", Proc. Natl. Acad. Sci. vol. 93, pp. 11640-11645, Oct. 1996.

Knight et al. "A novel coumarin-labelled peptide for sensitive continuous assats of the matrix metalloproteinases." *FEBBS Letters* 296(3):263-266 (1992).

Carmel et al. "Use of Substrates with Fluorescent Donor and Acceptor Chromophores for the Kinetic Assay of Hydrolases." *FEBBS Letters* 30(1):11-14 (1973).

Isaac et al. "Use of Flurescence Resonance Energy Transfer to Estimate Intramolecular Distances in the Msx-1 Homeodomain." *Biochemistry* 34(1):15276-15281 (1995).

Keller et al. "Mode of Insertion of the Signal Sequence of a Bacterial Precusor Protein into Phospholipid Bilayers As Revealed by Cysteine-Based Site Directed Spectroscopy." *Biochemistry* 35:3063-3071 (1996).

Latt et al. "Flourescence Determination of Carboxypeptidase A Activity Based on Electronic Energy Transfer." *Analytical Biochemistry* 50:56 (1972).

Matayoshi et al. "Novel Fluorogenic Substrates for Assaying Retroviral Proteases by Resonance Energy Transfer." *Science* 247 (1990).

Matsuzaki et al. "Translocation of a Channel-Forming Antimicrobial Peptide, Maganin 2, across Lipid Bilayers by Forming a Pore." *Biochemistry* 34:6521-6526 (1995).

Nagase et al. "Design and Characterization of a Fluorogenic Substrate Selectively Hydrolyzed by Stromelysin 1 (Matrix Metalloproteinase-3)" *J. of Biol. Chem* 269:20952 (1994).

Packard et al. Intramolecular Excitonic Dimers in Protease Substrated: Modification of the Backbone Moiety to Probe the H-Dimer Structure. *American Chem Society* 1-8 (1998).

Parkhurst et al. "Donor-Accoptor Distance Distributions in a Double-Labeled Fluorescent Oligonucleotide Both as a Single Strand and in Duplexes." *Biochemistry* 34(1):293-300 (Jan. 1995).

Parkhurst et al. Kinetic Studies by Fluorescence Resonance Energy Transfer Employing a Double-Labeked Oligonucleotide: Hybridization to the Oligonucleotide Complement and to Single Strand DNA *Biochemistry* 34:285-292 (1995).

Wang et al. "Design and Synthesis of New Fluorogenic HIV Protease Substrates Based on Resonance Energy Transfer." *Tetrahedron Letters* 31:6493 (1990).

Wu et al. "Resonance Energy Transfer: Methods and Applications." *Analytical Biochemistry* 218:1-13 (1994).

Yang et al. "Conformational Flexibility of Three-Way DNA Junctions Containing Inpaired Nucleotides." *Biochemistry* 35:7959-7967 (1996).

Finucane et al. "Bax-induced Caspase Activation and Apoptosis via Cytochrome c Release from Mitochondria Is Inhibitable by Bcl-xL" Abstract J Biol Chem, vol. 274, Issue 4, 2225-2233, Jan. 22, 1999.

Kanuka et al. "Proapoptotic activity of Caenorhabditis elegans CED-4 protein in Drosophila: Implicated mechanisms for caspase activation" Proc. Natl. Acad. Sci. USA vol. 96, pp. 145-150, Jan. 1999.

GENERIC NAME: DIALKYLATEDCARBOCYANINE DYES $n \geq 0$
$x, y = (CH_3)_2C, \overset{H}{N}, O, S, ETC.$

COMPOSITIONS FOR THE DETECTION OF ENZYME ACTIVITY IN BIOLOGICAL SAMPLES AND METHODS OF USE THEREOF

CROSS-REFERENCE TO RELATED APPLICATIONS

This is a continuation-in-part of PCT/US00/24882, filed on Sep. 11, 2000, designating the United States, which is a continuation-in-part of U.S. application Ser. No. 09/394,019, filed on Sep. 10, 1999, now U.S. Pat. 6,936,687, which is a continuation-in-part of PCT/US98/03000, filed on Feb. 20, 1998, designating the United States, which is a continuation-in-part of U.S. application Ser. No. 08/802,981, filed on Feb. 20, 1997, now U.S. Pat. No. 6,037,137, all of which are herein incorporated by reference in their entirety for all purposes.

FIELD OF THE INVENTION

This invention pertains to a class of novel fluorogenic compositions whose fluorescence level increases in the presence active proteases. These fluorogenic protease indicators typically fluoresce at visible wavelengths and are thus highly useful for the detection and localization of protease activity in biological samples.

BACKGROUND OF THE INVENTION

Proteases represent a number of families of hydrolytic enzymes that catalytically hydrolyze peptide bonds. Principal groups of proteases include metalloproteases, serine proteases, cysteine proteases and aspartic proteases. Proteases, in particular serine proteases, are involved in a number of physiological processes such as blood coagulation, fertilization, inflammation, hormone production, the immune response and fibrinolysis.

Numerous disease states are caused by and can be characterized by alterations in the activity of specific proteases and their inhibitors. For example emphysema, arthritis, thrombosis, cancer metastasis and some forms of hemophilia result from the lack of regulation of serine protease activities (see, for example, *Textbook of Biochemistry with Clinical Correlations*, John Wiley and Sons, Inc. N.Y. (1993)). In case of viral infection, the presence of viral proteases have been identified in infected cells. Such viral proteases include, for example, HIV protease associated with AIDS and NS3 protease associated with Hepatitis C. These viral proteases play a critical role in the virus life cycle.

Proteases have also been implicated in cancer metastasis. Increased synthesis of the protease urokinase has been correlated with an increased ability to metastasize in many cancers. Urokinase activates plasmin from plasminogen which is ubiquitously located in the extracellular space and its activation can cause the degradation of the proteins in the extracellular matrix through which the metastasizing tumor cells invade. Plasmin can also activate the collagenases thus promoting the degradation of the collagen in the basement membrane surrounding the capillaries and lymph system thereby allowing tumor cells to invade into the target tissues (Dano, et al. (1985) *Adv. Cancer. Res.*, 44: 139.

Clearly measurement of changes in the activity of specific proteases is clinically significant in the treatment and management of the underlying disease states. Proteases, however, are not easy to assay. Typical approaches include ELISA using antibodies that bind the protease or RIA using various labeled substrates. With their natural substrates assays are difficult to perform and expensive. With currently available synthetic substrates the assays are expensive, insensitive and nonselective. In addition, many "indicator" substrates require high quantities of protease which results, in part, in the self destruction of the protease.

Recent approaches to protease detection rely on a cleavage-induced spectroscopic change in a departing chromogen or fluorogen located in the P1' position (the amino acid position on the carboxyl side of the cleavable peptide bond) (see, for example U.S. Pat. Nos. 4,557,862 and 4,648,893). However, many proteases require two or four amino acid residues on either side of the scissile bond for recognition of the protease (a specific protease may require up to 6 amino acid residues) and thus, these approaches lack protease specificity.

Recently however, fluorogenic indicator compositions have been developed in which a "donor" fluorophore is joined to an "acceptor" chromophore by a short bridge containing a (7 amino acid) peptide that is the binding site for an HIV protease and linkers joining the fluorophore and chromophore to the peptide (Wang et al. (1990) *Tetra. Letts.* 45: 6493-6496). The signal of the donor fluorophore was quenched by the acceptor chromophore through a process believed to involve resonance energy transfer (RET). Cleavage of the peptide resulted in separation of the chromophore and fluorophore, removal of the quench and a subsequent signal was measured from the donor fluorophore.

The design of the bridge between the donor and the acceptor led to relatively inefficient quenching limiting the sensitivity of the assay. In addition, the chromophore and/or fluorophore absorbed light in the ultraviolet range reducing the sensitivity for detection in biological samples which typically contain molecules that absorb strongly in the ultraviolet. Broad utility of these substrates was also limited by the modifications to existing equipment required for optimal measurements.

Clearly fluorogenic protease indicators that show a high signal level when cleaved, and a very low signal level when intact, that show a high degree of protease specificity, and that operate exclusively in the visible range thereby rendering them suitable for use in biological samples are desirable. The compositions of the present invention provide these and other benefits.

SUMMARY OF THE INVENTION

The present invention provides for novel reagents whose fluorescence increases in the presence of particular proteases. These fluorogenic protease indicators provide a high intensity fluorescent signal at a visible wavelength when they are digested by a protease. Because of their high fluorescence signal in the visible wavelengths, these protease indicators are particularly well suited for detection of protease activity in biological samples, in particular, in frozen tissue section and cultured or freshly isolated cells. The measurement can be carried out, e.g., using a fluorescence microscope for histological samples, cells, and the like and using a flow cytometer or microscope for cell suspensions. Hence, the fluorogenic compositions of this invention allow detection of intracellular protease activity.

The fluorogenic protease indicators of the present invention are compositions suitable for detection of the activity of a protease. These compositions have the general formula:

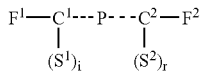

in which P is a peptide comprising a protease binding site for said protease consisting of 2 to about 15, preferably 2 to about 12, preferably 2 to about 10, preferably 2 to about 8, 2 to about 6, or 2 to about 4 amino acids; $F^1$ and $F^2$ are fluorophores; $S^1$ and $S^2$ are peptide spacers ranging in length from 1 to about 50 amino acids; i and r are independently 0 or 1; and $C^1$ and $C^2$ are conformation determining regions comprising peptides ranging in length from 1 to about 8, amino acids, more preferably from 1 to about 6 amino acids. The conformation determining regions each introduce a bend into the composition or otherwise restrict the degrees of freedom of the peptide backbone, thereby juxtaposing the fluorophores with a separation of less than about 100 Å. When either of the spacers ($S^1$ and $S^2$) are present they are linked to the protease binding site by a peptide bond to the alpha carbon of the terminal amino acid. Thus, when i is 1, $S^1$ is joined to $C^1$ by a peptide bond through a terminal amino group of $C^1$, and when r is 1, $S^2$ is joined to $C^2$ by a peptide bond through a terminal alpha carboxyl group of $C^2$.

The amino acid residues comprising a protease binding site are, by convention, numbered relative to the peptide bond hydrolyzed by a particular protease. Thus the first amino acid residue on the amino side of the cleaved peptide bond is designated $P_1$ while the first amino acid residue on the carboxyl side of the cleaved peptide bond is designated $P_1'$. The numbering of the residues increases with distance away from the hydrolyzed peptide bond. Thus a four amino acid protease binding region would contain amino acids designated:

and the protease would cleave the binding region between $P_1$ and $P_1'$.

In particularly preferred embodiments, the fluorogenic compositions of this invention are compositions of Formula II and Formula V as described herein. Preferred fluorogenic indicators according to this invention have conformation determining regions and, optionally, spacers as described herein. In a most preferred embodiment, the compositions bear a single species of fluorophore. Fluorophores suitable for these "homolabeled" compositions include fluorophores that form H-type dimers. Particularly preferred fluorophores have an excitation wavelength between about 300 and 800 nm, more preferably between about 310 nm and about 750 nm, most preferably between about 315 nm and about 700 nm.

In another embodiment, this invention provides methods of detecting the activity of a protease. The methods involve contacting the protease with one or more of the protease indicators described herein. In a particularly preferred embodiment, the "contacting" is in a histological section or in a cell suspension, or culture, or material derived from a biological sample including, but not limited to a tissue, blood, urine, saliva, or other biofluid, lymph, biopsy. The detection method can include a method selected from the group consisting of fluorescence microscopy, fluorescence microplate reader, flow cytometry, fluorometry, absorption spectroscopy.

In preferred compositions $F^1$ can be 5- and/or 6-carboxytetramethylrhodamine; and $F^2$ can be rhodamine X acetamide. These compositions may be conjugated to a solid support or to a lipid including membrane lipids or liposomes.

In another embodiment, any of the compositions described above may be used in a method for detecting protease activity in a sample. The sample may be a sample of "stock" protease, such as is used in research or industry, or it may be a biological sample. Thus, this invention provides for a method of detecting protease activity in a sample by contacting the sample with any of the compositions described above and then detecting a change in fluorescence of the fluorogenic composition where an increase in fluorescence indicates protease activity. The sample is preferably a biological sample which may include biological fluids such as sputum or blood, tissue samples such as biopsies or sections, and cell samples either as biopsies or in culture. Particularly preferred are tissue sections, cultured cells, cultured tissues, and the like.

In still yet another embodiment, this invention provides a method of delivering a molecule into a cell. The method involves providing the molecule attached to at least two fluorophore molecules and a hydrophobic group; and contacting the cell with the molecule whereby the molecule enters the cell. In one embodiment, the method involves providing the molecule attached to at least two largely flat hydrophobic fluorophore molecules and a hydrophobic group. Preferred molecules include a polypeptide, a nucleic acid, a lipid, an oligosaccharide. Suitable fluorophores and hydrophobic groups are described herein. Preferred cells include mammalian cells.

In still another ebodiment, this invention provides a method of screening a test agent for the ability to modualte a protease (or a nuclease, lipase, etc.). The method involves contacting a protease or a cell comprising a protease with the test agent; contacting the protease with a fluorogenic indicator composition as described herein; and detecting a signal or lack of signal produced by the fluorogenic composition where a difference in the signal produced by the protease or cell contacted with the test agent compared to a control (e.g. a negative control) in which the protease or cell is contacted by said test agent at a lower concentration indicates that the test agent modulates activity of the protease. In preferred embodiments, the control comprises the absence of the test agent. Typically, an an increase in signal produced by the protease or cell contacted with the test agent as compared to the control indicates that the test agent increases the activity of said protease, while a decrease in signal (e.g. fluorescence) produced by the protease or cell contacted with the test agent as compared to the control indicates that the test agent decreases the activity of said protease. The protease is contacted with the fluorogenic composition in the presence of the test agent in certain embodiments. In certain other embodiments, the protease is contacted with the fluorogenic composition after removal of the test agent. The method can further entail entering test agents that modulate activity of said protease into a database comprising a list of test agents modulating said protease. In various embodiments, the detecting comprises detecting an intracellular signal (e.g., via microscopy, flow cytometry, etc.). In certain particularly preferred embodiments, the detecting comprises high-throughput screening of whole cells.

DEFINITIONS

The term "protease binding site" is used herein to refer to an amino acid sequence that is characteristically recognized and cleaved by a protease. The protease binding site contains a peptide bond that is hydrolyzed by the protease and the amino acid residues joined by this peptide bond are said to form the cleavage site. These amino acids are designated $P_1$ and $P_1'$ for the residues on the amino and carboxyl sides of the hydrolyzed bond respectively.

A fluorophore is a molecule that absorbs light at a characteristic wavelength and then re-emits the light most typically at a characteristic different wavelength. Fluorophores are well known to those of skill in the art and include, but are not limited to rhodamine and rhodamine derivatives, fluorescein and fluorescein derivatives, coumarins and chelators with the lanthanide ion series. A fluorophore is distinguished from a chromophore which absorbs, but does not characteristically re-emit light.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free-amino group on an amino acid at the amino terminal of a peptide or to the-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

The polypeptides described herein are preferably written with the amino terminus at the left and the carboxyl terminus at the right. The amino acids comprising the peptide components of this invention are numbered with respect to the protease cleavage site, with numbers increasing consecutively with distance in both the carboxyl and amino direction from the cleavage site. Residues on the carboxyl site are either lotated with a "'" as in $P_1'$, or with a letter and superscript indicating the region in which they are located. The "'" indicates that residues are located on the carboxyl side of the cleavage site.

The term "residue" or "amino acid" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

The term "domain" or "region" refers to a characteristic region of a polypeptide. The domain may be characterized by a particular structural feature such as a β turn, an alpha helix, or a β pleated sheet, by characteristic constituent amino acids (e.g. predominantly hydrophobic or hydrophilic amino acids, or repeating amino acid sequences), or by its localization in a particular region of the folded three dimensional polypeptide. As used herein, a region or domain is composed of a series of contiguous amino acids.

The terms "protease activity" or "activity of a protease" refer to the cleavage of a peptide by a protease. Protease activity comprises the "digestion" of one or more peptides into a larger number of smaller peptide fragments. Protease activity of particular proteases may result in hydrolysis at particular peptide binding sites characteristically recognized by a particular protease. The particular protease may be characterized by the production of peptide fragments bearing particular terminal amino acid residues.

The terms "nucleic acid" or "oligonucleotide" refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphosphoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments. Preferred nucleic acid backbones used in this invention range from about 5 nucleotides to about 500 nucleotides, preferably from about 10 nucleotides to about 100 nucleotides, more preferably from about 10 nucleotides to about 50 nucleotides, and most preferably from about 12 or 15 nucleotides to about 30, 40, or 50 nucleotides in length.

The term "test agent" refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 3000 Da, more preferably up to 2000 Da, and most preferably up to about 1000 Da.

The term macromolecule refers to a "large" molecule. Biopolymers (e.g. proteins, glycoproteins, carbohydrates, lipids, polysaccharides, and the like) are typical macromolecules. Typical macromolecules have a molecular weight greater than about 1000 Da, preferably greater than about 2000 Da, more preferably greater than about 3000 Da, and most preferably greater than about 4,000 or 5,000 Da.

The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

The term "biological sample", as used herein, refers to a sample obtained from an organism, from components (e.g., cells or tissues) of an organism, and/or from in vitro cell or tissue cultures. The sample may be of any biological tissue or fluid (e.g. blood, serum, lymph, cerebrospinal fluid, urine, sputum, etc.). Biological samples can also include whole organisms, organs or sections of tissues such as frozen sections taken for histological purposes.

The term "specifically binds", when referring to the interaction of a nucleic acid binding protein and a nucleic acid binding site or two proteins or other binding pairs refers to a binding reaction which is determinative of the presence of the one or other member of the binding pair in the presence of a heterogeneous population of molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, etc. The binding may be by one or more of a variety of mechanisms including, but not limited to ionic interactions, covalent interactions, hydrophobic interactions, van der Waals interactions, etc.

The terms "binding partner", or a member of a "binding pair", or "cognate ligand" refers to molecules that specifically bind other molecules to form a binding complex such as antibody/antigen, lectin/carbohydrate, nucleic acid/nucleic acid, receptor/receptor ligand (e.g. IL-4 receptor and IL-4), avidin/biotin, etc.

The term ligand is used to refer to a molecule that specifically binds to another molecule. Commonly a ligand is a soluble molecule, e.g. a hormone or cytokine, that binds to a receptor. The decision as to which member of a binding pair is the ligand and which the "receptor" is often a little arbitrary when the broader sense of receptor is used (e.g., where there is no implication of transduction of signal). In these cases, typically the smaller of the two members of the binding pair is called the ligand. Thus, in a lectin-sugar interaction, the sugar would be the ligand (even if it is attached to a much larger molecule, recognition is of the saccharide).

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. Stringent hybridization and stringent hybridization wash conditions in the context of nucleic acid hybridization are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, chapt 2, Overview of principles of hybridization and the strategy of nucleic acid probe assays*, Elsevier, N.Y. (Tijssen). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook (1989) *Molecular Cloning: A Laboratory Manual* (2nd ed.) Vol. 1-3, Cold Spring Harbor Laboratory, Cold Spring Harbor Press, NY, and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook supra.) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4×to 6×SSC at 40° C. for 15 minutes.

The term "nucleic acid array" refers to a collection of nucleic acids comprising a multiplicity of different nucleic acids (nucleic acid species). The nucleic acids are typically attached to a solid support. The support can be contiguous and of virtually any convenient geometry (e.g. a glass or quartz slide). In other embodiments, the support is not contiguous, e.g., where the array nucleic acids are disposed on a collection of particles, e.g. beads. The nucleic acids comprising the array can be chemically synthesized nucleic acids, naturally occurring nucleic acids, cloned nucleic acids, or any combination thereof. Preferred nucleic acid arrays are "high density arrays" or "microarrays". Typically such microarrays have a density of greater than about 100, preferably greater than about 1000, more preferably greater than about 10,000, and most preferably greater than about 100,000 array elements per square centimeter.

The term "array element" refers to a domain of an array comprising substantially one species of nucleic acid.

Two fluorophores are said to quench each other in an H-dimer when their aggregate fluorescence in an H-dimer formation is detectably less than the aggregate fluorescence of the fluorophores when they are separated (e.g. in solution at approximately 10 μM or less). In preferred embodiments the fluorophores quench by at least 50%, preferably by at least 70%, more preferably by at least 80%, and most preferably by at least 90%, 95%, or even at least 99%.

Certain amino acids referred to herein are described by shorthand designations as shown in Table 1.

TABLE 1

Amino acid nomenclature.

| Name | Abbreviation | |
|---|---|---|
| | 3 Letter | 1 Letter |
| Alanine | Ala | A |
| βAlanine (NH$_2$—CH$_2$—CH$_2$2—COOH) | βAla | |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| epsilon-aminocaproic acid (NH$_2$—(CH$_2$)$_5$—COOH) | Ahx | J |
| 4-aminobutanoic acid (NH$_2$—(CH$_2$)$_3$—COOH) | gAbu | — |
| tetrahydroisoquinoline-3-carboxylic acid | — | O |
| 8-aminocaprylic acid | — | C7 |
| 4-aminobutyric acid | — | C3 |
| Lys(N(epsilon)-trifluoroacetyl) | — | K[TFA] |
| α-aminoisobutyric acid | Aib | B |

Other abbreviations used herein include "Fm" for Fmoc (9-fluorenyl-methoxycarbonyl) group, "Ac" for N(alpha)-acetyl group, "daa" or (d-aa) where "d" indicates the d isomer of the aa, and "Z" for benzyloxycarbonyl group.

BRIEF DESCRIPTION OF THE DRAWINGS

FIG. 1A: HPLC before the addition of elastase showing the late eluting peak representing the intact indicator molecule. FIG. 1B: HPLC after the addition of elastase with detection at 550 nm where both fluorophores absorb. FIG. 1C HPLC after the addition of elastase with detection at 580 nm where $F^2$ absorbs maximally.

(FIG. 6A) Dexamethasone (final concentration 0.1 mM) was added to freshly isolated mouse thymocytes that were incubated at 37° C. for various times before washing and adding one of five caspase substrates. Incubation with substrate was then carried out for an additional 60 min. The time of exposure of cells to dexamethasone is indicated in the left margin of each panel. Forward angle light scatter from incubation without substrate addition is shown at the left; these histograms were identical to those of cells with substrates. (FIG. 6B) Thymocytes cultured on antiFas-coated wells were analyzed as in A.

(FIG. 7A) Time course of cells incubated with 10 mM DEVDase (red) and VEIDase (green) substrates. The apoptosis inducing agent, 0.1 mM dexamethasone, and two substrates were present continuously. Confocal images of cells at 20 min intervals starting at 90 min are shown here. The yellow color indicates the presence of both caspase activities. (FIG. 7B) Fluorescence images of caspases in apoptotic thymocytes derived from VEIDase (CaspaLux6™) and DEVDase (PhiPhiLux™) are shown separately to assess their differential activity, as well as the additive image similar to A. These images are from the 140 min time point of the experiment shown in A. The Nomarski image is in the lower right. The dark images of cells in each fluorescence image correspond to those cells in which intracellular caspase activation is not yet detectable. (FIG. 7C) Time course of activation of the DEVDase (circles) and VEIDase (squares) activities compared with the cell cross-sectional area (triangles) plotted from the single cell shown. Both area and fluorescence are shown in arbitrary units, relative to the 92 min time point.

DETAILED DESCRIPTION

I. Fluorogenic Indicators of Protease Activity

Figure 1A:
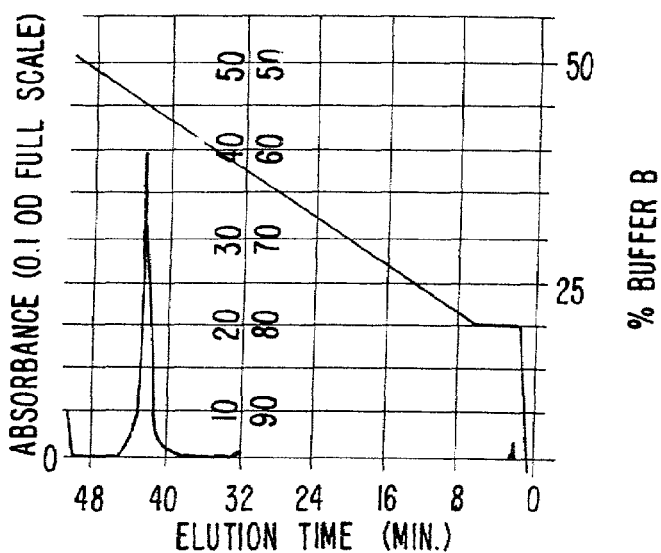
FIGS. 1A, 1B, and 1C show an HPLC analysis of the D-NorFES-A protease indicator ($F^1$-Asp-Ala-Ile-Pro-Nle-Ser-Ile-Pro-Cys-$F^2$) where $F^1$ is a donor (D) fluorophore (5'-carboxytetramethylrhodamine (C2211) and $F^2$ is an acceptor (A) fluorophore (rhodamine X acetamide (R492))) before and after the addition of elastase.

This invention provides for novel fluorogenic molecules useful for detecting protease activity in a sample. In certain embodiments, the fluorogenic protease indicators of the present invention generally comprise a fluorophore (donor) linked to an "acceptor" molecule by a peptide having an amino acid sequence that is recognized and cleaved by a particular protease. The donor fluorophore typically is excited by incident radiation at a particular wavelength which it then re-emits at a different (longer) wavelength. When the donor fluorophore is held in close proximity to the acceptor molecule, the acceptor absorbs the light re-emitted by the fluorophore thereby quenching the fluorescence signal of the donor molecule, or the putative donor and acceptor form a complex which absorbs the incident light and does not release radiative energy until the complex is disrupted. In this latter embodiment, the quench occurs whether the two fluorophores are different or the same species. Thus, in addition to peptides double labeled with two different fluorophores as shown in Example 1, peptides double labeled with the same fluorophore (or chromophore) may also be used as protease indicators (see, e.g., Example 3). Cleavage of the (e.g. peptide) backbone joining the two fluorophores or chromophores results in separation of the two molecules, release of the quenching effect and increase in fluorescence or a change in spectral characteristics.

In one basic application, the fluorogenic molecules of this invention may be used to assay the activity of purified protease made up as a reagent (e.g. in a buffer solution) for experimental or industrial use. Like many other enzymes, proteases may loose activity over time, especially when they are stored as their active forms. In addition, many proteases exist naturally in an inactive precursor form (e.g. a zymogen) which itself must be activated by hydrolysis of a particular peptide bond to produce the active form of the enzyme prior to use. Because the degree of activation is variable and because proteases may loose activity over time, it is often desirable to verify that the protease is active and to often quantify the activity before using a particular protease in a particular application.

Previous approaches to verifying or quantifying protease activity involve combining an aliquot of the protease with its substrate, allowing a period of time for digestion to occur and then measuring the amount of digested protein, most typically by HPLC. This approach is time consuming, utilizes expensive reagents, requires a number of steps and entails a considerable amount of labor. In contrast, the fluorogenic reagents of the present invention allow rapid determination of protease activity in a matter of minutes in a single-step procedure. An aliquot of the protease to be tested is simply added to, or contacted with, the fluorogenic reagents of this invention and the subsequent change in fluorescence is monitored (e.g., using a fluorimeter or a fluorescence microplate reader).

In addition to determining protease activity in "reagent" solutions, the fluorogenic compositions of the present invention may be utilized to detect protease activity in biological samples. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, blood, blood cells (e.g., white cells), tissue or fine needle biopsy samples, urine, peritoneal fluid, and pleural fluid, or cells therefrom. Biological samples may also include sections of tissues such as frozen sections taken for histological purposes.

Previously described fluorogenic protease indicators typically absorb light in the ultraviolet range (e.g., Wang et al., supra.). They are thus unsuitable for sensitive detection of protease activity in biological samples which typically contain constituents (e.g., proteins) that absorb in the ultraviolet range. In contrast, in preferred embodiments, the fluorescent indicators of the present invention both absorb and emit in the visible range (400 nm to about 750 nm). These signals are therefore not readily quenched by, nor is activation of the fluorophores, that is, absorption of light, interfered with by background molecules; therefore they are easily detected in biological samples.

In addition, unlike previous fluorogenic protease indicators which often utilize a fluorophore and a quenching chromophore, the indicators of the present invention may utilize two fluorophores (i.e., fluorophore as both donor and acceptor), a fluorophore and a chromophore, or the same two fluorophores effectively forming a ground-state dimer when joined by the one of the peptide backbones of this invention. Pairs of fluorophores may be selected that show a much higher degree of quenching than previously described chromophore/fluorophore combinations. In fact, previous compositions have been limited to relatively low efficiency fluorophores because of the small degree of quenching obtainable with the matching chromophore (Wang et al. supra.). In contrast, the fluorogenic protease indicators of this invention utilize high efficiency fluorophores and are able to achieve a high degree of quenching while providing a strong signal when the quench is released by cleavage of the peptide substrate. The high signal allows detection of very low levels of protease activity. Thus the fluorogenic protease indicators of this invention are particularly well suited for in situ detection of protease activity.

Preferred fluorogenic protease indicators of the present invention have the general formula:

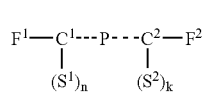

I where P is a peptide comprising a protease binding site, $F^1$ and $F^2$ are fluorophores, $C^1$ and $C^2$ are conformation determining regions, and $S^1$ and $S^2$ are optional peptide spacers. $F^1$ may be the donor fluorophores or chromophore while $F^2$ is the acceptor fluorophores or chromophore, or conversely, $F^1$ may be the donor fluorophore or chromophore while $F^1$ is the acceptor fluorophores or chromophore, or $F^1$ and $F^2$ may be identical (fluorophores or chromophores). The protease binding site provides an amino acid sequence (a peptide) that is recognized and cleaved by the protease whose activity the indicator is designed to reveal. The protease binding site is typically a peptide ranging in length from 2 amino acids to about 12 amino acids, 2 to about 10, 2 to about 8, 2 to about 6 or 2 to about 4 amino acids in length.

A preferred conformation determining region is an amino acid sequence that allows a bend into the molecule, restricts the degrees of freedom of the peptide backbone, or otherwise results in the two ends of the backbone being in close proximity. The combined effect of the two conformation determining regions is to juxtapose the fluorophores or chromophores attached to the amino and carboxyl termini of $C^1$ and $C^2$ respectively. The fluorophores are thus preferably positioned adjacent to each other at a distance less than about 100 angstroms. The fluorophores ($F^1$ and $F^2$) are typically conjugated directly to the conformation determining regions, although they may be joined by linkers. The optional spacers ($S^1$ and $S^2$), when present, can be used to link the composition to a solid support or to anchor the composition to a component of a biological sample (e.g., to a cellular membrane). The spacers can also provide additional, or alternative, functionality. For example, a spacer can comprise the amino acids GY to provide an optical signature for ready detection of the peptide by HPLC.

The conformation determining regions substantially increase the protease specificity of the composition. The amino acid sequences comprising the conformation determining regions are typically less accessible to the enzyme due to steric hindrance with each other and with the attached fluorophores. Conversely, the protease binding site is relatively unobstructed by either the fluorophore or the conformational determining region and is thus readily accessible to the protease.

II. Protease Binding Site

In preferred embodiments, the protease binding site and conformation determining regions form a contiguous amino acid sequence (peptide). The protease binding site is an amino acid sequence that is recognized and cleaved by a particular protease. It is well known that various proteases cleave peptide bonds adjacent to particular amino acids. Thus, for example, trypsin cleaves peptide bonds following basic amino acids such as arginine and lysine and chymotrypsin cleaves peptide bonds following large hydrophobic amino acid residues such as tryptophan, phenylalanine, tyrosine and leucine. The serine protease elastase cleaves peptide bonds following small hydrophobic residues such as alanine.

A particular protease, however, will not cleave every bond in a protein that has the correct adjacent amino acid. Rather, the proteases are specific to particular amino acid sequences which serve as recognition domains for each particular protease. Without being bound by a particular theory, it is believed that a specific protease's preference for a particular cleavage site over many other potential sites in a folded globular protein may be largely determined by the potential cleavage site's amino acid sequences and also their conformation and conformational flexibility.

Thus, for example, one obtains limited proteolysis products, e.g., ribonuclease-S (a noncovalent complex consisting of two polypeptide chains) from a single chain folded protein ribonuclease-A using a protease called subtilisin. Similarly, one obtains a two chain noncovalent complex, Staphylococal nuclease-T, from single chain Staphylococcal nuclease by trypsin digestion. Another example of a specific protease's preference for one substrate over others is the human fibroblast-type collagenase. This protease prefers type I over type III soluble collagen even though both substrates contain the same collagenase sensitive Gly-Ile or Gly-Leu bonds (see, e.g., Birkedal-Hansen et. al. (1993) *Crit. Rev. in Oral Biology and Medicine* 4:197-250).

Any amino acid sequence that comprises a recognition domain and can thus be recognized and cleaved by a protease is suitable for the "protease binding site" of the fluorogenic protease indicator compositions of this invention. Known protease substrate sequences and peptide inhibitors of proteases posses amino acid sequences that are recognized by the specific protease they are cleaved by or that they inhibit. Thus known substrate and inhibitor sequences provide the basic sequences suitable for use in the protease recognition region. A number of protease substrates and inhibitor sequences suitable for use as protease binding domains in the compositions of this invention are indicated in Table 2.

One of skill will appreciate that this is not a complete list and that other protease substrates or inhibitor sequences may be used.

The amino acid residues comprising the protease binding site are, by convention, numbered relative to the peptide bond hydrolyzed by a particular protease. Thus the first amino acid residue on the amino side of the cleaved peptide bond is designated $P_1$ while the first amino acid residue on the carboxyl side of the cleaved peptide bond is designated $P_1'$. The numbering of the residues increases with distance away from the hydrolyzed peptide bond. Thus a four amino acid protease binding region would contain amino acids designated:

$P_2$-$P_1$-$P_1'$-$P_2'$ and the protease would cleave the binding region between $P_1$ and $P_1'$.

In certain preferred embodiments, the protease binding region of the fluorogenic protease indicators of the present invention is selected to be symmetric about the cleavage site. Thus, for example, where a binding region is Ile-Pro-Met-Ser-Ile (e.g. α-1 anti-trypsin) and the cleavage occurs between Met and Ser then a four amino acid residue binding region based on this sequence would be:

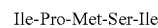

—$P_2$—$P_1$—$P_1'$—$P_2'$—

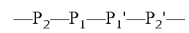

-Pro-Met-Ser-Ile-

Other examples of binding domains selected out of longer sequences are provided in Table 2. The remaining amino or carboxyl residues that are not within the protease binding domain may remain as part of the conformation determining regions subject to certain limitations as will be explained below. Thus, in the instant example, the amino terminal Ile may be incorporated into the $C^1$ conformation determining region.

Various amino acid substitutions may be made to the amino acids comprising the protease binding domain to increase binding specificity, to eliminate reactive side chains, or to reduce the conformational entropy (decrease degrees of freedom) of the molecule. Thus, for example, it is often desirable to substitute methionine (Met) residues, which bear a oxidizable sulfur, with norleucine. Thus, in the example given, a preferred protease binding region will have the sequence:

—$P_2$—$P_1$—$P_1'$—$P_2'$—

-Pro-Nle-Ser-Ile-

III. Conformation Determining Regions

Conformation determining regions ($C^1$ and $C^2$) are peptide regions on either end of the protease cleavage region that both stiffen and allow bends into the peptide backbone of the fluorogenic protease indicator molecules of this invention. In certain embodiments the conformation determining regions can introduce flexibility at particular locations, e.g. to permit the cleavage site to sit in a protein cleft.

The combination of the two conformation determining regions and the relatively straight protease cleavage region produces a roughly U-shaped molecule with the cleavage site at the base (middle) of the "U". The term U-shaped is, of course, approximate, the point being that, as described below, the fluorophores are held relatively rigidly in close juxtaposition (e.g., less than about 100 angstroms).

In one preferred embodiment, amino acids such as proline (Pro) and aminoisobutyric acid (Aib) are selected both to introduce bends into the peptide molecule and to increase the rigidity of the peptide backbone. The $C^1$ and $C^2$ domains are selected such that the "arms" of the U are rigid and the attached fluorophores are localized adjacent to each other at a separation of less than about 100 angstroms. In order to maintain the requisite stiffness of the peptide backbone and/or to provide the flexibility of adjacent residues such that a local bend at the binding site is possible to improve substrate specificity, the conformation determining regions are preferably 4 amino acids in length or less, or alternatively are greater than about 18 amino acids in length and form a stable alpha helix conformation, a β-pleated sheet, or loop.

A) Tetrapeptide Binding Site Compositions.

In a preferred embodiment, the peptide backbone of the fluorogenic protease indicators of the present invention will comprise a tripeptide $C^1$ region, a tetrapeptide P region and a single amino acid or dipeptide $C^2$ region. These compounds may be represented by the formula:

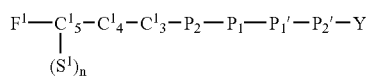  II where Y is either

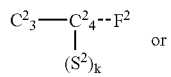 or  III

  IV

In these formulas the peptide binding region is designated $—P_2—P_1—P_1'—P_2'—$, while the amino acid residues of conformation determining regions $C^1$ and $C^2$ are designated $—C^1_5—C^1_4—C^1_3—$ and $—C^2_3—C^2_4—$ respectively. The $C^2$ region may either be an amino acid or a dipeptide. Whether the $C^2$ region is a dipeptide or an amino acid, the $F^2$ fluorophore and the $S^2$ spacer, when present, are always coupled to the carboxyl terminal residue of $C^2$. When a spacer is present on the $C^2$ region, it is attached the carboxyl terminal residue of $C^2$ by a peptide bond to the α carboxyl group.

As indicated above, the conformation determining regions typically contain amino acid residues such as a proline (Pro) that introduce a bend into the molecule and increase its stiffness. One of skill in the art will appreciate, however, that where the terminal residues of the protease binding region (P) are themselves bend-creating residues such as proline, it is not necessary to locate a bend-creating residue at the position closest to P in the C region attached to that terminus. The conformation determining regions are thus designed by first determining the protease binding region, as described above, determining the "left-over" residues that would lie in the conformation determining regions, and if necessary, modifying those residues according to the following guidelines:

1. If the $P_2'$ site is not a Pro then $C^2$ is a dipeptide (Formula III) Pro-Cys, Aib-Cys, Pro-Lys, or Aib-Lys, while conversely, if the $P_2'$ site is a Pro then $C^2$ is a single amino acid residue (Formula IV) Cys or Lys.

2. If the $P_2$ site is not a Pro then $C^1$ is a tripeptide consisting of Asp-$C^1_4$-Pro, Asp-$C^1_4$-Aib, Asp-Aib-Pro, Asp-Pro-$C^1_3$, Asp-Aib-$C^1_3$, Asp-Pro-Aib, or Asp-Aib-Aib, while if the $P_2$ site is a Pro residue then group $C^1$ is a tripeptide consisting of Asp-$C^1_4$—$C^1_3$ or Asp-$C^1_4$-Aib.

3. If the $P_3$ ($C^1_3$) residue is a Pro then $C^1$ is a tripeptide consisting of Asp-$C^1_4$-Pro or Asp-Aib-Pro.

5. If the $P_4$ ($C^1_4$) residue is a Pro then $C^1$ is a tripeptide consisting of Asp-Pro-$C^1_3$ or Asp-Pro-Aib.

5. If $P_2$ and $C^1_3$ are both not prolines then $C^1$ is a tripeptide consisting of Asp-Pro-$C^1_3$, Asp-Aib-$C^1_3$, Asp-$C^1_4$-Pro, Asp-$C^1_4$-Aib, Asp-Pro-Aib, or Asp-Aib-Pro.

As indicated above, any methionine (Met) may be replaced with a norleucine (Nle). A number of suitable peptide backbones consisting of $C^1$, P and $C^2$ are provided in Table 2.

TABLE 2

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. The thick line indicates the location at which the protease binding site is cleaved.

| Substrate/Inhibitor | CDR ($C^1$) | | | Protease Binding Site (P) | | | | CDR ($C^2$) | |
|---|---|---|---|---|---|---|---|---|---|
| | $C^1_5$ | $C^1_4$ | $C^1_3$ | $P_2$ | $P_1$ | $P_1'$ | $P_2'$ | $C^2_3$ | $C^2_4$ |
| α-1 anti-trypsin | Asp | Ala | Ile | Pro | Met | Ser | Ile | Pro | Cys |
| | | | | | Nle | | | Aib | Lys |
| plasminogen activator inhibitor 2 | Asp | Met Aib Pro | Thr Aib Pro | Gly | Arg | Thr | Gly | Pro Aib | Cys Lys |
| neutrophil leukocyte elastase inhibitor | Asp | Ala Aib | Thr Aib Pro | Phe | Cys | Met Nle | Leu | Pro Aib | Cys Lys |

TABLE 2-continued

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. The thick line indicates the location at which the protease binding site is cleaved.

| Substrate/Inhibitor | CDR ($C^1$) | | | Protease Binding Site (P) | | | | CDR ($C^2$) | |
|---|---|---|---|---|---|---|---|---|---|
| | $C^1_5$ | $C^1_4$ | $C^1_3$ | $P_2$ | $P_1$ | $P_1'$ | $P_2'$ | $C^2_3$ | $C^2_4$ |
| anti-plasmin inhibitor | Asp | Aib | Ser Aib Pro | Arg | Met Nle | Ser | Leu | Pro Aib | Cys Lys |
| anti α-1 thrombin | Asp | IleAib | Ala Aib Pro | Gly | Arg | Ser | Leu | Pro Aib | Cys Lys |
| α-1 antichymotrypsin | Asp | Aib | Thr Aib Pro | Leu | Leu | Ser | Leu | Pro Aib | Cys Lys |
| interstitial type III (human liver) collagen | Asp | Gly Aib | Pro Aib | Leu | Gly | Ile | Ala | Pro Aib | Cys Lys |
| type I collagen for collagenase Bovine α 1 | Asp | Gly Aib Pro | Pro Aib | Gln | Gly | Ile | Leu | Pro Aib | Cys Lys |
| type I collagen chick α2 | Asp | Gly Aib Pro | Pro Aib | Gln | Gly | Leu | Leu | Pro Aib | Cys Lys |
| human α1 type II collagen | Asp | Gly Aib Pro | Pro Aib | Gln | Gly | Ile | Ala | Pro Aib | Cys Lys |
| type III collagen - AIA | Asp | Gly Aib Pro | Pro Aib | Gln | Ala | Ile | Ala | Pro Aib | Cys Lys |
| type III collagen (human skin) | Asp | Gly Aib Pro | Pro Aib | Gln | Gly | Ile | Ala | Pro Aib | Cys Lys |
| human α 2 macroglobulin | Asp | Gly Aib Pro | Pro Aib | Glu | Gly | Leu | Arg | Pro Aib | Cys Lys |
| stromelysin cleavage sites of stromelysin-1d | Asp | Asp Aib Pro | Val Aib Pro | Gly | His | Phe | Arg | Pro Aib | Cys Lys |
| stromelysin cleavage sites of stromelysin-1 | Asp | Asp Aib Pro | Thr Aib Pro | Leu | Glu | Val | Met Nle | Pro Aib | Cys Lys |
| stromelysin cleavage site of proteoglycan link protein | Asp | Arg Aib Pro | Ala Aib Pro | Ile | His | Ile | Gln | Pro Aib | Cys Lys |
| gelatinase type IV collagenase site of 72 K gelatinases | Asp | Asp Aib Pro | Val Aib Pro | Ala | Asn | Tyr | Asn | Pro Aib | Cys Lys |
| gelatinase type IV cleavage of gelatin | Asp | Gly Aib Pro | Pro Aib | Ala | Gly | Glu | Arg | Pro Aib | Cys Lys |
| gelatinase type IV cleavage of gelatin | Asp | Gly Aib Pro | Pro Aib | Ala | Gly | Phe | Ala | Pro Aib | Cys Lys |
| type III collagen (human skin) | Asp | Gly Aib Pro | Pro Aib | Gln | Gly | Leu | Ala | Pro Aib | Cys Lys |
| Human FIB-CL propeptide | Asp | Asp Aib Pro | Val Aib Pro | Ala | Gln | Phe | Val | Pro Aib | Cys Lys |
| Cathepsin D (Thyroglobulin Fragment Tg1) | Asp | Asp Aib Pro | Gly Pro Aib | His | Phe | Leu | Arg | Pro Aib | Cys Lys |
| Cathepsin D (Thyroglobulin Fragment Tg2) | Asp | Thr Aib Pro | Thr Pro Aib | Glu | Leu | Phe | Ser | Pro Aib | Cys Lys |
| Cathepsin D (Thyroglobulin Fragment Tg3) | Asp | Lys Aib Pro | Phe Pro Aib | leu | Ala | Phe | Leu | Pro Aib | Cys Lys |
| Cathepsin D (Thyroglobulin Fragment Tg4) | Asp | Phe Aib Pro | Ser Pro Aib | His | Phe | Val | Arg | Pro Aib | Cys Lys |
| Prostate Specific | Asp | Gln | Gln | Leu | Leu | His | Asn | Pro | Cys |

TABLE 2-continued

Illustration of the design of the conformation determining regions and protease binding site based on known protease substrate and inhibitor sequences. Italics indicate residues that are added to create a bend and to increase rigidity of the conformation determining regions. Normal font indicates residues of the substrate or inhibitor that forms the protease binding site. The thick line indicates the location at which the protease binding site is cleaved.

| Substrate/Inhibitor | CDR ($C^1$) | | | Protease Binding Site (P) | | | | CDR ($C^2$) | |
|---|---|---|---|---|---|---|---|---|---|
| | $C^1_5$ | $C^1_4$ | $C^1_3$ | $P_2$ | $P_1$ | $P_1'$ | $P_2'$ | $C^2_3$ | $C^2_4$ |
| Prostate Specific Antigen (PSA) (Seminolgelin, Sg) Sg1 | | Aib *Pro* | *Pro* Aib | | | | | Aib | Lys |
| Prostate Specific Antigen (PSA) (Seminolgelin, Sg) Sg2 | Asp | Ser *Aib Pro* | Ile *Pro Aib* | Gln | Tyr | Thr | Tyr | Pro *Aib* | Cys Lys |
| Prostate Specific Antigen (PSA) (Seminolgelin, Sg) Sg3 | Asp | Ser *Aib Pro* | Ser *Pro Aib* | Gln | Tyr | Ser | Asn | Pro *Aib* | Cys Lys |
| Prostate Specific Antigen (PSA) (Seminolgelin, Sg) Sg4 | Asp | Ser *Aib Pro* | Ser *Pro Aib* | Ile | Tyr | Ser | Gln | Pro *Aib* | Cys Lys |
| Gelatin α1 (type 1) | Asp | Gly *Aib Pro* | Pro *Aib* | Ala | Gly | Val | Gln | Pro *Aib* | Cys Lys |

[1] In a preferred embodiment, the sequence may be followed by an $S_2$ spacer of Gly-Tyr. Thus, for example, where $C^2_4$ is Lys, $C^2_4$-$S_2$ is Lys-Gly-Tyr.

B) Indicators Having Other Binding Sites.

In another preferred embodiment, the binding site (P) ranges from 2 to about 12 amino acids in length. It was a discovery of this invention, that somewhat larger conformation determining regions can sufficiently restrict the degrees of freedom of the indicator molecule, that the fluorophores are suitably quenched regardless of the amino acid sequence of the binding (recognition) domain (P). In one preferred embodiment, these compositions are include the compounds represented by the Formula V:

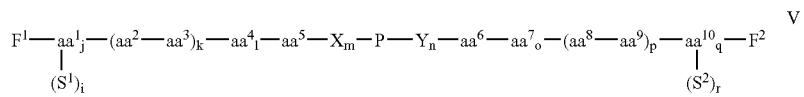

In this formula, P is a peptide comprising a protease binding site and consists of 2 to about 12 amino acids, $F^1$ and $F^2$ are fluorophores where $F^1$ is attached to the amino terminal amino acid and $F^2$ is attached to the carboxyl terminal amino acid of the composition (excluding spacers). $S^1$ and $S^1$, when present, are peptide spacers ranging in length from 1 to about 50 amino acids and $S^1$, when present, is attached to the amino terminal amino acid, while $S^2$, when present, is attached to the carboxyl terminal amino acid. The subscripts i, j, k, l, m, n, o, p, q, and r are independently 0 or 1.

In a particularly preferred embodiment, $aa^1$ and $aa^{10}$ are independently selected from the group consisting of lysine, ornithine and cysteine; $aa^2$, $aa^3$, $aa^8$ and $aa^9$ are independently selected from the group consisting of an amino acid or a dipeptide consisting of Asp, Glu, Lys, Omithine, Arg, Citrulline, homocitrulline, Ser, homoserine, Thr, and Tyr; $aa^5$, $aa^4$, $aa^6$, and $aa^7$ are independently selected from the group consisting of proline, 3,4-dehydroproline, hydroxyproline, alpha aminoisobutyric acid and N-methyl alanine; X is selected from the group consisting of Gly, βAla, γAbu, Gly-Gly, Ahx, βAla-Gly, βAla-βAla, γAbu-Gly, βAla-γAbu, Gly-Gly-Gly, γAbu-γAbu, Ahx-Gly, βAla-Gly-Gly, Ahx-βAla, βAla-βAla-Gly, Gly-Gly-Gly-Gly, Ahx-γAbu, βAla-βAla-βAla, γAbu-βAla-Gly, γAbu-γAbu-Gly, Ahx-Ahx, γAbu-γAbu-βAla, and Ahx-Ahx-Gly; Y is selected from the group consisting of Gly, βAla, γAbu, Gly-Gly, Ahx, Gly-βAla, βAla-βAla, Gly-γAbu, γAbu-βAla, Gly-Gly-Gly, γAbu-γAbu, Gly-Ahx, Gly-Gly-βAla, βAla-Ahx, Gly-βAla-βAla, Gly-Gly-Gly-Gly (SEQ ID NO: 211), γAbu-Ahx, βAla-βAla-βAla, Gly-βAla-γAbu, Gly-γAbu-γAbu, Ahx-Ahx, βAla-γAbu-γAbu, and Gly-Ahx-Ahx.

When i is i, $S^1$ is joined to $aa^1$ by a peptide bond through a terminal alpha amino group of $aa^1$; and when r is 1, $S^2$ is joined to $aa^{10}$ by a peptide bond through a terminal alpha carboxyl group of $aa^{10}$. It will be appreciated that amino acids 1-4 or 7-10 may be absent. When one or more of these amino acids are absent, the fluorophores are attached to the remaining terminal amino acids.

The amino acid backbones of such particularly preferred compositions are listed in Tables 3 and 4.

TABLE 3

Illustration of the design of the conformation determining regions and protease binding sites in molecules having P domains larger that 4 am TABLE 4-continued Illustration of the design of the conformation determining regions and protease binding sites in molecules having P domains larger that 4 amino acids. The P1 residue is underlined. Z is benzyloxycarbonyl group, K[TFA] means Lys(N(epsilon)trifluoroacetyl), Fm is Fmoc (preferably attached to the alpha amino group of the amino terminal residue e.g., Lysine (K). O indicates tetrahydroisoquinoline-3-carboxylic acid. Aib, designated as B, can be replaced by Pro. J is epsilon-aminocaproic acid

| Substr. class | $aa^1$ | $aa^2$-$aa^3$ | $aa^4$ | $aa^5$ | X | P | Y | $aa^6$ | $aa^7$ | $aa^8$-$aa^9$ | $aa^{10}$ | $S^2$ | SEQ ID NO |
|---|---|---|---|---|---|---|---|---|---|---|---|---|---|
| | K | D | | B | G | YVANGIN | G | | | | P | K | GY | 48 |
| | K | D | | B | JG | YVADGID | GJ | | | | P | K | GY | 49 |
| | K | D | | B | JG | YVANGID | GJ | | | | P | K | GY | 50 |
| | K | D | | B | JG | YVANGIN | GJ | | | | P | K | GY | 51 |
| | K | D | | B | JG | YVADGIN | GJ | | | | P | K | GY | 52 |
| | K | D | | B | JG | dYVADGIN | GJ | | | | P | K | GY | 53 |
| | K | D | | B | | YVHDAPV | | | | | P | K | GY | 54 |
| | K | D | | B | | YVHDAPV | | | | | P | K | GY | 55 |
| | K | D | | B | | YVHDAPV | | | | | P | K | GY | 56 |
| | K | D | | B | G | YVHDAPV | G | | | | P | K | GY | 57 |
| | K | D | | B | G | YVHDAPV | G | | | | P | K | GY | 58 |
| | K | D | | B | G | YVHDAPV | G | | | | P | K | GY | 59 |
| | K | D | | B | JG | YVHDAPV | G | | | | P | K | GY | 60 |
| | K | D | | B | JG | YVHDAPV | G | | | | P | K | GY | 61 |
| | K | D | | B | JG | YVHDAPV | G | | | | P | K | GY | 62 |
| | K | D | | B | JG | YVHDAPV | G | | | | P | K | GY | 63 |
| | K | D | | B | JG | YVHDAPV | G | | | | P | K | GY | 64 |
| | K | D | | B | JG | dYVHDAPV | G | | | | P | K | GY | 65 |
| LAMIN-A | Fm-K | D | | P | JG | LVEIDNG | J | | | | P | K | GY | 66 |
| | FM-K | DP | | | JG | LVEIENG | J | | | | P | K | GY | 67 |
| | K | D | | B | | LVEIDNG | | | | | P | K | GY | 68 |
| | K | D | | B | G | LVEIDNG | G | | | | P | K | GY | 69 |
| | K | D | | B | JG | LVEIDNG | GJ | | | | P | K | GY | 70 |
| | K | D | | B | JG | LVEINNG | GJ | | | | P | K | GY | 71 |
| ProCPP32-Asp175 | Fm-K | D | | P | J | GIETESGV | GJ | | | | P | K | GY | 72 |
| | Fm-K | D | | P | J | GIETDSG | J | | | | P | K | GY | 73 |
| | Fm-K | D | | P | J | GIETESG | J | | | | P | K | GY | 74 |
| | K | D | | B | | GIETDSGVDD | | | | | P | K | GY | 75 |
| | K | D | | B | | GIETNSGVDD | | | | | P | K | GY | 76 |
| | K | D | | B | G | GIETDSGVDD | G | | | | P | K | GY | 77 |
| | K | D | | B | G | GIETNSGV | G | | | | P | K | GY | 78 |
| | K | D | | B | J | GIETDSGV | J | | | | P | K | GY | 79 |
| | K | D | | B | J | GIETNSGV | J | | | | P | K | GY | 80 |
| | K | D | | B | JG | GIETDSGV | GJ | | | | P | K | GY | 81 |
| | K | D | | B | JG | GIETNSGV | GJ | | | | P | K | GY | 82 |
| ProCPP32-Asp28 | K | D | | B | | GSESMDSGISLD | | | | | P | K | GY | 83 |
| | K | D | | B | G | GSESMDSG | G | | | | P | K | GY | 84 |
| | K | D | | B | JG | GSESMDSG | GJ | | | | P | K | GY | 85 |
| NS3 NS5A/5B | K | D | | B | JG | DVVCCSMS | GJ | | | | P | K | GY | 86 |
| | K | D | | B | JG | DVVCDSMS | GJ | | | | P | K | GY | 87 |
| | K | D | | B | JG | DVVCCSdMS | GJ | | | | P | K | GY | 88 |
| | K | D | | B | JG | DVVCDSdMS | GJ | | | | P | K | GY | 89 |
| | K | D | | B | JG | DVVCCPdMS | GJ | | | | P | K | GY | 90 |
| | K | D | | B | JG | EDVVCCS | GJ | | | | P | K | GY | 91 |
| | K | D | | B | JG | EDVVCDS | GJ | | | | P | K | GY | 92 |
| | K | D | | B | JG | EDdVVCCP | GJ | | | | P | K | GY | 93 |
| | K | D | | B | JG | EDdVVCDP | GJ | | | | P | K | GY | 94 |
| | K | D | | B | JG | DdVVCCSdMS | GJ | | | | P | K | GY | 95 |
| | K | D | | B | JG | DVdVCDSdMS | GJ | | | | P | K | GY | 96 |
| | K | D | | B | JG | DdVVCCPdMS | GJ | | | | P | K | GY | 97 |
| | K | D | | B | JG | DVVCCSM | GJ | | | | P | K | GY | 98 |
| | K | D | | B | JG | DVVCDSM | GJ | | | | P | K | GY | 99 |
| | K | D | | B | JG | VCCSM | GJ | | | | P | K | GY | 100 |
| | K | D | | B | JG | VCDSM | GJ | | | | P | K | GY | 101 |
| NS3 NS4A/4B | K | D | | B | JG | DEMEECSQHL | | | | | P | K | GY | 102 |
| | K | D | | B | JG | DEMEECPQHL | | | | | P | K | GY | 103 |
| | K | D | | B | JG | DEMEEDSQHL | | | | | P | K | GY | 104 |
| | K | D | | B | JG | EMEECSQHL | | | | | P | K | GY | 105 |
| | K | D | | B | JG | EMEECPQHL | | | | | P | K | GY | 106 |
| | K | D | | B | JG | EMEEDSQHL | | | | | P | K | GY | 107 |
| | K | D | | B | JG | EMEECSQHL | G | | | | P | K | GY | 108 |
| | K | D | | B | JG | EMEECPQHL | G | | | | P | K | GY | 109 |
| | K | D | | B | JG | EMEEDSQHL | G | | | | P | K | GY | 110 |
| | K | D | | B | JG | EMEECSQHL | GJ | | | | P | K | GY | 111 |
| | K | D | | B | JG | EMEECPQHL | GJ | | | | P | K | GY | 112 |
| | K | D | | B | JG | EMEEDSQHL | GJ | | | | P | K | GY | 113 |

TABLE 4-continued

Illustration of the design of the conformation determining regions and protease binding sites in molecules having P domains larger that 4 amino acids. The P1 residue is underlined. Z is benzyloxycarbonyl group, K[TFA] means Lys(N(epsilon)trifluoroacetyl), Fm is Fmoc (preferably attached to the alpha amino group of the amino terminal residue e.g., Lysine (K). O indicates tetrahydroisoquinoline-3-carboxylic acid. Aib, designated as B, can be replaced by Pro. J is epsilon-aminocaproic acid

| Substr. class | aa¹ | aa²-aa³ | aa⁴ | aa⁵ | X | P | Y | aa⁶ | aa⁷ | aa⁸-aa⁹ | aa¹⁰ | S² | SEQ ID NO |
|---|---|---|---|---|---|---|---|---|---|---|---|---|---|
| Ext. PAI-2 | K | D |  | B | JG | VMTG<u>R</u>TG | J | P |  |  | K | GY | 114 |
|  | K | D |  | B | JG | VdMTG<u>R</u>TG | J | P |  |  | K | GY | 115 |
|  | K | D |  | B | JG | VMTG<u>R</u>TG | J | P |  |  | K | GY | 116 |
|  | K | D |  | B | JG | VMTG<u>R</u>TG | J | P |  |  | K | GY | 117 |
| THROMB | K | D |  | B | JG | VMTG<u>R</u>G | J | P |  |  | K | GY | 118 |
|  | K | D |  | B | JG | VMTG<u>R</u>G | GJ | P |  |  | K | GY | 119 |
|  | K | D |  | B | JG | VdmTG<u>R</u>G | GJ | P |  |  | K | GY | 120 |
| Urokinase | Fm-K | D |  | P | J | TG<u>R</u>T |  |  |  |  |  |  | 121 |
|  |  | Fm-D |  | P |  | TG<u>R</u>T | G | P |  |  | K | GY | 122 |
|  | Fm-K | D |  | P |  | VMTG<u>R</u>T | GJ | P |  |  | K | GY | 123 |
|  | Fm-K | D |  | P |  | TG<u>R</u>T | GJ | P |  |  | K | GY | 124 |
|  | Fm-K | D |  | P | JG | TG<u>R</u>T | GJ | P |  |  | K | GY | 125 |
|  | Fm-K | D |  | P | JG | TG<u>R</u>T | G | P |  |  | K | GY | 126 |
|  | Fm-K | D |  | P | G | TG<u>R</u>T | G | P |  |  | K | GY | 127 |
|  | K | D |  | P | J | TG<u>R</u>TG | J | P |  |  | K | GY | 128 |
|  | K | D |  | P | C3 | TG<u>R</u>TG |  | P |  |  | K | GY | 129 |
|  | K | D |  | P | C7 | TG<u>R</u>TG |  | P |  |  | K | GY | 130 |
|  | K | D |  | B | JG | VMTG<u>R</u>VG | J | P |  |  | K | GY | 131 |
|  | K | D |  | B | JG | VdMTG<u>R</u>VG | J | P |  |  | K | GY | 132 |
| F12A | K | D |  | B | JG | VMTG<u>R</u>AG | J | P |  |  | K | GY | 133 |
|  | K | D |  | B | JG | VdMTG<u>R</u>AG | J | P |  |  | K | GY | 134 |
| Swedish KM/NL AMLOID | Fm-K | D |  | P | JG | SEVK<u>L</u>DAEF | GJ | P |  |  | K | GY | 135 |
|  | Fm-K | D |  | P | JG | S(d-E)VK(d-L)DAE(d-F) | GJ | P |  |  | K | GY | 136 |
|  | Fm-K | D |  | P | JG | S(d-E)VK(d-L)DAE(d-F) | GJ | P |  |  | K | GY | 137 |
|  | K | D |  | B | JG | SEVN<u>L</u>DAEF | GJ | P |  |  | K | DDY | 138 |
|  | Fm-K | D |  | B | JG | SEVN<u>L</u>DAEF | GJ | P |  |  | K | DDY | 139 |
|  | K | D |  | B | JG | SEVK<u>L</u>DAEF | GJ | P |  |  | K | DDY | 140 |
| NATIVE AMYLOID | K | D |  | B | JG | SEVK<u>M</u>DAEF | GJ | P |  |  | K | DDY | 141 |
| CATHESPSIN G | K | D |  | B | JG | SEVK<u>M</u>DDEF | GJ | P |  |  | K | DDY | 142 |
|  | K | D |  | B | JG | SEVN<u>L</u>DDEF | GJ | P |  |  | K | DDY | 143 |
| APP[709-710] | K | D |  | B | JG | GVVI<u>A</u>TVIVIT | GJ | P |  |  | K | DDY | 144 |
| APP[708-719] | K | D |  | B | JG | YGVVI<u>A</u>TVIVIT | GJ | P |  |  | K | DDY | 145 |
| APP[711-716] | K | D |  | B | JG | VI<u>A</u>TVI | GJ | P |  |  | K | DDY | 146 |
| APP[708-713] | K | D |  | B | JB | YG<u>V</u>VIA | GJ | P |  |  | K | DDY | 147 |
| PSA Sg1 | K | D |  | B | JJ | QQ<u>L</u>LHN | JJ | P |  |  | K |  | 148 |
|  | K | D |  | B | JG | QQ<u>L</u>LHN | GJ | P |  |  | K |  | 149 |
|  | K | D |  | B | G | QQ<u>L</u>LHN | G | P |  |  | K |  | 150 |
|  | K | D |  | B |  | QQ<u>L</u>LHN |  | P |  |  | K |  | 151 |
| PSA Sg2 | K | D |  | B | JJ | SIQ<u>Y</u>TY | JJ | P |  |  | K |  | 152 |
|  | K | D |  | B | JG | SIQ<u>Y</u>TY | GJ | P |  |  | K |  | 153 |
|  | K | D |  | B | G | SIQ<u>Y</u>TY | G | P |  |  | K |  | 154 |
|  | K | D |  | B |  | SIQ<u>Y</u>TY |  | P |  |  | K |  | 155 |
| PSA Sg3 | K | D |  | B | JJ | SSQ<u>Y</u>SN | JJ | P |  |  | K |  | 156 |
|  | K | D |  | B | JG | SSQ<u>Y</u>SN | GJ | P |  |  | K |  | 157 |
|  | K | D |  | B | G | SSQ<u>Y</u>SN | G | P |  |  | K |  | 158 |
|  | K | D |  | B |  | SSQ<u>Y</u>SN |  | P |  |  | K |  | 159 |
| PSA Sg4 | K | D |  | B | JJ | SSI<u>Y</u>SQ | JJ | P |  |  | K |  | 160 |
|  | K | D |  | B | JG | SSI<u>Y</u>SQ | GJ | P |  |  | K |  | 161 |
|  | K | D |  | B | G | SSI<u>Y</u>SQ | G | P |  |  | K |  | 162 |
|  | K | D |  | B |  | SSI<u>Y</u>SQ |  | P |  |  | K |  | 163 |
| Cathepsin D substrates (preferably with diethyl-rhodamine fluorophore, note fmoc (Fm) is optional) | Fm-K | D |  | P | JG | SEVN<u>L</u>DAEF | GJ | P |  |  | K | GY | 164 |
| Caspase-9 | Fm-K | D |  | P | JG | LEHDG<u>I</u>N | GJ | P |  |  | K | GY | 165 |
| Caspase-8 | Fm-K | D |  | P | JG | LETDG<u>I</u>N | GJ | P |  |  | K | GY | 166 |

TABLE 4-continued

Illustration of the design of the conformation determining regions and protease binding sites in molecules having P domains larger that 4 amino acids. The P1 residue is underlined. Z is benzyloxycarbonyl group, K[TFA] means Lys(N(epsilon)trifluoroacetyl), Fm is Fmoc (preferably attached to the alpha amino group of the amino terminal residue e.g., Lysine (K). O indicates tetrahydroisoquinoline-3-carboxylic acid. Aib, designated as B, can be replaced by Pro. J is epsilon-aminocaproic acid

| Substr. class | $aa^1$ | $aa^2$-$aa^3$ | $aa^4$ | $aa^5$ | X | P | Y | $aa^6$ | $aa^7$ | $aa^8$-$aa^9$ | $aa^{10}$ | $S^2$ | SEQ ID NO |
|---|---|---|---|---|---|---|---|---|---|---|---|---|---|
| Caspase-1 | Fm-K | D | | P | JG | WEHDGIN | GJ | P | | | K | GY | 167 |
| | Fm-K | D | | P | JG | YVHDG | J | P | | | K | GY | 168 |
| | Fm-K | D | | P | JG | YVHDGIN | GJ | P | | | K | GY | 169 |
| | Fm-K | D | | P | JG | YVHDAPV | GJ | P | | | K | GY | 170 |
| | Fm-K | D | | P | JG | YVHDAPV | GJ | P | | | K | GY | 171 |
| | Fm-K | D | | P | | YVHDAPV | GJ | P | | | K | GY | 172 |
| | Fm-K | D | | P | JG | YVHDA | GJ | P | | | K | GY | 173 |
| Granzyme B | Fm-K | DP | | | JG | IEPDS | GJ | P | | | K | GY | 174 |
| Collagenase | Fm-K | DP | | | JG | PLGIAGI | GJ | P | | | K | GY | 175 |
| HIV-1 protease | Fm-K | DP | | | JG | SQNYPIVQ | GJ | P | | | K | GY | 176 |
| Hepatitis C protease | Fa-K | DP | | | JG | EDVVCCS | GJ | P | | | K | GY | 177 |

*In certain embodiments, the Fm or Fa groups identified in the above sequences are optional or can be substituted with other hydrophobic groups. Conversely any of the sequences listed without a hydrophobic group can have one added. In addition, in certain embodiments, the carboxyl terminal amino acid can have the carboxylic acid group replaced with an amide.

IV. Fluorophores

A fluorophore excited by incident radiation absorbs light and then subsequently re-emits that light at a different (longer) wavelength. However, in the presence of a second class of molecules, known as "acceptors" the light emitted by a so-called donor fluorophore is absorbed by the acceptor thereby quenching the fluorescence signal of the donor. Thus, use of two fluorophores, as opposed to a fluorophore/chomophore pair, allows a clearer assessment of the overlap between the emission spectrum of the donor and the excitation spectrum of the acceptor. This facilitates the design of a peptide backbone that allows optimization of the quenching. This results in a high efficiency donor/acceptor pair facilitating the detection of low concentrations of protease activity. Thus, although a fluorophore/chromophore combination can be suitable, in certain preferred embodiments, the fluorogenic protease inhibitors of this invention will comprise two fluorophores.

The "donor" and "acceptor" molecules are typically selected as a matched pair such that the absorption spectrum of the acceptor molecule overlaps the emission spectrum of the donor molecule as much as possible. In addition, the donor and acceptor fluorophores are preferably selected such that both the absorption and the emission spectrum of the donor molecule are in the visible range (400 nm to about 700 nm). The fluorophores thereby provide a signal that is detectable in a biological sample thus facilitating the detection of all protease activity in biological fluids, tissue homogenates, in situ in tissue sections, cultured or freshly isolated cells, and the like. The emission spectra, absorption spectra and chemical composition of many fluorophores are well known to those of skill in the art (see, for example, *Handbook of Fluorescent Probes and Research Chemicals*, R. P. Haugland, ed. which is incorporated herein by reference).

Preferred fluorophore pairs include, but are not limited to the rhodamine derivatives. Thus, for example 5- and/or 6-carboxytetramethylrhodamine or the succinimidyl ester of 5- and/or 6-carboxytetramethylrhodamine (9-(2,5-dicarboxyphenyl)-3,6-bis-(dimethylamino)xanthylium chloride (5-TMR) and 9-(2,6-dicarboxyphenyl)-3,6-bis-(dimethylamino)xanthylium chloride (6-TMR)), (C2211 is the succinimidyl ester of 5-TMR and C1171 is the isomeric mixture of the succinimidyl esters of 5-TMR and 6-TMR respectively, available from Molecular Probes, Eugene, Oreg., USA) (Formula VI is 5-TMR) is one particularly preferred donor molecule

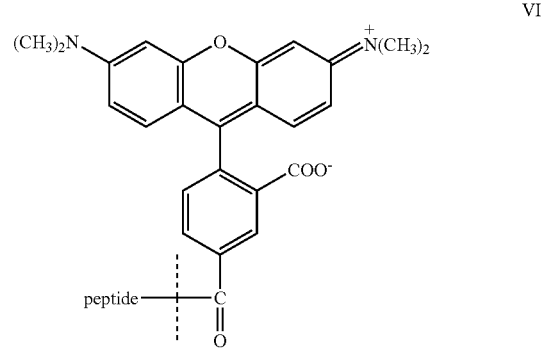

VI and carboxyrhodamine X acetamide (R 492 from Molecular Probes) (Formula VII)

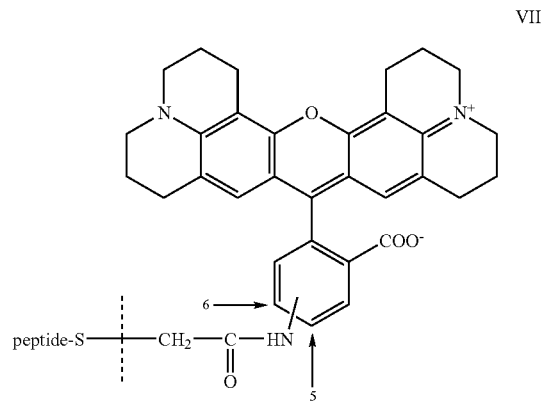

VII or the succinimidyl ester of 5- and/or 6-carboxy-X-rhodamine [9-(2,5-dicarboxyphenyl)-2,7-dimethyl-3,6-bis(ethylamino)xanthene (5-DER) and 9-(2,6-dicarboxyphenyl)-2,7-dimethyl-3,6-bis(ethylamino)xanthene (6-DER), mixed isomer available as $C^{1309}$ (designated herein as DER) from Molecular Probes] is one particularly preferred acceptor molecule. The excitation and emission of both members of this donor/acceptor pair are in the visible wavelengths, the molecules have high extinction coefficients, and the molecules have high fluorescence yields in solution. The extinction coefficient is a measure of the light absorbance at a particular wavelength by the chromophore and is therefore related to its ability to quench a signal, while the fluorescence yield is the ratio of light absorbed to light re-emitted and is a measure of the efficiency of fluorescence of the fluorophore and thus effects the sensitivity of the protease indicator.

Other preferred fluorophores include, but are not limited to rhodamine 110 (Molecular Probes), rhodamine X, 9-(2,5 (or 2,6)-dicarboxyphenyl)-3,6-bis(dimethylamino)xanthyliumhalide or other anion (TMR), 9-(2,5)-dicarboxyphenyl)-2,7-dimethyl-3,6-bis(ethylamino)xanthylium halide or other anion (Rh6G), 9-(2,6)-dicarboxyphenyl)-2,7-dimethyl-3,6-bis(ethylamino)xanthylium halide or other anion, 9-(2,5 (or 2,6)-dicarboxyphenyl)-3,6-bisamino-xanthylium halide or other anion (Rh110), 9-(2,5 (or 2,6)-dicarboxyphenyl)-3-amino-6-hydroxy-xanthylium halide or other anion (Blue Rh), 9-(2-carboxyphenyl)-2,7-dimethyl-3,6-bis(ethylamino) xanthylium, 9-(2-carboxyphenyl)-3,6-bis(dimethylamino) xanthylium, and 9-(2-carboxyphenyl)-xanthylium.

In one particularly preferred embodiment a peptide backbone will have two amino acid side chain amino groups or two sulfhydryl groups, or one amino plus one sulfhydryl group, on either side of a cleavage site available for covalent bond formation resulting from interaction with fluorophores containing succinimidyl and/or maleimidyl and/or iodoacetamidyl groups where the fluorophore to peptide ratio is ca. 3:1 in the reaction mixture enabling the product to contain 2 fluorophores per peptide backbone.

In certain embodiments, fluorophores that absorb and emit in the ultraviolet may also be used in the protease indicators of the present invention. One particularly preferred ultraviolet absorbing pair of fluorophores is 7-hydroxy-4-methylcoumarin-3-acetic acid as the donor molecule (Formula VIII)

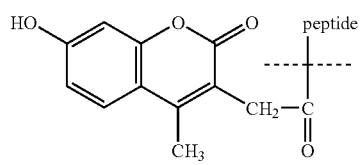

and 7-diethylamino-3-((4'-iodoacetyl)amino)phenyl)-4-methylcoumarin (Formula IX) as the acceptor molecule.

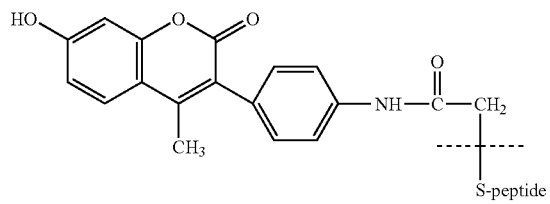

These and other fluorophores are commercially available from a large number of manufacturers such as Molecular Probes (Eugene, Oreg., USA).

It was a surprising discovery that fluorophores having matched absorption and emission spectra are not required in the practice of the present invention. In fact, a single species of fluorophore, when joined to the polypeptide backbones of this invention in the positions occupied by $F^1$ and $F^2$, is capable of quenching itself. Moreover, this quenching is fully released when the peptide backbone is cleaved.

Without being bound to a particular theory, it is believed that quenching is accomplished by the formation of ground state dimers wherein the fluorescence of the dimer is largely quenched. It is the limited conformational entropy of the peptide backbones of this invention that forces fluorophores into close enough proximity to effectively form a ground state dimer.

Particularly preferred molecules form H-type dimers. The formation of H-type dimers by fluorescent molecules is described by Packard et al. (1996) Proc. Natl. Acad. Sci. USA, 93: 11640-11645; Packard et al. (1997) J. Phys. Chem. B, 101: 5070-5074. The H-type dimer is characterized by exciton bands in the absorption spectra and fluorescence quenching (see, e.g., Valdes-Aguilera et al. (1989) Acc. Chem. Res., 22: 171-177 and Packard et al. (1996) Proc. Natl. Acad. Sci. USA, 93: 11640-11645).

Thus, in a preferred embodiment, the protease indicators of this invention include only a single species of fluorophore, more preferably a fluorophore capable of forming H-type dimers.

NorFes is an undecapeptide that contains a recognition sequence and cleavage site for the serine protease elastase. When NorFes was doubly labeled with a variety of fluorophores on opposite sites of the amino acid sequence, the fluorescence was quenched due to formation of intramolecular ground-state dimers. The spectral characteristics of these dimers were predictable by exciton theory.

The decrease in dimer/monomer ratios as the temperature was raised indicated an intermolecular attraction between the dye molecules. The free energy of activation of disruption of homodimers composed of tetramethylrhodamine was at least 1.7 kcal/mole and for those of diethylrhodamine was 2.4 kcal/mnole (Packard et al. (1998) J. Phys. Chem. 102: 1820-1827). Because of the intermolecular attraction of fluorophores that form exciton dimers the connecting amino acid sequences can deviate from the optimal sequences described herein. Thus, when exciton-forming fluorophores are used, amino acid substitutions can be made in the "backbones" described herein and activity can still be maintained.

Particularly preferred exciton-forming fluorophores include, but are not limited to carboxytetramethylrhodamine, carboxyrhodamine-X, carboxyrhodamine 110, diethylaminocoumarin, and carbocyanine dyes. In this embodiment, there is no need to match emission or absorption spectra since only a single fluorophore is used. Thus a wide variety of fluorophores can be used effectively. In addition, the use of a single fluorophore greatly simplifies synthetic chemistry and simplifies detection.

Figure 4:
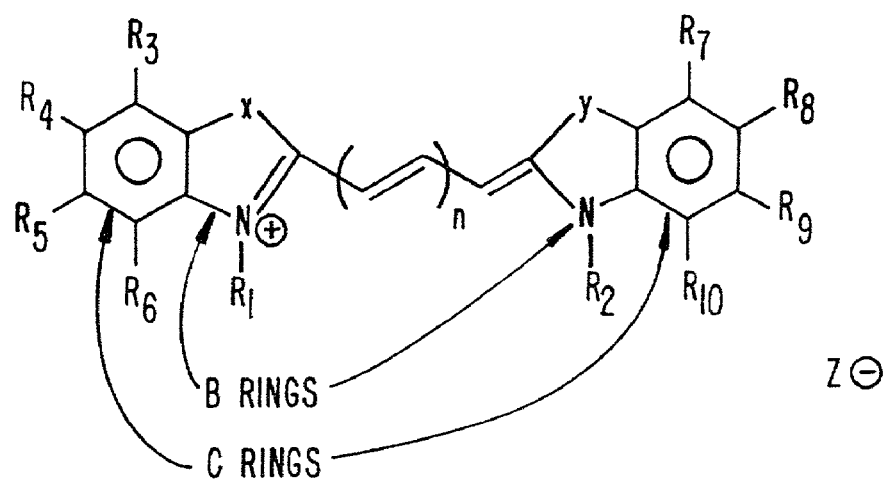
FIG. 4. Preferred dialkylated carbocyanine dyes for use in the methods of this invention. X and Y are independently selected from the group consisting of $(CH_3)_2C$, NH, O, S, and the like. N is preferably greater than or equal to zero. Preferably n is greater than zero and less than 20, more preferably N is greater than zero and less than 10, and most preferably n is greater than zero and less than about 5. In certain embodiments n is one or two. $R^1$ and $R^2$ are independently selected alkyl groups. $R^3$ through $R^{10}$ are independently selected from the group consisting of H, alkyl, O alkyl, alhalide, alkylated amines, amines, and the like. Z is any counterion (e.g., a halide, a perchlorate, etc.) In IC5 $R^1$ is ethyl and $R^2$ is 5-(N"-carbonylpentyl). $R^3$ through $R^{10}$ are H. X and Y are 3,3,3',3'-tetramethyl (see, e.g, IC5-OSu from Dojindo Laboratories, Inc).

The use of homo-doubly labeled indicators (indicators doubly labeled with a single species of fluorophore) of this invention also permits detection of enzymatic activity by absorbance measurements in addition to fluorescence measurements. Since blue-shifted exciton bands (or blue-shifted absorption maxima or shoulders) in absorption spectra denote H-dimer formation and fluorescence quenching is concomitant with the latter, measurement of absorption spectra may be sufficient as a diagnostic tool in the proper setting. When a doubly labeled protease indicator is cleaved by a specific protease, the H-type dimer is disrupted. The blue shifted absorption maximum, or shoulders, associated with the H-type dimer is then lost. Hence, if one measures the intensity of absorption at this blue shifted exciton band then as the H-type dimer is disrupted the absorption intensity is expected to decrease whereas the absorption intensity at the monomer maximum peak wavelength is expected to increase, i.e., the wavelength of the absorption peak is increased or the blue shoulder decreases such that the average wavelength of the band is increased Preferred for use in certain high throughput screening systems are indicators of this invention formulated with rhodamine or cyanine dyes, including cyanines and cyanine analogues. Particular preferred embodiments utilize carbocyanine dyes, more preferably dialkylated carbocyanine dyes, e.g. as illustrated in FIG. 4. Suitable cyanine dyes include, but are not limited to N-ethyl-N'-[5-(N"-succinimidyloxycarbonyl)pentyl]indocarbocyanine chloride, and N-ethyl-N'-[5-(N"-carbonyl)pentyl]-3,3,3',3-tetramethyl-2,2'-indodicarbocyanine chloride.

V. Preparation of Fluorogenic Protease Indicators

The fluorogenic protease indicators of the present invention are preferably prepared by first synthesizing the peptide backbone, i.e. the protease cleavage site (P), the two conformation determining regions ($C^1$ and $C^2$), and the spacers ($S^1$ and $S^2$) if present. The fluorophores are then chemically conjugated to the peptide. The fluorophores are preferably conjugated directly to the peptide however, they may also be coupled to the peptide through a linker. Finally, where the fluorogenic protease indicator is to be bound to a solid support, it is then chemically conjugated to the solid support via the spacer ($S^1$ or $S^2$) either directly or through a linker.

A) Preparation of the Peptide Backbone

Solid phase peptide synthesis in which the C-terminal amino acid of the sequence is attached to an insoluble support followed by sequential addition of the remaining amino acids in the sequence is the preferred method for preparing the peptide backbone of the compounds of the present invention. Techniques for solid phase synthesis are described by Barany and Merrifield, *Solid-Phase Peptide Synthesis*; pp. 3-284 in *The Peptides: Analysis, Synthesis, Biology. Vol. 2: Special Methods in Peptide Synthesis, Part a.*, Merrifield, et al *J. Am. Chem. Soc.* 85, 2149-2156 (1963), and Gross and Meienhofer, eds. Academic press, N.Y., 1980 and Stewart et al., *Solid Phase Peptide Synthesis*, 2nd ed. Pierce Chem. Co., Rockford, Ill. (1984) which are incorporated herein by reference. Solid phase synthesis is most easily accomplished with commercially available peptide synthesizers utilizing FMOC or TBOC chemistry. The chemical synthesis of the peptide component of a fluorogenic protease indicator is described in detail in Examples 1 and 2.

In a particularly preferred embodiment, peptide synthesis is performed using Fmoc synthesis chemistry. The side chains of Asp, Ser, Thr and Tyr are preferably protected using t-Butyl and the side chain of Cys residue using S-trityl and S-t-butylthio, and Lys residues are preferably protected using t-Boc, Fmoc and 4-methyltrityl for lysine residues. Appropriately protected amino acid reagents are commercially available. The use of multiple protecting groups allows selective deblocking and coupling of a fluorophore to any particular desired side chain. Thus, for example, t-Boc deprotection is accomplished using TFA in dichloromethane, Fmoc deprotection is accomplished using 20% (v/v) piperidine in DMF or N-methylpyrolidone, and 4-methyltrityl deprotection is accomplished using 1 to 5% (v/v) TFA in water or 1% TFA and 5% triisopropylsilane in DCM, S-t-butylthio deprotection is accomplished in aqueous mercaptoethanol (10%), t-butyl and t-boc and S-trityl deprotection is accomplished using TFA:phenol: water: thioanisol: ethanedithiol (85:5:5:2.5:2.5), and t-butyl and t-Boc deprotection is accomplished using TFA:phenol: water (95: 5:5). Detailed synthesis, deprotection and fluorophore coupling protocols are provided in Examples 1 and 2.

Alternatively, the peptide components of the fluorogenic protease indicators of the present invention may be synthesized utilizing recombinant DNA technology. Briefly, a DNA molecule encoding the desired amino acid sequence is synthesized chemically by a variety of methods known to those of skill in the art including the solid phase phosphoramidite method described by Beaucage and Carruthers, *Tetra. Letts.* 22: 1859-1862 (1981), the triester method according to Matteucci, et al., *J. Am. Chem. Soc.*, 103:3185 (1981), both incorporated herein by reference, or by other methods known to those of skill in the art. It is preferred that the DNA be synthesized using standard β-cyanoethyl phosphoramidites on a commercially available DNA synthesizer using standard protocols.

The oligonucleotides may be purified, if necessary, by techniques well known to those of skill in the art. Typical purification methods include, but are not limited to gel electrophoresis, anion exchange chromatography (e.g. Mono-Q column, Pharmacia-LKB, Piscataway, N.J., USA), or reverse phase high performance liquid chromatography (HPLC). Method of protein and peptide purification are well known to those of skill in the art. For a review of standard techniques see, *Methods in Enzymology Volume 182: Guide to Protein Purification*, M. Deutscher, ed. (1990), pages 619-626, which are incorporated herein by reference.

The oligonucleotides may be converted into double stranded DNA either by annealing with a complementary oligonucleotide or by polymerization with a DNA polymerase. The DNA may then be inserted into a vector under the control of a promoter and used to transform a host cell so that the cell expresses the encoded peptide sequence. Methods of cloning and expression of peptides are well known to those of skill in the art. See, for example, Sambrook, et al., *Molecular Cloning: a Laboratory Manual* (2nd Ed., Vols. 1-3, Cold Spring Harbor Laboratory (1989)), *Methods in Enzymology*, Vol. 152: *Guide to Molecular Cloning Techniques* (Berger and Kimmel (eds.), San Diego: Academic Press, Inc. (1987)), or *Current Protocols in Molecular Biology*, (Ausubel, et al. (eds.), Greene Publishing and Wiley-Interscience, New York (1987), which are incorporated herein by reference.

B) Linkage of the Fluorophores to the Peptide Backbone

The fluorophores are linked to the peptide backbone by any of a number of means well known to those of skill in the art. In a preferred embodiment, the fluorophore is linked directly from a reactive site on the fluorophore to a reactive group on the peptide such as a terminal amino or carboxyl group, or to a reactive group on an amino acid side chain such as a sulfur, an amino, a hydroxyl, or a carboxyl moiety. Many fluorophores normally contain suitable reactive sites. Alternatively, the fluorophores may be derivatized to provide reactive sites for linkage to another molecule. Fluorophores derivatized with functional groups for coupling to a second molecule are commercially available from a variety of manufacturers. The derivatization may be by a simple substitution of a group on the fluorophore itself, or may be by conjugation to a linker. Various linkers are well known to those of skill in the art and are discussed below. The fluorophores may also be covalently linked to the peptide prior to its cleavage off of the solid support.

As indicated above, in a preferred embodiment, the fluorophores are directly linked to the peptide backbone of the protease indicator. Thus, for example, the 5'-carboxytetramethylrhodamine (5-TMR) fluorophore may be linked to aspartic acid via the alpha amino group of the amino acid as shown in Formula V. The iodoacetamide group of rhodamine X acetamide (R492)) may be linked by reaction with the sulfhydryl group of a cysteine as indicated in formula VI. Means of performing such couplings are well known to those of skill in the art, and the details of one such coupling are provided in Example 1.

One of skill in the art will appreciate that when the peptide spacers ($S^1$ or $S^2$) are present (as is discussed below), the fluorophores are preferably linked to the conformation determining regions through a reactive group on the side chain of the terminal amino acid of $C^1$ or $C^2$ as the spacers themselves form a peptide linkage with the terminal amino and carboxyl groups of $C^1$ or $C^2$ respectively.

C) Selection of Spacer Peptides and Linkage to a Solid Support

The fluorogenic protease indicators of the present invention may be obtained in solution or linked to a solid support. A "solid support" refers to any solid material that does not dissolve in or react with any of the components present in the solutions utilized for assaying for protease activity using the fluorogenic protease indicator molecules of the present invention and that provides a functional group for attachment of the fluorogenic molecule. Solid support materials are well known to those of skill in the art and include, but are not limited to silica, controlled pore glass (CPG), polystyrene, polystyrene/latex, carboxyl modified teflon, dextran, derivatized polysaccharides such as agar bearing amino, carboxyl or sulfhydryl groups, various plastics such as polyethylene, acrylic, and the like. Also of use are "semisolid" supports such as lipid membranes as found in cells and in liposomes. One of skill will appreciate that the solid supports may be derivatized with functional groups (e.g. hydroxyls, amines, carboxyls, esters, and sulfhydryls) to provide reactive sites for the attachment of linkers or the direct attachment of the peptide.

The fluorogenic protease indicators may be linked to a solid support directly through the fluorophores or through the peptide backbone comprising the indicator. Linkage through the peptide backbone is most preferred.

When it is desired to link the indicator to a solid support through the peptide backbone, the peptide backbone may comprise an additional peptide spacer (designated $S^1$ or $S^2$ in Formula I). The spacer may be present at either the amino or carboxyl terminus of the peptide backbone and may vary from about 1 to about 50 amino acids, more preferably from 1 to about 20 and most preferably from 1 to about 10 amino acids in length. Particularly preferred spacers include Asp-Gly-Ser-Gly-Gly-Gly-Glu-Asp-Glu-Lys (SEQ ID NO: 178), Lys-Glu-Asp-Gly-Gly-Asp-Lys (SEQ ID NO: 179), Asp-Gly-Ser-Gly-Glu-Asp-Glu-Lys (SEQ ID NO: 180), and Lys-Glu-Asp-Glu-Gly-Ser-Gly-Asp-Lys (SEQ ID NO: 181).

The amino acid composition of the peptide spacer is not critical as the spacer just serves to separate the active components of the molecule from the substrate thereby preventing undesired interactions. However, the amino acid composition of the spacer may be selected to provide amino acids (e.g. a cysteine or a lysine) having side chains to which a linker or the solid support itself, is easily coupled. Alternatively the linker or the solid support itself may be attached to the amino terminus of $S^1$ or the carboxyl terminus of $S^2$.

In a preferred embodiment, the peptide spacer is actually joined to the solid support by a linker. The term "linker", as used herein, refers to a molecule that may be used to link a peptide to another molecule, (e.g. a solid support, fluorophore, etc.). a linker is a hetero or homobifunctional molecule that provides a first reactive site capable of forming a covalent linkage with the peptide and a second reactive site capable of forming a covalent linkage with a reactive group on the solid support. The covalent linkage with the peptide (spacer) may be via either the terminal carboxyl or amino groups or with reactive groups on the amino acid side-chain (e.g. through a disulfide linkage to a cysteine).

Suitable linkers are well known to those of skill in the art and include, but are not limited to, straight or branched-chain carbon linkers, heterocyclic carbon linkers, or peptide linkers. As indicated above, the linkers may be joined to the carboxyl and amino terminal amino acids through their terminal carboxyl or amino groups or through their reactive side-chain groups.

Particularly preferred linkers are capable of forming covalent bonds to amino groups, carboxyl groups, or sulfhydryl. Amino-binding linkers include reactive groups such as carboxyl groups, isocyanates, isothiocyanates, esters, haloalkyls, and the like. Carboxyl-binding linkers are capable of forming include reactive groups such as various amines, hydroxyls and the like. Finally, sulfhydryl-binding linkers include reactive groups such as sulfhydryl groups, acrylates, isothiocyanates, isocyanates and the like. Particularly preferred linkers include sulfoMBS (m-maleimidobenzoyl-N-hydroxysulfosuccinimide ester) for linking amino groups (e.g. an amino group found on a lysine residue in the peptide) with sulfhydryl groups found on the solid support, or vice versa, for linking sulfhydryl groups (e.g. found on a cysteine residue of the peptide) with amino groups found on the solid support. Other particularly preferred linkers include EDC (1-ethyl-3-(3-dimethylaminopropryl)-carbodiimide) and bis-(sulfosuccinimidyl suberate). Other suitable linkers are well known to those of skill in the art.

The fluorogenic compounds of the present invention may be linked to the solid support through either the $S^1$ or the $S^2$ spacer such that the donor fluorophore is either retained on the solid support after cleavage of the molecule by a protease or such that the donor fluorophore goes into solution after cleavage. In the former case, the substrate is then assayed for fluorescence to detect protease activity, while in the later case the solution is assayed for fluorescence to detect protease activity.

VI. Detection of Protease Activity

The present invention also provides methods for utilizing the fluorogenic protease indicators to detect protease activity in a variety of contexts. Thus, in one embodiment, the present invention provides for a method of using the fluorogenic indicators to verify or quantify the protease activity of a stock solution of a protease used for experimental or industrial purposes. Verification of protease activity of stock protease solutions before use is generally recommended as proteases often lose activity over time (e.g. through self-hydrolysis) or to show varying degrees of activation when activated from zymogen precursors.

Assaying for protease activity of a stock solution simply requires adding a quantity of the stock solution to a fluorogenic protease indicator of the present invention and measuring the subsequent increase in fluorescence or decrease in exciton band in the absorption spectrum. The stock solution and the fluorogenic indicator may also be combined and assayed in a "digestion buffer" that optimizes activity of the protease. Buffers suitable for assaying protease activity are well known to those of skill in the art. In general, a buffer will be selected whose pH corresponds to the pH optimum of the particular protease. For example, a buffer particularly suitable for assaying elastase activity consists of 50 mM sodium phosphate, 1 mM EDTA at pH 8.9. The measurement is most easily made in a fluorometer, and instrument that provides an "excitation" light source for the fluorophore and then measures the light subsequently emitted at a particular wavelength. Comparison with a control indicator solution lacking the protease provides a measure of the protease activity. The activity level may be precisely quantified by generating a standard curve for the protease/ indicator combination in which the rate of change in fluorescence produced by protease solutions of known activity is determined.

While detection of the fluorogenic compounds is preferably accomplished using a fluorometer, detection may by a variety of other methods well known to those of skill in the art. Thus for example, since the fluorophores of the present invention emit in the visible wavelengths, detection may be simply by visual inspection of fluorescence in response to excitation by a light source. Detection may also be by means of an image analysis system utilizing a video camera interfaced to a digitizer or another image acquisition system. Detection may also be by visualization through a filter as under a fluorescence microscope. The microscope may just provide a signal that is visualized by the operator. However the signal may be recorded on photographic film or using a video analysis system. The signal may also simply be quantified in real-time using either an image analysis system or simply a photometer.

Thus, for example, a basic assay for protease activity of a sample will involve suspending or dissolving the sample in a buffer (at the pH optimum of the particular protease being assayed), adding to the buffer one of the fluorogenic protease indicators of the present invention, and monitoring the resulting change in fluorescence using a spectrofluorometer. The spectrofluorometer will be set to excite the donor fluorophore at the excitation wavelength of the donor fluorophore and to detect the resulting fluorescence at the emission wavelength of the donor fluorophore.

In another embodiment, the protease activity indicators of the present invention may be utilized for detection of protease activity in biological samples. Thus, in a preferred embodiment, this invention provides for methods of detecting protease activity in isolated biological samples such as sputum, blood, blood cells, tumor biopsies, and the like, or in situ, in cells or tissues in culture, or in section where the section is embedded and unfixed. The signal may be quantified using a fluorescence microscope, a fluorescence microplate reader, a fluorometer, or a flow cytometer.

A) Ex Vivo Assays of Isolated Biological Samples

In one embodiment, the present invention provides for methods of detecting protease activity in a biological sample. This may be determined by simply contacting the sample with a fluorogenic protease indicator of the present invention and monitoring the change in fluorescence of the indicator over time. The sample may be suspended in a "digestion buffer" as described above. The sample may also be cleared of cellular debris, e.g. by centrifugation before analysis.

Where the fluorogenic protease indicator is bound to a solid support the assay may involve contacting the solid support bearing the indicator to the sample solution. Where the indicator is joined to the solid support by the side of the molecule bearing the donor fluorophore, the fluorescence of the support resulting from digestion of the indicator will then be monitored over time by any of the means described above. Conversely, where the acceptor molecule fluorophore is bound to a solid support, the test solution may be passed over the solid support and then the resulting luminescence of the test solution (due to the cleaved fluorophore) is measured. The donor and acceptor pair may be substituted with the same fluorophore on both the solid support and in the solution. This latter approach may be particularly suitable for high throughput automated assays.

B) In Situ Assays of Histological Sections.

In another embodiment, this invention provides for a method of detecting in situ protease activity in histological sections. This method of detecting protease activity in tissues offers significant advantages over prior art methods (e.g. specific stains, antibody labels, etc.) because, unlike simple labeling approaches, in situ assays using the protease indicators indicate actual activity rather than simple presence or absence of the protease. Proteases are often present in tissues in their inactive precursor (zymogen) forms which are capable of binding protease labels. Thus traditional labeling approaches provide no information regarding the physiological state, vis a vis protease activity, of the tissue.

The in situ assay method generally comprises providing a tissue section (preferably a frozen section), contacting the section with one of the fluorogenic protease indicators of the present invention, and visualizing the resulting fluorescence. Visualization is preferably accomplished utilizing a fluorescence microscope. The fluorescence microscope provides an "excitation" light source to induce fluorescence of the "donor" fluorophore. The microscope is typically equipped with filters to optimize detection of the resulting fluorescence. Thus, for example, for the fluorogenic protease indicators described in Example 1, a typical filter cube for a Nikon microscope would contain an excitation filter ($\lambda$=550±12 nm), a dichroic mirror ($\lambda$=580 nm) and an interference-emission filter ($\lambda$=580±10 nm). As indicated above, the microscope may be equipped with a camera, photometer, or image acquisition system.

The sections are preferably cut as frozen sections as fixation or embedding will destroy protease activity in the sample.

The fluorogenic indicator may be introduced to the sections in a number of ways. For example, the fluorogenic protease indicator may be provided in a buffer solution, as described above, which is applied to the tissue section. Alternatively, the fluorogenic protease indicator may be provided as a semi-solid medium such as a gel or agar which is spread over the tissue sample. The gel helps to hold moisture in the sample while providing a signal in response to protease activity. The fluorogenic protease indicator may also be provided conjugated to a polymer such as a plastic film which may be used in procedures similar to the development of Western Blots. The plastic film is placed over the tissue sample on the slide and the fluorescence resulting from cleaved indicator molecules is viewed in the sample tissue under a microscope.

Typically, the tissue sample must be incubated for a period of time to allow the endogenous proteases to cleave the fluorogenic protease indicators. Incubation times will range from about 10 to 60 minutes at temperatures up to and including 37° C.

C) In Situ Assays of Cells in Culture and Cell Suspensions Derived From Tissues and Biopsy Samples.

In yet another embodiment, this invention provides for a method of detecting in situ protease activity of cells in culture, cell suspensions, or adherent cell layers where the cells are derived from one or more biological samples (e.g. derived from tissues, biopsy samples, or biological fluids such as saliva, blood, urine, lymph, plasma, etc.). In preferred embodiments, the cultured cells are grown either in suspension or adherent culture and can be to histology slides for visualization, e.g., by cytocentrifugation.

In one preferred embodiment, slide preparations are washed with phosphate buffered saline and coated with a semi-solid polymer or a solution containing the fluorogenic protease indicator. The slide is incubated at 37° C. for the time necessary for the endogenous proteases to cleave the protease indicator. The slide is then examined, e.g., under a fluorescence microscope equipped with the appropriate filters as described above.

In another preferred embodiment, the cells are incubated with the protease indications at 37° C., then washed with buffer and transferred to a glass capillary tube and examined under a fluorescence microscope or viewed directly (without washing) by fluorescence microscopy. When a flow cytometer is used to quantitate the intracellular enzyme activity, the cells with the fluorogenic indicator can be simply diluted with buffer after 37° C. incubation and analyzed.

VII. Screening for Modulators of Protease Activity.

In certain preferred embodiments, this invention provides methods of screening for modulators of protease activity. A modulator of protease activity is an agent (e.g. compound) that increases, decreases, or eliminates the activity of a protease or that increases, decreases or eliminates the availability of a protease at a particular site (e.g. in a particular cell or location in a cell). The modulator of protease activity can act directly on the protease or it can act indirectly, for example, by altering availability or activity of enzymes that activate the subject protease.

In a preferred embodiment, the methods basically involve contacting the "subject" protease or a cell containing the subject protease with one or more test agents. The protease, or cell is also contacted with one or more of the indicator compounds of this invention. A difference in signal produced by the indicator compound in the presence of the test agent as compared to the signal produced where the test agent has been used as a lower concentration or where no test agent is used indicates that the test agent modulates the activity of the protease.

The assays of this invention are typically scored as positive where there is a difference between the activity seen with the test agent present or where the test agent has been previously applied, and the (usually negative) control, preferably where the difference is statistically significant (e.g. at greater than 80%, preferably greater than about 90%, more preferably greater than about 98%, and most preferably greater than about 99% confidence level). Most preferred "positive" assays show at least a 1.2 fold, preferably at least a 1.5 fold, more preferably at least a 2 fold, and most preferably at least a 4 fold or even a 10-fold difference from the negative control.

The assays can be run in vitro with the protease(s) in question and one or more indicator compounds of this invention in an appropriate buffer system. The test agent can be added to the buffer system and a change in indicator signal can be detected. In addition, or alternatively, the "test" assay can simply be compared to the same system lacking the test agent (a negative control) assay.

The assays can also be run in vivo in cells in culture, in tissues in culture, or in cells/tissues in an organism. One or more cell-permeable indicators of this invention are introduced into the subject cells. The cells, tissues, or organisms are contacted with one or more test agents and the change in indicator signal brought about by the test agent(s) are detected as described herein.

A) Test Agents.

Virtually any agent can be screened according to the methods of this invention. Such agents include, but are not limited to nucleic acids, proteins, sugars, polysaccharides, glycoproteins, lipids, and small organic molecules. The term small organic molecules typically refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al (1994) 37(9): 1233-1250).

Preparation of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487-493, Houghton et al. (1991) *Nature,* 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al, (1993) *Proc. Nat. Acad. Sci. USA* 90: 6909-6913), vinylogous polypeptides (Hagihara et al. (1992) *J. Amer. Chem. Soc.* 114: 6568), nonpeptidal peptidomimetics with a Beta-D-Glucose scaffolding (Hirschmann et al., (1992) *J. Amer. Chem. Soc.* 114: 9217-9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology,* 14(3): 309-314), and PCT/US96/10287), carbohydrate libraries (see, e.g., Liang et al. (1996) *Science,* 274: 1520-1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506, 337, benzodiazepines 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include, but are not limited to, automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist and the Venture™ platform, an ultra-high-throughput synthesizer that can run between 576 and 9,600 simultaneous reactions from start to finish (see Advanced ChemTech, Inc. Louisville, Ky.)). Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

B) High Throughput Screening

Any of the assays for protease activity and/or for modulators of protease activity, or for other cleaving activity or for modulators of other cleaving activity (e.g. glycosylase activity, nuclease activity, lipase activity, and the like) described herein are amenable to high throughput screening. Preferred assays detect alterations of a signal produced by an indicator of this invention in response to the presence of a test compound.

The assays need not screen a single test agent at a time. To the contrary, to facilitate high-throughput screening, a single assay may be run with at least two, preferably at least 5, more preferably at least 10, and most preferably at least 20 test compounds. If the assay positive, subsequent assays can be run with a subset of the test agents until the agents having the activity are identified.

C) High-Throughput Assays for Optical Signals (e.g. Fluorescence, Altered Spectra, etc.)

High throughput assays for various reporters are well known to those of skill in the art. For example, flow cytometers and multi-well fluorimeters are commercially available.

Example 11 illustrates the use of a PE Biosystems FMAT™ System 8100, automated, macro-confocal high-throughput screening (HTS) system for fluorescent, homogeneous, multiplexed, live cell- and bead-based screening assays for the assays of this invention.

VIII. Other Indicator Compositions.

As explained above, it was a discovery of this invention that fluorescent molecules covalently attached on opposite sides of a backbone (e.g., peptide cleavage site) can quench by self-interaction (e.g., through the formation of dimers). Thus, in one embodiment, indicator molecules can be made using a single fluorophore rather than a matched donor-acceptor pair. Also, as explained above, particularly preferred fluorophores are those that form H-type dimers (e.g., carboxyrhodamine 110, carboxytetramethylrhodamine, carboxyrhodamine-X, diethylaminocoumarin and carbocyanine dyes).

While, in preferred embodiments, the peptide indicators doubly labeled with a single species of flurophore, are fabricated with conformation determining regions (CDRs) according to this invention, the use of such doubly-labeled fluorophore systems is not limited to peptide substrates comprising conformation determining regions. To the contrary, homo-doubly labeled indicator systems as described herein can be used with virtually any peptide backbone providing the backbone permits "dimer" formation (reciprocal quenching) of the fluorophores. Thus, according to the methods described herein, previously known peptide backbone indicators that used fluorescence resonant energy transfer systems (FRET) (acceptor/donor) systems, can instead be designed with single fluorophores.

The use of single species labeled indicators, however, is not restricted to peptide-based compositions. To the contrary, "homo-double labeled" indicator molecules can utilize a variety of backbones including, but not limited to nucleic acid backbones, oligosaccharide backbones, lipid backbones, and the like. Methods of coupling fluorophores to such backbones are well known to those of skill in the art. For example, conjugation methods for attaching fluorophores to amino acids, peptides, proteins, nucleic acids, oligonucleotides, sugars, polysaccharides, proteoglycans, lipids, glycolipids and lipopolysaccharides, are described by Hermanson, (1995) *Bioconjugate Techniques,* Academic Press New York, N.Y., Kay M. et al., (1995) *Biochemistry,* 34: 293-300, and by Stubbs, et al. (1996) *Biochemistry* 35: 937-947.

A) Nucleic Acid Indicators.

Homo-doubly labeled nucleic acid backbones provide effective indicators for nucleic acid hybridizations and/or endonuclease activity. In this embodiment, a nucleic acid backbone is labeled with a self-quenching (e.g., H-type dimer-forming) fluorophore at the 3' and 5' end (either through a direct attachment or indirectly through (e.g., a peptide) linker). The nucleic acid backbone is selected to include self-complementary regions and thereby form a hairpin or other self-hybridized conformation that brings the fluorophores into proximity so that self-quenching occurs. When the indicator (probe) thus formed is hybridized to a complementary target nucleic acid, the self-hybridization is eliminated, the fluorophores are separated and the fluorescence signal produced by the molecule increases. Alternatively, the fluorescently labeled nucleic acid backbone can be used to assay for nuclease activity (e.g., restriction endonuclease or ribozyme activity). When the nucleic acid backbone is cleaved by a nuclease (e.g., by restriction endonuclease recognition of a target site in the backbone) the fluorophores are separated again increasing the fluorescence signal. Methods of selecting appropriate nucleic acid backbones are described by Tyagi and Kramer et al. (1996) *Nature Biotechnology*, 14: 303-308.

The homo-doubly fluorescently labeled DNA probes can be used for detection, localization, or quantification of target DNA sequences in a variety of contexts. Thus, for example, the nucleic acid indicators of this invention can be used for rapid detection of amplification products in nucleic acid amplification (e.g., PCR) reactions. Here the indicator is selected with a backbone complementary to a region of the amplification product. As amplification product is produced the indicator hybridizes to the product and the fluorescence signal activity of the PCR solution increases. The nucleic acid indicators can be used as hybridization or nuclease activity indicators in a variety of other contexts. For example, in in situ hybridization (e.g., FISH) mapping of genomic DNA sequences can be accomplished using fluorescent probes to target particular regions within chromosomes (see, e.g., Meyne (1993) *Chromosome mapping by fluorescent in situ hybridization*, pp 263-268 In: *Methods in Nonradioactive Detection* G. C. Howard, ed., Appleton & Lange, Norwalk, Conn.; Morrison (1992) *Detection of energy transfer and fluorescence quenching*, pp. 311-352 In: *Nonisotopic DNA Probes Techniques* L. J. Kricka, ed. Academic Press, New York; and Varani (1995) *Annu. Rev. Biophys. Biomol. Struct.* 24: 379-404).

In another embodiment, the self-quenching fluorophores can be used to assay two molecule interactions (e.g., protein-protein, protein-nucleic acid, ligand-receptor, etc.). In this embodiment, one fluorophore is attached to one molecule (e.g., a protein) while the second fluorophore is attached to a second molecule (e.g., a second nucleic acid or a nucleic acid binding protein). When the two molecules bind, the fluorophores are juxtaposed and quench each other (e.g., through the formation of H-type dimers). The use of donor-acceptor resonance energy transfer systems to measure two molecule interactions is described by Bannwarth et al., *Helvetica Chimica Acta*. (1991) 74: 1991-1999, Bannwarth et al. (1991), *Helvetica Chimica Acta.* 74: 2000-2007, and Bannwarth et al., European Patent Application No. 0439036A2.

B) Oligosaccharide Indicators.

Homo-doubly labeled oligosaccharide backbone indicators permit the detection of glycosidase activity and lecithin binding protein identification. The fluorophores can be conjugated directly to an oligosaccharide or glycopeptide backbone or attached indirectly through (e.g., peptide) linkers. The oligosaccharides and/or glycopeptides can be chemically synthesized, recombinantly expressed, or isolated from natural sources such as fetuin and other glycoproteins by proteolytic fragmentation of the parent glycoproteins.

As in the case for oligonucleotides, an oligosaccharide specific structure may be selected for detection of a specific glycosidase, an enzyme that hydrolyzes bonds between two sugar molecules.

When a specific oligosaccharide or lecithin is selected to look for its lecithin binding protein, then the increased fluorescence indicates the complexation events that disrupt the H-type dimer, either by separating two dyes or distorting the relative orientation of two dyes. These effects result in increased fluorescence from the homo-double labeled probe. Alternatively, complexation can be measured by quenching due to the dimerization from one fluorophore on the oligosaccharide or lecithin and the other on the binding protein.

C) Lipid Indicators

When a lipid, glycolipid or lipopolysaccharide are labeled with a self-quenching (e.g., H-type dimer forming) fluorophore and added to liposomes or other lipid (e.g., biological) membranes, a decrease in fluorescence will indicate H-type dimer formation and the degree of such fluorescence intensity will be an indication of the amount of H-type dimer formation. Because of the relative fluidity of a lipid membrane, the self-quenching fluorophores are able to interact (e.g. approach to a spacing of about 6 to about 10 Å) a stable H-type dimer results. When a membrane active agent, for example, an agent that affects either membrane fluid dynamics or permeabilization to a test compound, is added, then the observed fluorescence intensity changes indicate the test compound's ability to modify membrane fluidity or permeabilization. Hence, such labeled lipids are useful in drug screening and in development of lipid-drug delivery vehicles.

Similarly, the lipid-based probes of this invention can be used to similarly investigate the degree of lipid/protein interaction.

The technique can also be used to detect lipase activity if two parts of lipase target, e.g., phospholipid or triglyceride, are homodoubly fluorescently labeled.

IX. Cellular Uptake of Polypeptides.

It was also a discovery of this invention that attachment of a hydrophobic protecting group to a polypeptide enhances uptake of that polypeptide by a cell. The effect is most pronounced when the polypeptide also bears a fluorophore, more preferably two fluorophores (see, Example 5). In certain preferred embodiments, however, the fluorophore(s) may double as the hydrophobic group. Preferred hydrophobic groups include, but are not limited to Fmoc, 9-fluoreneacetyl group (Fa), 1-fluorenecarboxylic group, 9-florenecarboxylic group, and 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4'-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO),t-butoxymethyl (Bum), t-butoxy (tBuO), t-Butyl (tBu), Acetyl (Ac), and Trifluoroacetyl (TFA).

The hydrophobic group can be coupled to the subject (e.g. indicator or inhibitor) molecule at essentially any convenient position. In preferred embodiments, the hydrophobic group is coupled at a position such that it does not interfere with recognition/binding of the subject molecule by a cognate binding partner (e.g., a protease). In a particularly preferred embodiment, where the subject molecule is a polypeptide, the hydrophobic group is attached to a terminus. The hydrophobic group can be attached directly to the subject molecule or it can be coupled via a linker. Linkers suitable for coupling hydrophobic groups are well know to those of skill in the art.

This invention thus provides a method of delivering a molecule (e.g., a polypeptide, oligonucleotide, oligosaccharide, a lipid, etc.) into a cell. The method involves providing the molecule to be delivered (e.g., polypeptide) having attached at least two fluorophore molecules and a hydrophobic group, more preferably an Fmoc group and then contacting the cell with the molecule.

It will be appreciated that where the peptide, oligonucleotide, oligosaccharide, or lipid is to be delivered in vivo for diagnostic end point or for therapeutic purposes, fluorophores and a hydrophobic group having reduced or no toxicity are preferred. Thus, in a preferred embodiment, the fluorophores are replaced with non-toxic molecules having little or no biological activity. Preferred molecules are fused ring compounds that act as a linker joining the two ends of the molecule that is to be delivered. Particularly preferred fused ring compounds approximate the spacing of the exciton dimer.

Certain preferred fused ring compounds include, but are not limited to steroids. The relatively flat and hydrophobic fluorophores that are known for H-type dimer formation can be replaced with similarly hydrophobic and structurally rigid and/or flat fused rings found, for example, in steroid molecules. A steroid derivative, e.g. a smaller than fill steroid molecule, two to three fused six member ring molecules can be cross linked via usual cross linkers to provide a size and an over all hydrophobicity comparable to the Fmoc and other hydrophobic groups described herein. Since safe metabolic pathways exist for larger molecule consisting of these smaller building blocks, the toxicity of such hybrid molecules is expected to be small. In a preferred embodiment, the hydrophobic molecules are in a size range of about 17 by 12 Angstroms. It will be appreciated that where the peptide is to be delivered in vivo fluorophores of reduced or no toxicity are preferred. Toxicities of numerous fluorophores are well known to those of skill in the art (see, e.g., Haugland, *Handbook of Fluorescent Probes and Research Chemicals, 6th Ed.*, Molecular Probes, Eugene, Oreg. (1996). In addition, toxicity (e.g., $LD_{50}$) can be readily determined according to standard methods well known to those of skill in the art. In a most preferred embodiment, the fused ring compound is a fused steroid such as structures XI and XII illustrated in Latt et al.(1965) *J. Am. Chem. Soc.*, 87: 995-1003, where —$OR_1$ and —$OR_2$ can serve as activated points of attachment for the ends of peptides, nucleic acids or other molecules it is desired to transport into the cell.

As indicated above, the cellular uptake of almost any molecule will be enhanced by the attachment of the hydrophobic group and fluorophore or steroid crosslinkers. Thus, suitable molecules include virtually any molecule it is desired to introduce into the cell. Particularly preferred molecules include, but are not limited to, polypeptides (e.g., the protease inhibitors of this invention) and nucleic acids (e.g. oligonucleotide HIV inhibitors (see, e.g., Jing (1997) *Biochem.*, 36: 12498-12505), ribozymes, peptide nucleic acids, and the like).

X. Activity Detection Kits

The present invention also provides for kits for the detection of protease or other activity in samples or for the identification of modulators of such activity. The kits comprise one or more containers containing the fluorogenic protease indicators of the present invention. The indicators may be provided in solution or bound to a solid support. Thus the kits may contain indicator solutions or indicator "dipsticks", blotters, culture media, and the like. The kits may also contain indicator cartridges (where the fluorogenic indicator is bound to the solid support by the "acceptor" fluorophore side) for use in automated protease activity detectors.

The kits additionally may include an instruction manual that teaches the method and describes use of the components of the kit. In addition, the kits may also include other reagents, buffers, various concentrations of protease inhibitors, stock proteases (for generation of standard curves, etc), culture media, disposable cuvettes and the like to aid the detection of protease activity utilizing the fluorogenic protease indicators of the present invention.

It will be appreciated that kits may additionally or alternatively comprise any of the other indicators described herein (e.g., nucleic acid based indicators, oligosaccharide indicators, lipid indicators, etc). In this instance the kit will facilitate detection of the particular activities/compounds/interactions for which the particular indicator backbone is a substrate or binding agent.

XI. Protease Inhibitors

It was also a discovery of this invention that the protease indicators can also act as protease inhibitors. Protease inhibitors and protease substrates share several basic properties such as ability to bind to protease's catalytic substrate binding site, and form a relatively stable complex with a protease. Hence, many normal substrates or their fragments exhibit competitive substrate inhibition at higher concentrations. The inhibition is competitive since the inhibitor binds to the same substrate binding site of the protease whereby it competes with the native substrate in binding to the protease's catalytic domain.

This invention provides three novel approaches for protease inhibitor design. In the first approach, a normal substrate is redesigned such that it binds to protease well, but has a reduced (slow or non-existent) hydrolysis rate. The slow hydrolysis rate is achieved by introducing an altered (different) conformation and/or conformational flexibility into the protease recognition domain. After the (e.g., native) substrate binds to the protease's substrate binding site, the conformation of the peptide bond between $P_1$ and $P_1'$ is distorted into a transition conformation of a given protease's peptide bond hydrolysis reaction. If this peptide bond as well as adjacent peptide bonds are altered such that they are not distortable then the hydrolysis rate will be reduced as compared to a substrate whose cleavage site peptide bond is easily distorted into the desired transition conformation.

In a second approach, the inhibitor is produced by replacing the critical $P_1$ or $P_1'$ residue which makes it difficult to distort the cleavage site peptide bond. Normally, the amino acid side chains of $P_1$ and $P_1'$ residues interact specifically with the side chains of the protease catalytic domain. These specific interactions facilitate coordination of the peptide bond distortion into a transition conformation of the hydrolysis reaction. Thus, for example, when the critical $P_1$ residue of aspartic acid residue in the CPP32 protease substrate is replaced with non-charged asparagine then normal interaction between the substrate and protease does not take place even though the modified substrate binds to the protease's substrate binding site. Again, this leads to a slower or zero hydrolysis rate. The example of this $P_1$ residue substitution effect in designing an inhibitor is illustrated by the properties of the DEVN peptide.

The $P_1'$ residue can be changed to introduce either charged amino acid side chains or a structurally rigid, e.g., proline, residue as illustrated in the Table 3, substrate sequences for Hepatitis C viral protease substrate NS3 NS5A/5B of DVVCCSMS (normal substrate, SEQ ID NO: 182) and DVVCCPdMS (inhibitor, SEQ ID NO: 183). The underlined residues are the $P_1$ residues.

In a third approach, the amide bond between $P_1$ and $P_1'$ residues of a substrate can be changed to a non-hydrolyzable chemical bond including, but not limited to an ether, thioether, methylene bond, or alkylene (C=C) or ether bond (C—O—C(=O)) keeping the same amino acid side chains for the $P_1$ and $P_1'$ residues. Also the amide bond can be substituted with a retroinverso bond or other pseudo amino acid bond such as $CH_2$—NH or C(=O)—S replacing the carbonyl group with a $CH_2$ group.

EXAMPLES

The invention is illustrated by the following examples. These examples are offered by way of illustration, not by way of limitation.

Example 1

Synthesis of Fluorogenic Molecule for Detecting Protease Activity

Peptide syntheses and derivitizations were performed as described in PCT publication PCT/US98/03000 (WO 98/37226) which is incorporated herein by reference.

Example 2

The Fluorogenic Protease Indicators Provide a Strong Signal When Digested

In order to demonstrate that the fluorogenic protease indicators of this invention are easily digested by a protease, the degree of cleavage was determined by assaying for the appearance of indicator cleavage products in the presence of a protease.

Approximately 1 microgram of protease indicator, having the formula $F^1$-Asp-Ala-Ile-Pro-Nle-Ser-Ile-Pro-Cys-$F^2$ (SEQ ID No: 184) where $F^1$ is a donor fluorophore (5'-carboxytetramethylrhodamine (5-TMR)) linked to aspartic acid via the alpha amino group and $F^2$ is an acceptor fluorophore (rhodamine X acetamide (R492)) linked via the sulfhydryl group of the cysteine was dissolved in a buffer consisting of 50 mM sodium phosphate, 1 mM EDTA at pH 8.9. To this solution was added 1 unit of elastase. The solution was analyzed by HPLC before and about 30 minutes after the addition of elastase. The digestion was carried out at 37° C. The HPLC separated components were monitored at a wavelength of 550 nm which allowed detection of both the 5-TMR fluorophore the R492 fluorophore and at 580 nm which allowed detection of the R492 fluorophore.

Figure 1B:
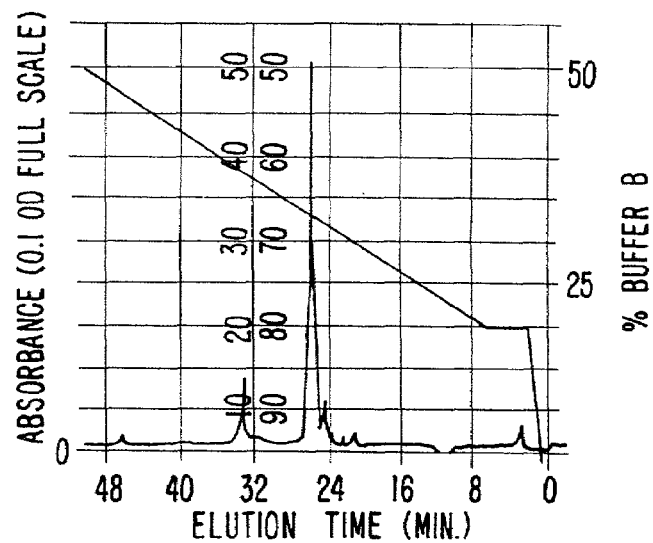
Figure 1C:
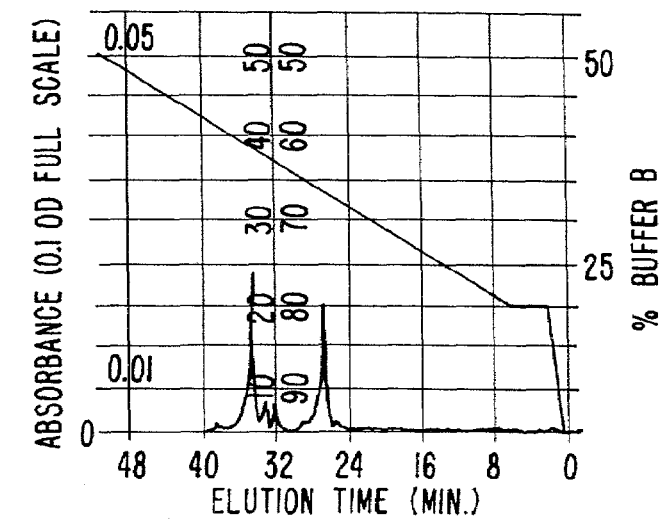

The results are indicated in FIG. 1 which shows the HPLC profiles of the fluorogenic protease indicator solution before and after addition of the protease elastase. FIG. 1(a) shows the HPLC before addition of the elastase showing a single peak representing the intact fluorogenic protease inhibitor. After addition of the elastase (FIGS. 1(b) and 1(c)) there was no trace of the late eluting single peak (FIG. 1(a)) indicating complete digestion of the fluorogenic protease indicator. In addition, the two predominant peaks in FIGS. 1(b) and 1(c) indicate that the digestion occurred primarily at a single site. There are a few smaller peaks indicating a low degree of digestion at other sites within the peptide sequence, however, the striking predominance of only two digestion peaks suggests that these secondary sites were not readily accessible to the elastase.

Changes in the emission spectrum of the fluorogenic protease indicator after the addition of an elastase protease was monitored using an SLM spectrofluorometer model 48000 with slit widths set at 4 nm on both the excitation and emission sides. All measurements were carried out at 37° C.

Figure 2A:
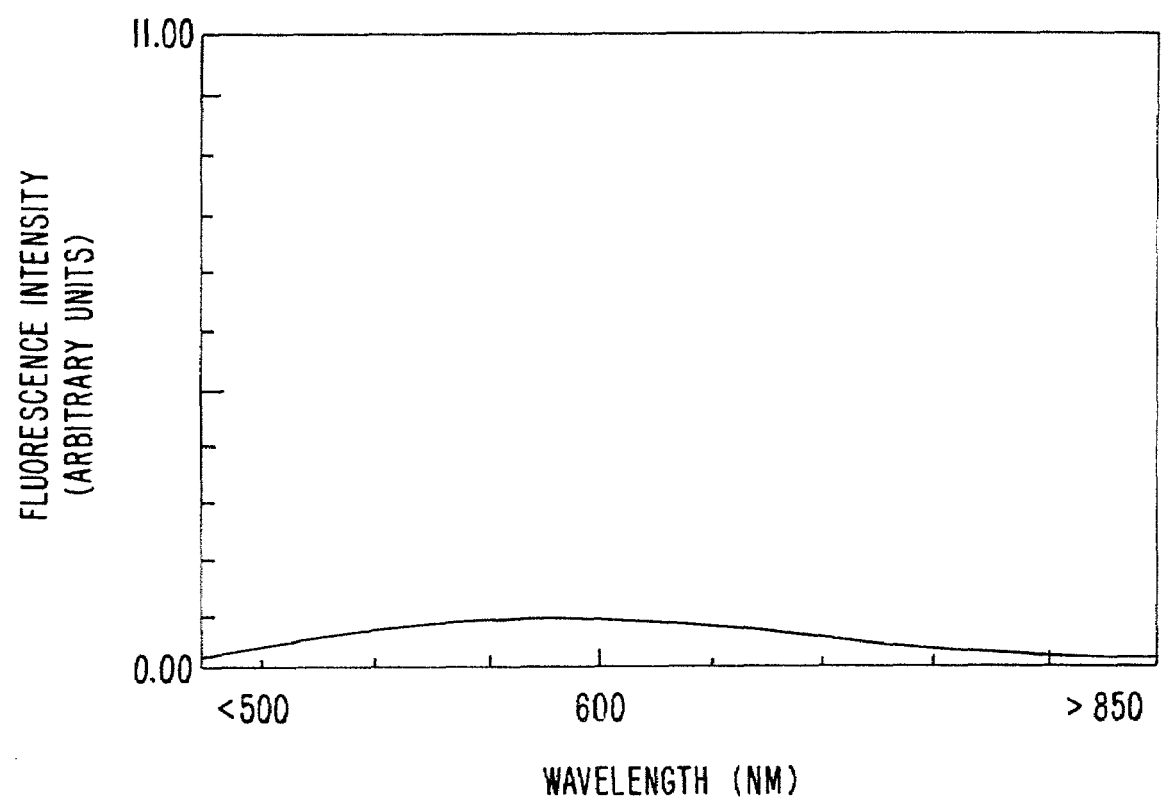
FIGS. 2A and 2B show the emission spectra of the D-NorFES-A fluorogenic protease indicator (FIG. 2A) before and (FIG. 2B) after the addition of elastase.
Figure 2B:
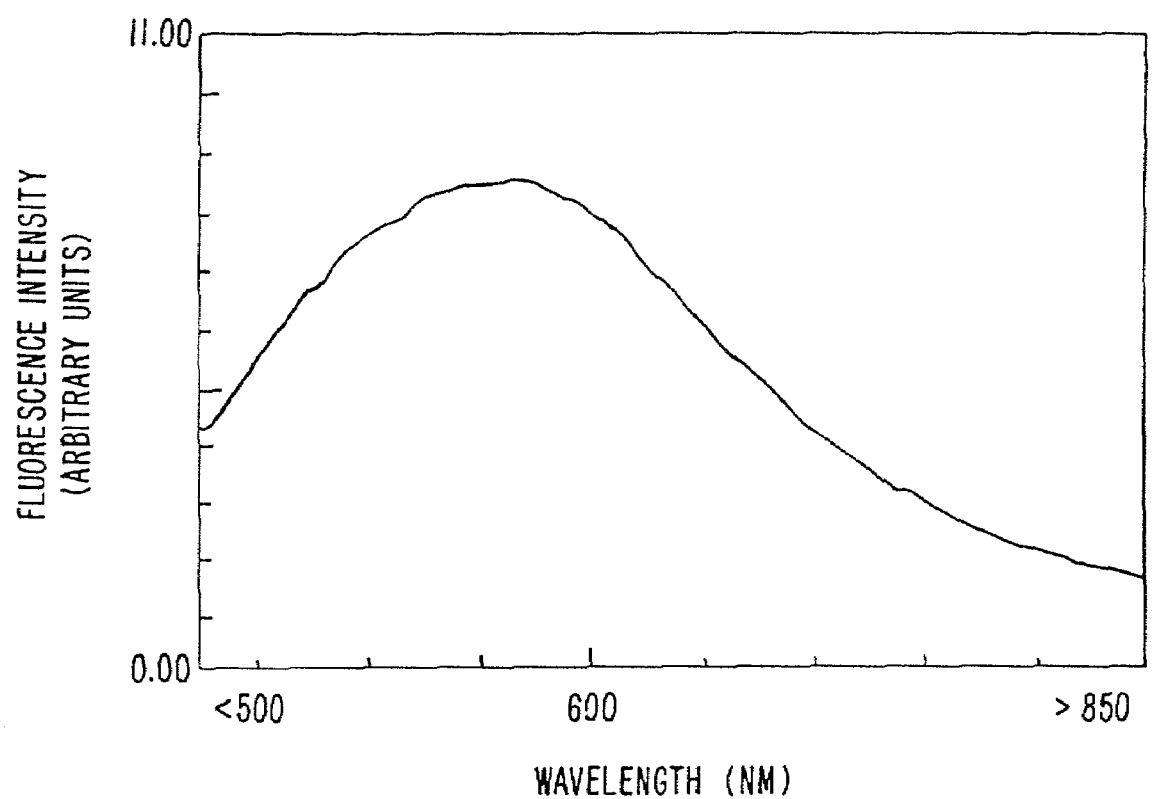
Figure 3:
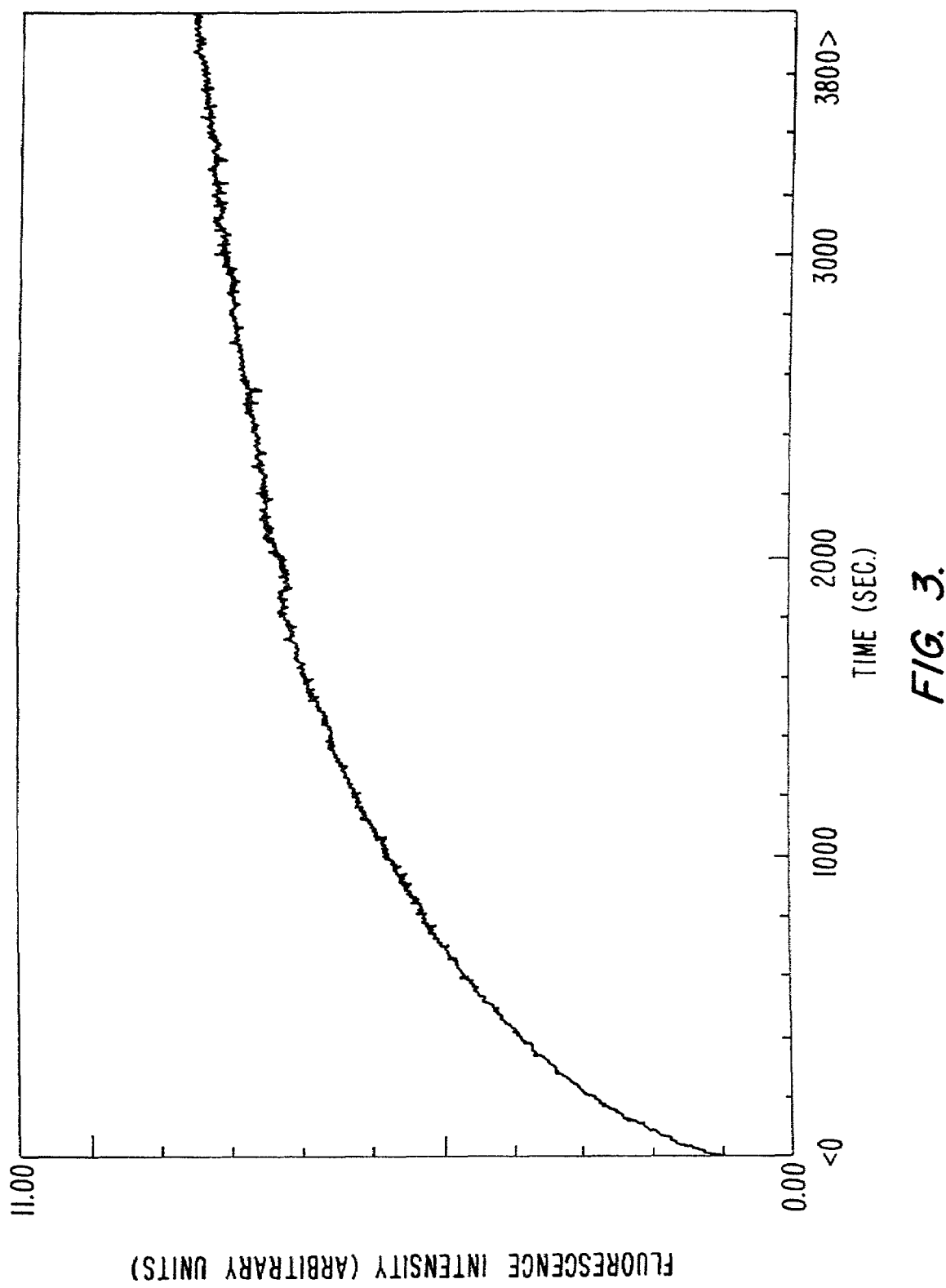
FIG. 3 shows the time-dependent increase of the fluorogenic protease indicator of FIG. 1, as a function of time after addition of 1 unit of elastase.

Spectra in FIG. 2 show emission of the fluorogenic protease indicator (a) before and (b) after addition of elastase, while the time dependent increase of the indicator's donor fluorophore emission intensity, after addition of elastase, is plotted in FIG. 3. The fluorogenic protease inhibitor showed more than a 10 fold increase in fluorescence at 589 nm after treatment with the elastase protease (FIG. 2(a) compared to FIG. 2(b)) with over a 5 fold increase in fluorescence occurring within the first 1000 seconds of exposure to the protease. The changes in intensity between treated and untreated indicators are, to some degree, a function of slit widths used, since they represent the signal integrated across the particular slit width. Thus, if wider slit widths were used (e.g. 8 or 16 nm slits) an even greater signal would be provided in response to digestion.

Example 3

Quenching and Release of a Peptide Doubly-Labeled with One Fluorophore

It was a surprising discovery of this invention that the peptide backbones of this invention doubly labeled with one fluorophore still achieve fluorescence quenching thus suggesting quenching through another mechanism besides resonance energy transfer.

In order to assess the extent ground-state dimerization and collisional quenching contribute to the total observed quenching, the series of doubly-labeled peptides listed in Table 5 was synthesized.

In addition to comparing absorption spectra of the dyes alone with the NorFes peptides singly labeled with each dye, emission spectra taken before and after cleavage were compared to determine the percent of quenching and the existence of fluorescent signal quenching by means other than resonance energy transfer (RET).

Fluorophores were linked to the amino terminus via the α-amino group of Aspartic acid residue (D) and to the ε-amino group of lysine (K). Labeling was accomplished by the displacement of a succinimidyl group linked to 6-TMR or DER. The structure of the peptide, called NorFES-KGY (SEQ ID NO: 185):

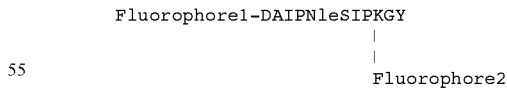

As determined from absorption spectroscopy, all doubly-labeled peptides, except fluorescein-NorFES-fluorescein, showed the existence of so called ground-state dimers. This was indicated by shift of absorption maxima to shorter wavelengths as well as a shape change of the absorption spectra as compared with the spectra for the enzyme digested doubly-labeled samples. Upon cleavage with elastase, the ground-state dimers were destroyed and the resulting spectra were the same as a solution containing equal concentrations of the respective singly labeled peptides.

Without being bound to a particular theory, it is believed that the ground-state dimer formation observed in the compounds designed and synthesized according to the present invention indicates that the U-shaped conformation of the peptide backbone brings the fluorophores into close spatial proximity thus allowing quenching through ground-state dimerization. It was a surprising discovery that the polypeptides of this invention allowed the formation of ground-state dimers at a significantly lower dye concentration than previously observed. For example, ground-state dimerization of free fluorescein dye in solution was only observed at concentrations higher than 0.74 M, ground-state dimerization of free Eosin dye in solution was only observed at concentrations higher than $2.8 \times 10^{-2}$ M (see, Forster and Konig (1957) *Zeitschrift fur Electrochemie*, 61: 344), and ground-state dimerization of Rhodamine B dye in solution was only observed at concentrations higher than $6 \times 10^{-4}$ M (see Arbeloa and Ojeda (1982) *Chemical Physics Letters*, 87: 556). In contrast, in the present invention, the effects are observed at $4.0 \times 10^{-7}$ M or about a 1000 fold lower concentration than the reported values.

The observation of the ground-state dimer for the compounds synthesized according to the present invention predicted a significant level of fluorescent quenching for doubly-labeled peptide with the same fluorophore as those compounds listed in Table 5. In fact this prediction was confirmed; a comparison of 6-TMR-NorFES-KGY-DER with 6-TMR-NorFES-KGY-6-TMR, i.e., the hetero doubly-labeled with the homo doubly-labeled peptides, indicates the degree of quenching is slightly higher in the hetero-vs. the homo-(94 vs. 90%). The fluorescein derivative, however, exhibited only 55% quenching. The symbols $I_0$ and $I_c$ for the percent fluorescent quenching (% Q) refer to the fluorescence intensity for the intact labeled peptide and the enzyme digested labeled peptide solution respectively.

TABLE 5

Cleavage rate ($T_{1/2}$) and percentage of quenching (% Q) of hetero- and homo-labeled peptides. $T_{1/2}$ is the time in seconds after addition of a protease (e.g. elastase) at which the fluorescence signal is 1/2 maximum. The symbols $I_0$ and $I_c$ refer to the fluorescence intensity (I) for the intact labeled peptide and the enzyme digested labeled peptide solution respectively.

| Compound | $T_{1/2}$ | % Q – (1 – ($I_0/I_c$)) × 100 |
|---|---|---|
| 6-TMR-NorFes-DER | 80 | 94 |
| 6-TMR-NorFes-6-TMR | 44 | 90 |
| 6-TMR-NorFes-6-TMR | 44 | 90 |
| DER-NorFes-DER | 152 | 90 |
| Fl-NorFes-Fl | 18 | 55 |
| 6-TMR-NorFes-DER | 80 | 94 |
| 6-TMR-K-NorFes-DER | 125 | 97 |
| 6-TMR-NorFes-6-TMR | 44 | 90 |
| 6-TMR-K-NorFes-6-TMR | 84 | 92 |

The substrate sequence could be extended by one amino acid residue and the fluorophore could be attached through the epsilon amino group on the lysine residue's side chain without major perturbation to the amount of observed quenching. Specifically, this addition (peptides designated K-NorFES-KGY) resulted in a slight decrease in cleavability rate and a very slight increase in the percent quenching for both the hetero- and homo-doubly-labeled peptide (in the K-NorFES-KGY peptides, N-terminal labeling was via the epsilon-amino group of lysine rather than the α-amino terminus).

Rates of cleavage ($T_{1/2}$) of these substrates by elastase were also measured by recording the time after addition of the protease at which the signal was one-half maximum (see, Table 5). A comparison of three homo-doubly-labeled peptides, i.e., NorFES-KGY labeled with two molecules of 6-TMR, DER, and fluorescein (Fl), shows the order of cleavability to be: Fl-NorFES-KGY-Fl>6-TMR-NorFES-KGY-6-TMR>DER-NorFES-KGY-DER.

Example 4

Dye-dye Dimers are Formed in Long Peptides

In addition, (homodoubly-labeled) PAI-2, CS-1 (a 31 residue long peptide) and two DEVD-like peptides were synthesized and derivatized. PAI-2 and CS-1 allowed the dye-dye dimer formation. The CS-1 peptide showed that in a significantly longer peptide the dye-dye dimer structure can be formed. Note this peptide contained four proline residues in the amino terminal side of the putative cleavage site Ile-Leu bond. There was one proline in the carboxyl domain as well. The results from the CS-1 peptide support a potentially larger sequence between the two dyes (fluorophores). Two DEVD-like peptide's amino acid sequences that did not allow the formation of productive H-type dimers are $F_1$-DEVDGIDPK[$F_1$]GY (SEQ ID NO: 186) and $F_1$-PDEVDGIDPK[$F_1$]GY (SEQ ID NO: 187).

Example 5

Cellular Uptake of Substrates Examined by Flow Cytometric and Fluorescence Microscopic Analysis The compounds listed in Table 6 were synthesized and assayed for cellular uptake. Cellular internalization of the substrates was tested using Jurkat cells (a human acute T cell leukemic line), HL-60 cells (a human promyelocytic leukemic line), human lymphocyte lines, A1.1 cells (a murine T-cell line), and murine primary thymocytes. Procedures used in determining substrate uptake by viable cells are provided in Example 6 (for the HPLC procedures), in Example 2 (for the fluorescence microscopic analysis), and in Example 3 (for the flow cytometric analysis) a summary of these analyses with respect to cellular uptake of substrates is presented in this example.

TABLE 6

Compounds assayed for cellular uptake. Abbreviations used in the following table are: $F^1$: carboxytetramethylrhodamine; Z: benzyloxycarbonyl group; Fm: Fmoc group; K[F1]: $F^1$ is covalently attached though the epsilon amino group of lysine (K). Single letter amino acid residues are used in the sequences except for Nlu for norleucine, B for aminoisobutyric acid and J for epsilon amino caproic acid residue. H: HPLC, FM: Fluorescence microscopy, FC: flow cytometry.

| | Structure | Cellular uptake/ magnitude | Uptake checked by | |
|---|---|---|---|---|
| 1 | Fm-K[F1]DAIPNluSIPK[F1]GY | Yes/ high | FM | 188 |
| 2 | K[F1]DAIPNluSIPK[F1]GY | Yes/ weak | FM | 189 |
| 3 | Fm-DAIPNluSIPK[F1]GY | No/ | FM | 190 |
| 4 | Fm-K[F1]DBDEVDGIDPK[F1]GY | Yes/ high | FM & FC | 191 |
| 5 | K[F1]DBDEVDGIDPK[F1]GY | Yes/ weak | FM | 192 |

TABLE 6-continued

Compounds assayed for cellular uptake. Abbreviations used in the following table are: $F^1$: carboxytetramethylrhodamine; Z: benzyloxycarbonyl group; Fm: Fmoc group; K[F1]: $F^1$ is covalently attached though the epsilon amino group of lysine (K). Single letter amino acid residues are used in the sequences except for Nlu for norleucine, B for aminoisobutyric acid and J for epsilon amino caproic acid residue. H: HPLC, FM: Fluorescence microscopy, FC: flow cytometry.

| | Structure | Cellular uptake/ magnitude | Uptake checked by | |
|---|---|---|---|---|
| 6 | Fm-K[F1]DBDEVNGIDPK[F1]GY | Yes/high | FM | 193 |
| 7 | K[F1]DBDEVNGIDPK[F1]GY | Yes/weak | FM & H | 194 |
| 8 | Fm-K[F1]DBEVDGIDPK[F1]GY | Yes/high | FM & FC | 195 |
| 9 | K[F1]DYBADGIDPK[F1]GY | Yes/weak | FM | 196 |
| 10 | Fm-K[F1]DBGEVDGIDGPK[F1]GY | Yes/high | H & FC | 197 |
| 11 | Fm-K[F1]DBJGDEVDGIDGJPK[F1]GY | Yes/high | FC | 198 |
| 12 | Z-K[F1]DBJGDEVDGIDGJPK[F1]GY | Yes/weak | FM | 199 |
| 13 | Fm-K[F1]DYBADGIDPK[F1]GY | Yes/high | FM | 200 |
| 14 | K[F1]DBEVDGIDPK[F1]GY | Yes/weak | FM | 201 |

The data listed in Table 6 indicate that: (1) the presence of two fluorophores alone is not optimum for cellular uptake as illustrated by structures 2, 5, 7, and 9; (2) addition of a 9-fluorenylmethoxycarbonyl (Fmoc) group at the alpha amino group plus attachment of only one fluorophore, does not result in significant cellular uptake (e.g., compound 3); and (3) two fluorophores plus at least one Fmoc group allows efficient cellular uptake of the substrates (structures 1, 4, 6, 8, 10, 11, and 12).

Other experiments utilizing protease substrates of this invention labeled with two identical fluorophores and at least one additional hydrophobic group such as an Fmoc group fits this paradigm. Replacing this Fmoc group with the less hydrophobic and smaller benzyloxycarbonyl group resulted in lower levels of cellular uptake, but was significantly better than a compound without a hydrophobic group such as DEVD peptide compound structure 5.

These data indicate that Fmoc may be replaced with Benzyloxycarbonyl, Z, or other hydrophobic groups such as Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4'-dimethoxybenzhydryl (Mbh),Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), benzyloxymethyl (Bom), t-butoxycarbonyl (Boc), cyclohexyloxy (cHxO),t-butoxymethyl (Bum), t-butoxy (tBuO), t-Butyl (tBu), acetyl (Ac), and trifluoroacetyl (TFA).

When the acid groups on compound 5, DEVD peptide, were ethyl esterified, this modified peptide did not show any enhanced cellular uptake by viable cells. Hence the importance of the Fmoc group and the two fluorophores forming H-type dimers are illustrated by this negative example.

Example 6

Fluorescence Microscopic Analysis of Cells Incubated with Elastase or Apoptosis-Related Protease Substrates The elastase substrate, Fm—K[F1]DAIPNluSIPK[F1]GY (SEQ ID NO:185), (where F1 was carboxytetramethylrhodamine, Fm was Fmoc, K[F1] was F1 covalently attached through the epsilon amino group of lysine (K), and Fm—K is the Fmoc group covalently attached at the alpha amino group of the amino terminal lysine residue) was used with HL-60 cells. Cells were incubated with various concentrations of elastase substrate ranging from 10 nM to 10 µM for 5 minutes to 60 minutes. Then the cells were diluted 5-fold with RPMI 1640 medium containing 5% serum or with phosphate buffered saline. The samples were centrifuged and washed once more with 1 ml of washing solution. After centrifugation and removal of the washing solution, cell pellets were loosened with about 25 ul of medium and these cells were transferred to a glass capillary. Capillary tubes were then placed on a glass microscope slide and examined under a fluorescence microscope using standard rhodamine filters.

For apoptosis-related protease activity determination, 10 µM concentration of the compounds listed in Example 8 (compound structures 2 through 13) were incubated with cells for 30 min. to 3 hours. The cells were then washed similarly twice. Using glass capillary tubes, the washed cells were transferred and examined under a fluorescence microscope.

Example 7

Flow Cytometric Analysis of Cells Incubated with Apoptosis-Related Protease Substrates The concentration of substrates used in flow cytometric analysis was 10 M in RPMI1640 medium containing 4 to 10% fetal calf serum. Cell densities during incubation with the chosen substrates ranged from 50,000 cells per ml to 4,000,000 per ml. Incubation times were from 30 min. to 3 hours at 37° C. and incubation volumes were 50 µL to 2 ml. After incubation with substrate for 30 to 60 min. cell suspensions were diluted 10-fold with ice cold Hank's Buffered Saline Solution (HBSS). This filtered cell suspension was then subjected to flow cytometric analysis using a 488 nm excitation source. Becton Dickenson, Inc.'s flow cytometer, FacSort, was used in the flow cytometric analysis. Typically, 10,000 to 30,000 events per sample were collected.

Control cells without substrate incubation and the sample with the greatest expected fluorescence signals were used to set the instrument detector parameters. For example after 15 minutes incubation of Jurkat cells with substrate compound #11 Fm-CGD2D: Fm—K[F1]DBJGDEVDGIDGJPK[F1]GY (SEQ ID NO: 202, where F1 was carboxytetramethylrhodamine; Fm was Fmoc, K[F1] was F1 covalently attached through the epsilon amino group of lysine (K), Nlu was norleucine, B was aminoisobutyric acid, and J was epsilon-aminocaproic acid) an increase of about 10 channels indicating cellular uptake of the substrates was measured. Note substrate #11 was not completely quenched. Hence, a small amount of background fluorescence would be expected from the intact substrate. Signals from the cells that had been activated with 1 µg/ml of ant-Fas antibody, CH11 clone for 1 to 6 hours indicated an increase in peak channel number. As much as a ten-fold increase in fluorescence intensity was observed. When the cells were co-incubated with the CPP32 protease inhibitor ZVAD-fluoromethylketone at 50 μM along with an apoptosis inducing agent, e.g., anti-Fas antibody, this observed increase in fluorescence intensity was eliminated. This indicated that the signal from compound 11 was due to the CPP32 protease activity which was inhibitable by ZVAD-FMK. Hence, the observed fluorescence intensity in each cell as determined by flow cytometric analysis served as a direct measure of the intracellular CPP32 protease activity.

Example 8

Competitive Substrate Inhibitors Illustrated by Their Effects on Cell Lysate Hydrolysis of Apoptosis-related Protease Substrates The level of CPP32 protease activity in the 6 hr ant-Fas-stimulated Jurkat cell lysate was examined using the protease substrate, DEVD-AFC (where AFC is aminofluoromethyl coumarin) 50 μM substrate concentration at 37° C. The buffer used was 50 mM HEPES, pH7.5, 10% w/v sucrose, 0.1% w/v CHAPS.) Fluorescence intensity changes were monitored with an SLM 48000 spectrofluorometer. The hydrolysis rate of DEVD-AFC was found to depend upon the concentration of DEVD, DEVN, and ICE substrates (compounds 5, 7, and 9 in Table 6) present in the reaction mixtures. As the concentrations of DEVD, DEVN, and ICE were raised to 25 μM, the rate of DEVD-AFC hydrolysis was decreased. Hence, DEVD, DEVN and ICE substrates do bind to the substrate binding site of target proteases such as CPP32 and act as competitive inhibitors since their hydrolysis rates are slower than that of DEVD-AFC substrate. It was surprising to find that the substrate control peptide with its $P_1$ residue mutated with a conservative uncharged residue Asn still retained the ability to bind to the protease substrate binding site and exhibit enzyme inhibition.

Example 9

Structural Characteristics of Fluorophores Which Form Intramolecular H-type Dimers in a Protease Substrate The strongest correlations between H-dimer formation and structural elements of various potential fluorophores for use in the homo-doubly labeled fluorogenic compositions of this invention are in order: delocalized charge, symmetry, and transition dipole magnitude. Hydrophobicity was not observed to be a major determinant in this type of dimerization.

In the experiments described herein, a new class of profluorescent protease substrate was designed and synthesized. These new fluorogenic indicators have spectral properties that fit the exciton model; More specifically, spectra of these polypeptides which were doubly labeled with rhodamines showed a blue-shifted absorption peak and fluorescence quenching, both indicators of H-dimer formation.

For example, NorFes, an undecapeptide which is cleaved by the serine protease elastase, was homodoubly labeled on opposite sides of its cleavage site with six fluorophores in order to identify structural elements of dyes which influence intramolecular H-type dimer formation. Absorption and fluorescence spectra of these six substrate obtained before and after enzymatic cleavage suggest that the presence of a delocalized charge in the intramolecular dimer followed by symmetry and then magnitude of the transition dipole are important factors in dimer formation. Surprisingly, there was no evidence that hydrophobic interactions were important in the fluorophores used in this study.

The six fluorophores used in this study were rhodamine-X, tetramethylrhodamine, fluorescein, diethylaminocoumarin, hydroxycoumarin and pyrene.

While the xanthene components of these two rhodamines (rhodamine-X, tetramethylrhodamine) have the same charge and symmetric structure, the distinguishing characteristics between them are a higher transition dipole magnitude and lower hydrophobicity of the tetramethylrhodamine. One notes that the spectrum of the intact tetramethylrhodamine-derivatized substrate shows a more prominent change than that of rhodamine-X when comparing the absorption spectra of the two doubly-labeled intact peptides with those from the respective cleaved solution.

As noted above, in contrast to the two rhodamine derivatives where a charge of +1 is localized over each of the xanthene structure, the three conjugated ring component of the fluorescein was not positively charged at pH 9. The lack of any significant shape changes in the absorption spectra after separation of the dyes (fluorescein) by cleavage of the peptide suggests a role for positive charge in xanthene H-dimer formation. The less pronounced, but nevertheless finite quenching observed with this derivative points toward a diminished but finite degree of interaction between two fluoresceins compared with interactions between either of the two rhodamines is consistent with previous studies of xanthene in solution where the association constant for dimer formation for fluorescein is four order of magnitude lower than that for rhodamines.

The influence of dye symmetry was next examined using two coumarins, i.e. diethylaminocoumarin and hydroxycoumarin. This class of molecules contains no symmetrical elements. The diethylaminocoumarin bears a positive charge delocalized over its two conjugated rings, similar to the rhodamines and the hydroxycoumarin is neutral at pH 9, similar to fluorescein. The spectrum of diethylaminocoumarin-labeled NorFes exhibits a blue shift of 11 nm while that of hydroxycoumarin-labeled NorFes shows just a slight blue shoulder. The respective degree of quenching, 76% and 28% of the intact peptides relative to the cleaved solutions is consistent with the importance of delocalized charge. Comparing the less pronounced spectral changes of the diethylaminocoumarin-derivatized peptide with those of the xanthene gives support to the role of symmetry as an important element in H-dimer formation.

Finally, the role of hydrophobicity was studied using pyrene, a fluorophore with S2 symmetry containing only carbons and hydrogens. No spectral changes were observed in either the absorption or the fluorescence mode and the magnitude of the transition dipole is extremely small. These results provide evidence against a dominant role for hydrophobicity in H-dimer formation.

In summary, the strongest correlations between H-dimer formation and structural elements are in order: delocalized charge, symmetry, and transition dipole magnitude. Hydrophobicity was not observed to be a major determinant in this type of dimerization.

Example 10

High Throughput Screening

When the indicators of this invention utilize fluorescent molecules that emit at a wavelength ranging from about 650 nm to about 720 nm, they are well suited for use in a variety of instruments suitable for high-throughput screening. One such instrument is the Perkin Elmer Applied Biosystems FMAT™ System 8100 automated, macro-confocal high-throughput screening (HTS) system for fluorescent, homogeneous, multiplexed, live cell- and bead-based screening assays.

Cells were plated at a density of between 3 and 15×10$^3$ cells per well in a 96-well flat-bottomed plate. One population of cells was incubated with an apoptosis inducing agent, e.g., staurosporine at a concentration of ca. 1 µM for ca. 3-4 hours, and a second was treated with the vehicle, e.g., DMSO, for an equal time. Following the induction period, PhiPhiLux (OncoImmunin, Inc.) cell permeable fluorogenic substrate comprising two IC5 fluorophores, was added at a final concentration of ca. 2 µM. Incubation was carried out for 1 hour. The plate was placed in an FMAT™ 8100 instrument and the number of fluorescent cells in each well was counted.

In preferred embodiments, the system simply was used "as is" by turning down the gain on the photomultiplier tube (reducing detector sensitivity) until a desirable signal to background level was obtained.

Other modifications to the FMAT™ 8100 to enhance the utility of this instrument, particularly for detection of intracellular protease activity using the indicators of this invention can be made. In one modification, the machine is modified to permit the introduction of a neutral density filter at the emission side to reduce the total emission signal provided by the fluorescence indicator. This allows the detector to be run without a decrease in sensitivity. A continuously variable filter stepped filters (e.g. in a filter wheel) allow the appropriate degree of signal reduction to be selected.

A variable pin hole can be provided rather than the fixed pin hole in the FMAT™ to permit selection of optical section thickness. The current instrument utilizes a fixed 100 µm optical section. A preferred thickness range would be from 0.1 µM to 100 µm, and for use with the indicators of this invention, an optical section thickness of about 10 to 20 µm is most preferred.

The introduction of an option for bright field and/or phase contract image capture permits one to switch between imaging the protease indicator signal and the cell. This facilitates determination of the total cell number within the field.

Increasing the magnification settings on the FMAT allows one to capture subcelluar localized images rather than low resolution whole cell images. This facilitates localization of protease activities to particular subcellular organelles or domains.

Introduction of UV laser excitation option along with the existing helium-neon laser permits the use of existing nuclear stains such as Hoechst dye to count the nucleus and thereby facilitate cell counting.

Modifications to the image analysis software accompanying the FMAT™ 8100 can also be made. For example, the software can be modified to permit grouping one or more subpopulation groups by applying various measured parameters such as particular feature shape, brightness, size, the existence of particular labels, and the like. This allows, for example, correlation of the enzyme activity with one or more physiological parameters or markers.

Modification of the software for real-time captured image analysis allows counting of cell number or number of subcellular features thereby permitting the device to normal its data acquisition protocols.

Example 11

Assessment of Caspase Activities in Intact Apoptotic Thymocytes Using Cell-permeable Fluorogenic Caspase Substrates To detect caspase activities in intact apoptotic cells at the single cell level, cellpermeable fluorogenic caspase substrates were synthesized incorporating the optimal peptide recognition motifs for caspases 1, 3/7, 6, 8, and 9. Caspase activities were then assessed at various times after in vitro treatment of mouse thymocytes with dexamethasone or antiFas antibody. Dexamethasone induced the following order of appearance of caspase activities as judged by flow cytometry: LEHDase, WEHDase, VEIDase, IETDase, and DEVDase. Since the relative order of caspases 3 (DEVDase) and 6 (VEIDase) in the cascade has been controversial, this caspase activation order was reexamined using confocal microscopy. The VEIDase activity appeared before DEVDase in every apoptotic cell treated with dexamethasone. In contrast, antiFas stimulation altered this sequence: IETDase was the first measurable caspase activity and DEVDase preceded VEIDase. In an attempt to determine the intracellular target of the potent antiapoptotic agent carbobenzoxy-valylalanylaspartyl(bmethyl ester)fluoromethyl ketone (ZVAD[OMe]FMK), we examined its ability to inhibit previously activated intracellular caspases. However, no significant reductions of these activities were observed. These fluorogenic caspase substrates allow direct observation of the caspase cascade in intact apoptotic cells, showing that the order of downstream caspase activation is dependent on the apoptotic stimulus.

Introduction.

Since the seminal finding that the *Caenorhabditis elegans* death gene ced-3 encodes a protein homologous to the mammalian protease IL-1b-converting enzyme (ICE)1 (1), a family of related proteases has been described. Termed caspases, this family is characterized by both a catalytic cysteinyl residue and a strong preference for an aspartyl residue in the P1 position of their substrate recognition sequence. Both structural and functional studies have shown that caspases also recognize the P4 amino acid, and recent studies using combinatorial chemistry have suggested a division of the caspase family into three subfamilies based on pep-tide substrate recognition (2). The ICE subfamily (caspases 1, 4, and 5) prefers a bulky hydrophobic amino acid such as tyrosine or tryptophan at P4, the caspase 3 subfamily (caspases 2, 3, and 7) prefers a second aspartic acid residue at this site, and the caspase 6 subfamily (caspases 6, 8, and 9) prefers a branched hydrophobic side chain such as valine.

Caspases are expressed in cells as inactive proenzymes, which must be proteolytically processed in order to acquire activity. Consistent with the finding that the prototypic cleavage sites for such processing have the distinctive aspar-tic acid at P1, various caspases have been found to activate other procaspases, and a cascade of activating caspases has been described in cells undergoing apoptosis. Evidence has accumulated that the caspase cascade is normally initiated by oligomerization of either procaspase 8 or procaspase 9 via Fas-associated death domain protein (FADD) or apop-totic protein activating factor 1 (apaf-1), respectively. The subsequent order of the caspase activation cascade has been analyzed by ordering caspase processing events in cytoplasmic extracts of apoptotic cells, in conjunction with specific inhibitors. However, recent studies of caspase 9 indicate that procaspase processing is necessary but not sufficient for enzymatic activity (3), and other studies attempting to order the caspase cascade have resulted in conflicting proposals regarding the relative sequence of activation of caspases 3 and 6. Two studies have suggested that caspase 6 activates procaspase 3 (4, 5), while two studies have suggested the reverse order (6, 7). One major problem with analyzing the caspase cascade in extracts is that events controlled by the subcellular localization of regulatory components may not be accurately reproduced. The autoactivation of long prodomain caspases occurs in large complexes that are still not well understood; critical components such as cytochrome c, apoptosis inducing factor (AIF), and procaspases 2, 3, and 9 are found in the mitochondrial intramembrane space (8-11); transcriptional events clearly lie upstream of caspase activation in many examples of apoptosis; and Bcl2 family members move from a cytosolic to membrane localization during apoptosis (12).

The above complexities point out the need for a means to monitor caspase activation in intact apoptotic cells, so that the concepts derived from study of recombinant components and extracts of apoptotic cells can be tested in a physiological setting. To this end, we have designed and synthesized cellpermeable fluorogenic caspase substrates with specificity for caspases 1, 3/7, 6, 8, and 9 (13). These substrates are peptides of 18 amino acids, with caspase recognition motifs in the center, and rhodamine derivatives covalently attached near their termini. As previously shown noncovalent cyclization can occur in such modified peptides via intramolecular complexation of rhodamines with consequent quenching of the rhodamine fluorescence until proteolysis breaks the peptide linkage (13, 14). The two associated rhodamine dye molecules of the intact substrate appear to form a hydrophobic surface mediating the membrane permeability of these substrates (14-16). We have used these intracellular caspase substrates in conjunction with flow cytometry and confocal microscopy to examine caspase activities in the classic apoptotic system of thymocytes treated with corticosteroid or antiFas antibody in vitro. In the former case, the caspase cascade is triggered by apaf1-mediated aggregation of procaspase 9 (17, 18) while in the latter case it is via FADDmediated procaspase 8 aggregation, largely independent of procaspase 9 and the Bid amplification loop (19, 20).

We have also addressed the question of the pharmacological target of the widely used potent apoptosis blocker carbobenzoxyvalylalanylaspartyl(bmethyl ester)fluoromethyl ketone (ZVAD[OMe]FMK). This compound has been found to block a wide variety of apoptosis systems in vitro and has also been reported to protect mice from the lethal effects of intravenously injected antiFas, as well as ischemi-areperfusion in a stroke model (21, 22). Since ZVAD(OMe)FMK is widely regarded as a nonselective inhibitor of caspases, we expected that it would inhibit the intracellular caspase activities detected by our substrates. However, we found that although ZVAD(OMe)FMK blocks intracellular caspase activation in thymocytes when added before or at the same time as dexamethasone, it does not significantly inhibit any detectable intracellular caspase activities after they have already become activated.

Materials and Methods

Materials.

Thymocytes were prepared from 4-6wkold C57BL/6 mice obtained from Frederick Cancer Center. RPMI 1640 and FCS were from HyClone. Dexamethasone, DMSO, Hepes, CHAPS, Triton X100, leupeptin, E64, and iodoacetamide were from SigmaAldrich, and dithiothreitol (DTT) was from Pierce Chemical Co. Hamster anti-murine Fas antibody (Jo2) was obtained from BD PharMingen, and PElabeled goat F(ab9)2 anti-hamster IgG was from Caltag. The apoptosis inhibitor ZVAD(OMe)FMK was purchased from Alexis Biochemicals (some confusion exists about this compound, as not all suppliers make it clear that the normal commercial product is a methyl ester). PhiPhiLux™ and CaspaLux™ cellpermeable fluorogenic substrates were from OncoImmunin, Inc. Recombinant caspases 3, 6, 7, and 8 were obtained from BD PharMingen and Medical Biological Laboratories (Nagoya, Japan). Solvents such as HPLC grade dichloromethane, methanol, and acetonitrile were from Fisher Scientific. Propidium iodide (PI) and the fluorophores 59,69carboxytetramethylrhodamine succinimidyl ester and 59,69rhodamine green carboxylic acid succinimidyl ester were from Molecular Probes. Reverse phase HPLC equipment and columns were from Waters Corp. and SynChrom, Inc.

Caspase Substrates.

The reagents and methods used for peptide synthesis and derivatization have been described in detail previously (14). In brief, peptides were synthesized using both an automated peptide synthesizer and by manual solid phase methodology, and subsequently purified by reverse phase HPLC. Peptides were subjected to mass spectrometric analysis (PeptidoGenic Research) to determine the molecular mass and confirm peptide structure and composition. Each purified peptide was derivatized with the appropriate fluorophore as described previously (14). Substrates were purified into single components of homo-doubly derivatized peptides by reverse phase HPLC and further characterized by absorption and fluorescence spectroscopy.

Caspase Activity Measurements in Extracts and Intact Thymocytes.

Single cell suspensions of thymocytes were cultured in RPMI 1640 with 10% FCS at a concentration of 10 6 cells/ml. Dexamethasone (final concentration, 0.1 mM) and ZVAD (OMe)FMK (final concentration, 50 mM) were added at the indicated times from stock solutions in DMSO (100 mM for dexamethasone and 200 mM for ZVAD[OMe]FMK). For antiFas stimulation, wells in a 24 well plate were coated with antiFas antibody (20 mg/ml; 250 ml per well) overnight at 378 C. After twice washing the wells with medium containing 10% FCS, 4 3 10 6 thymocytes were added per well. After culture at 378 C in a 5% CO2 atmosphere for the indicated times, cells were centrifuged and resuspended in 75 ml of each substrate (10 mM) in 1.5 ml Eppendorf tubes. The open tubes were placed in the CO2 incubator for an additional 60 min. After washing in saline, cells were analyzed by flow cytometry. Caspase activity measurements in extracts with several known inhibitors and noninhibitors were carried out using fluorometers from Photon Technology International and SLMAMINCO. Cell lysates were prepared using a cell lysate buffer consisting of 50 mM Hepes, pH 7.5, 10% (wt/vol) sucrose, 0.1% (wt/vol) CHAPS, 0.5% (wt/vol) Triton X100, and 10 mM DTT. The substrate (10 mM) was prepared in 50 mM Hepes, pH 7.5, with 10 mM DTT. All measurements were made at 378 C using a thermostated cell holder in a 150 ml quartz cuvette (3 3 3. 45 mm; Starna Cells, Inc.). The temperature of the substrate solution was preequilibrated for 20 min, ensuring temperature equilibration by having a flat base line before cell lysate addition. A 10 ml aliquot from an apoptotic thymocyte lysate was added to 110 ml of substrate solution. The fluorescence intensity was then monitored for 30-60 min. The initial velocity was calculated from the linear portion of the fluorescence increase. Various amounts of inhibitors were added to the cell lysate for 20 min before addition of the cell lysate mixture to the substrate solution.

Flow Cytometry.

Instruments from both Becton Dickinson (FACSort™ and FACScan™) and Beckman Coulter (EPICS XL) were used in this study. 10 5 PInegative cellular events were analyzed for each file using FL1 versus FL3 dot plots to establish a PInegative gate using a polygon region. Throughout the entire time course of experiments, the determined PI-positive population of any sample was never. 20%. The EPICS XL was used for the forward scatter histograms and PI-gated fluorescence histograms shown in FIG. 6. In experiments with time course activation with antiFas antibody and with those of dexamethasone and carbobenzoxyvalylalanylaspartylfluoromethyl ketone (ZVADFMK), the caspase activity of the cell population and the order of caspase activation were determined by obtaining the mean fluorescence channel of all PInegative cells using CELLQuest™ (Becton Dickinson) or EXPO™ (Beckman Coulter) software.

Confocal Microscopy.

Cells were incubated with various substrates at 10 mM while suspended in RPMI 1640 plus 10% FCS, 10 mM Hepes, and 0.1 mM dexamethasone. Cell suspensions were transferred to a thermostated chamber with a no. 1 coverslip bottom, allowed to settle, and viewed on a ZEISS LSM410 laser scanning confocal microscope system using a 633, 1. 4 NA objective. Substrates were present at 10 mM throughout the course of the induction and imaging. Samples were excited using a 488/518 nM krypton/argon laser, and fluorescent and Nomarski images were acquired every 5 min. Fluorescent images were acquired as single optical sections 2-3 mm in thickness, and brightness/contrast settings were adjusted so that the fluorescent signal of cells without fluorescent substrate was near background. As the substrates are cleaved in apoptotic cells, cellular fluorescence shifts from below to above the fluorescence of the bulk solution in the same plane. Changes in cell size and fluorescence were analyzed using ImagePro® Plus (Media Cybernetics). The outlines of individual cells were manually traced from digitized RGB images, and cell area and integrated fluorescence intensities were calculated.

Results

Peptide Substrate Cleavage by Apoptotic Thymocyte Extracts.

Figure 5:
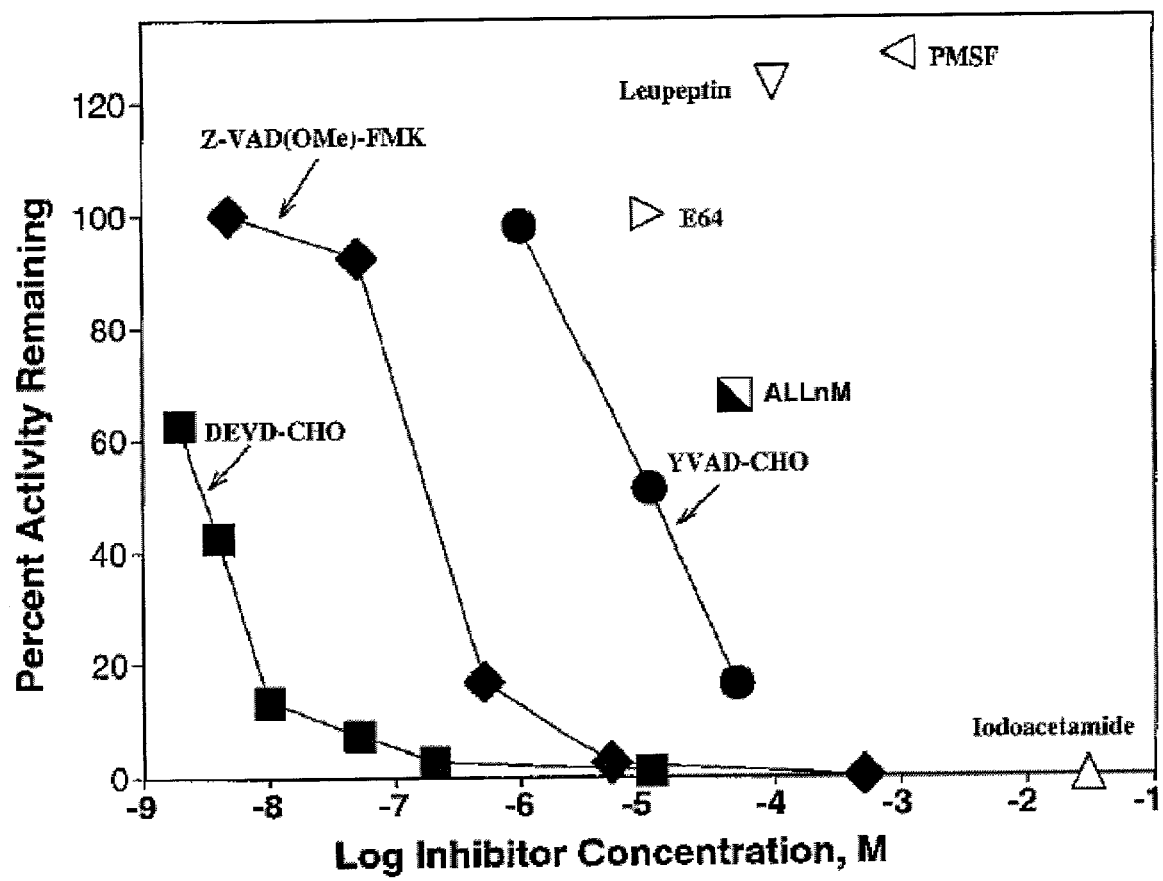
FIG. 5 illustrates the inhibition of DEVDase activity in apoptotic thymocyte extract using PhiPhiLux™ substrate. An extract of mouse thymocytes exposed to 0.1 mM dexamethasone for 6 h was incubated in fluorometer cuvettes at 37° C. with 10 mM PhiPhiLux™ substrate with or without the indicated protease inhibitors. Enzymatic activity was calculated from the rate of increase of fluorescence.

The caspase substrates used in these studies were based on optimal peptide recognition motifs for various caspases as reported by peptide library studies (2) and are described in Table I. To assess whether cleavage of these substrates in apoptotic thymocytes was due to caspases, we examined extracts from untreated fresh thymocytes, or from thymocytes treated with dexamethasone. We found that the DEVD substrate was cleaved 25fold faster by apoptotic thymocyte extracts than by fresh thymocyte extracts (on a cell basis), as expected from studies with other DEVD substrates (23). FIG. 5 shows the effect of various protease inhibitors on the apoptotic DEVDase activity, giving an inhibition profile expected for a caspase. Thus DEVDCHO is a potent blocker, followed by ZVADFMK, which together with the inhibition by iodoacetamide implicates a cysteine protease. The complete inhibition by DEVDCHO is consistent with the absence of proteases other than caspase 3 or a very closely related protease in the apoptotic thymocyte cell lysate that might cleave the DEVDase substrate and generate fluorescence increases. Additionally, the lack of inhibition by E64 or leupeptin is not compatible with this activity being due to lysosomal cathepsins or calpain, leaving caspases as the remaining candidate intracellular enzyme class responsible for the activity in extracts (24).

To confirm further that these substrates are cleaved by a caspase when loaded into apoptotic cells, we have carried out an HPLC analysis of the recovered intact substrate and the cleaved substrate fragments from the apoptotic thymocytes that have been incubated with these substrates for 15-30 min. When the fluorescent products in extracts of such apoptotic thymocytes were examined, the initial cleavage products detected were derived from a cleavage at the intended P1 aspartic acid in both cases, with subsequent secondary breakdown products formed (data not shown).

TABLE 7

Amino acid sequence of cell-permeable fluorogenic caspase substrates used in this example.

| Substrate | Target Caspase | Activity | Sequence | SEQ ID NO: |
|---|---|---|---|---|
| PhiPhiLux | Caspase 3/7 | DEVDase | KDPC5GDEVDG-IDGC5PKGY | 203 |
| CaspaLux-3PE | Procaspase 3 processing | IETDase | KDPC5GIETDSG-VGC5PKGY | 204 |
| CaspaLux-6 | Caspase 6 | VEIDase | KDPC5GLVEIDN-GGC5PKGY | 205 |
| CaspaLux-9 | Caspase 9 | LEHDase | KDPC5GLEHDG-INGC5PKGY | 206 |
| CaspaLux-1 | Caspase 1 | WEHDase | KDPC5GWEHDG-INGC5PKGY | 207 |

Intracellular Caspase Activities in Dexamethasonetreated Thymocytes

Quantitation of intracellular caspase activities in apoptotic thymocytes treated with dexamethasone in vitro is shown in FIG. 6. For these experiments, the apoptotic cells were sampled after various times of incubation as indicated, the five rhodamine green-based caspase substrates were loaded into aliquots of the cell suspension, and flow cytometry was subsequently carried out. By this approach, the period of substrate exposure was equivalent for all cells analyzed, allowing a comparison between different stages in the caspase cascade.

Figure 6A:
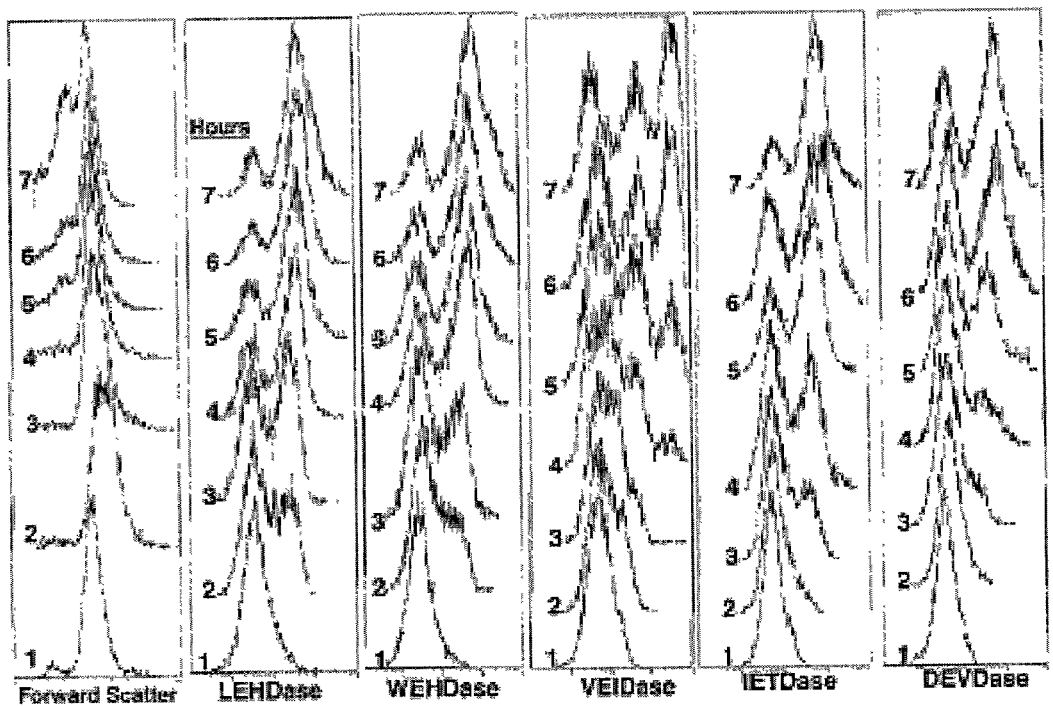
FIGS. 6A and 6B illustrate the analysis of caspase activation by flow cytometry.

In all cases, the 1 h time point shown in FIG. 6A gave identical profiles to fresh thymocytes, and this single peak was assumed to represent unhydrolyzed substrate taken up uniformly by the cells. Fresh thymocytes run without exposure to substrate had a single peak with ~10-fold less fluorescence (data not shown). Examination of all apoptotic profiles from all caspase substrates shows that a second discrete peak with an intensity z10fold higher than the initial fluorescence is formed with further incubation time, and this peak increasingly dominates the profile. The VEIDase activity profiles were unique in exhibiting two discrete peaks of increased fluorescence intensity, and at 6-7 h the population was divided roughly equally among three fluorescence levels.

The sequence of caspase activation can be best seen by examination of the profiles at the 2 h time point, which shows highest activity for the LEHD substrate, followed by WEHDase (or ICElike activity), VEIDase, and finally IETDase and DEVDase. Although about half the cells had increased their fluorescence by z10fold with the LEHD substrate at 2 h after addition of dexamethasone, a comparable increase in DEVDase activity was not observed until 5 h. As expected, the onset of the IETDase activity (caspase 3 processing enzyme) preceded the appearance of the DEVDase activity. Since all five substrates showed unique patterns of increased fluorescence with time, it appears that distinct enzymes with different kinetics of activation are responsible for the proteolytic activities of these substrates in thymocytes.

Intracellular Caspase Activities in AntiFas-Treated Thymocytes.

Figure 6B:
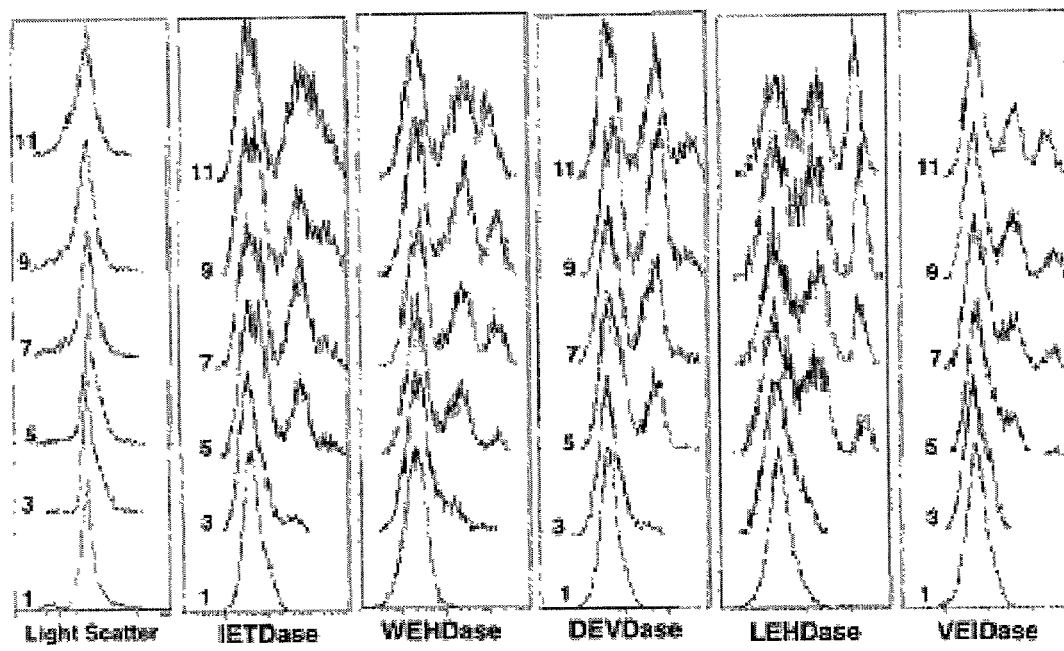

To compare the intracellular caspase activities in thymocytes with a distinctly different upstream activation pathway, we have carried out experiments parallel to the above with antiFas antibody (FIG. 6B). Compared with dexamethasone, caspase activation by saturating amounts of antiFas antibody was slow, and there was more heterogeneity of caspase activity in the apoptotic cells. The order of activation of caspases was determined by plotting the mean fluorescence of the PInegative cells between 1 and 3 h for each of the five substrates (data not shown), which increased in the order: IETDase, WEHDase, DEVDase, LEHDase, and VEIDase. Since the IETD substrate was optimal for caspase 8, this result is consistent with expectations that it initiates this cascade. Although the progression of caspase activation was less distinct for antiFas triggering than dexamethasone triggering, it is very clear that for the antiFas case DEVDase activity precedes VEIDase, in contrast to dexamethasone treatment of these cells.

Other differences between induction by the two stimuli were the distribution profiles and extent of induction. Thus, although stimulation by dexamethasone resulted in a bimodal pattern for all substrates except VEIDase (which became trimodal at later times), thymocytes stimulated with antiFas developed trimodal patterns with all substrates. To ascertain if antiFas-mediated IETDase activation of a subpopulation of thymocytes was due to differential cell surface expression of Fas, flow cytometry using the triggering antiFas antibody was used to compare Fas surface expression on IETDase high and IETDase low subpopulations. These showed identical histograms, indicating that differences in surface Fas expression did not account for the subpopulation differences in caspase activation among thymocytes (data not shown).

Ordering of VEIDase versus DEVDase by Confocal Microscopy.

Figure 7A:
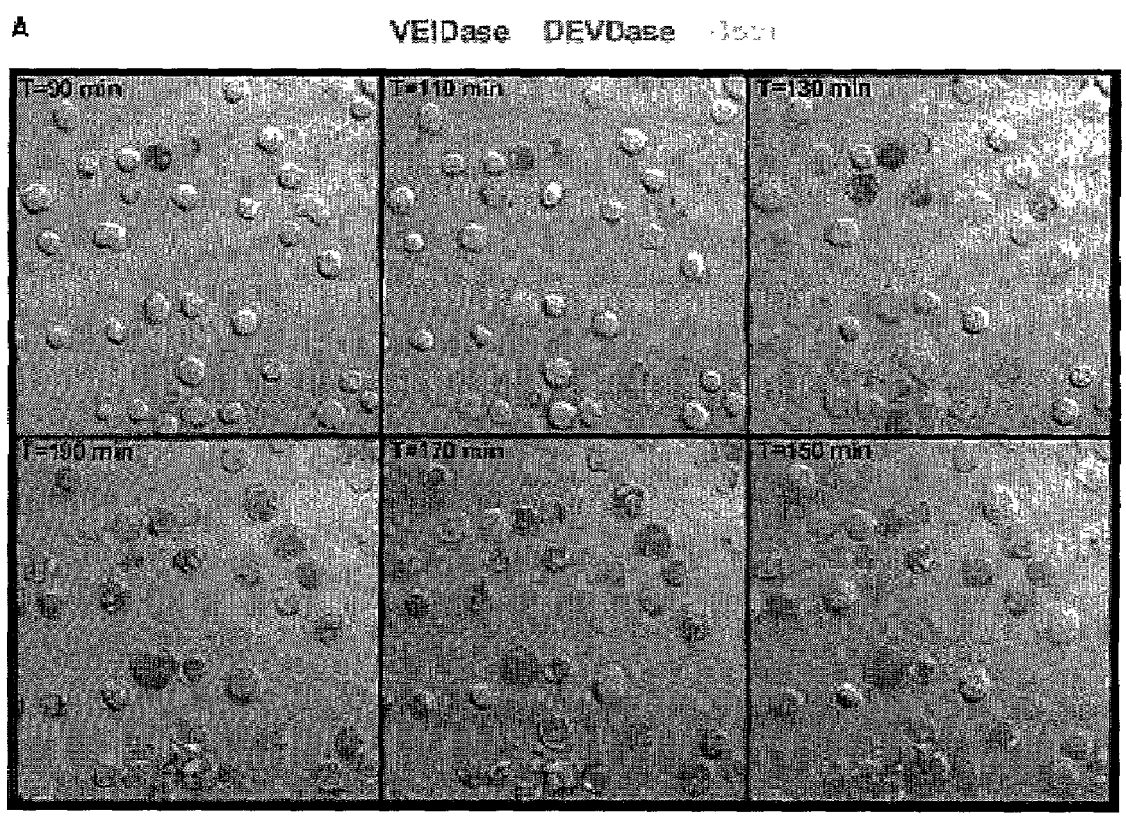
FIGS. 7A through 7C show confocal microscopy images of dexamethasonetreated thymocytes.
Figure 7B:
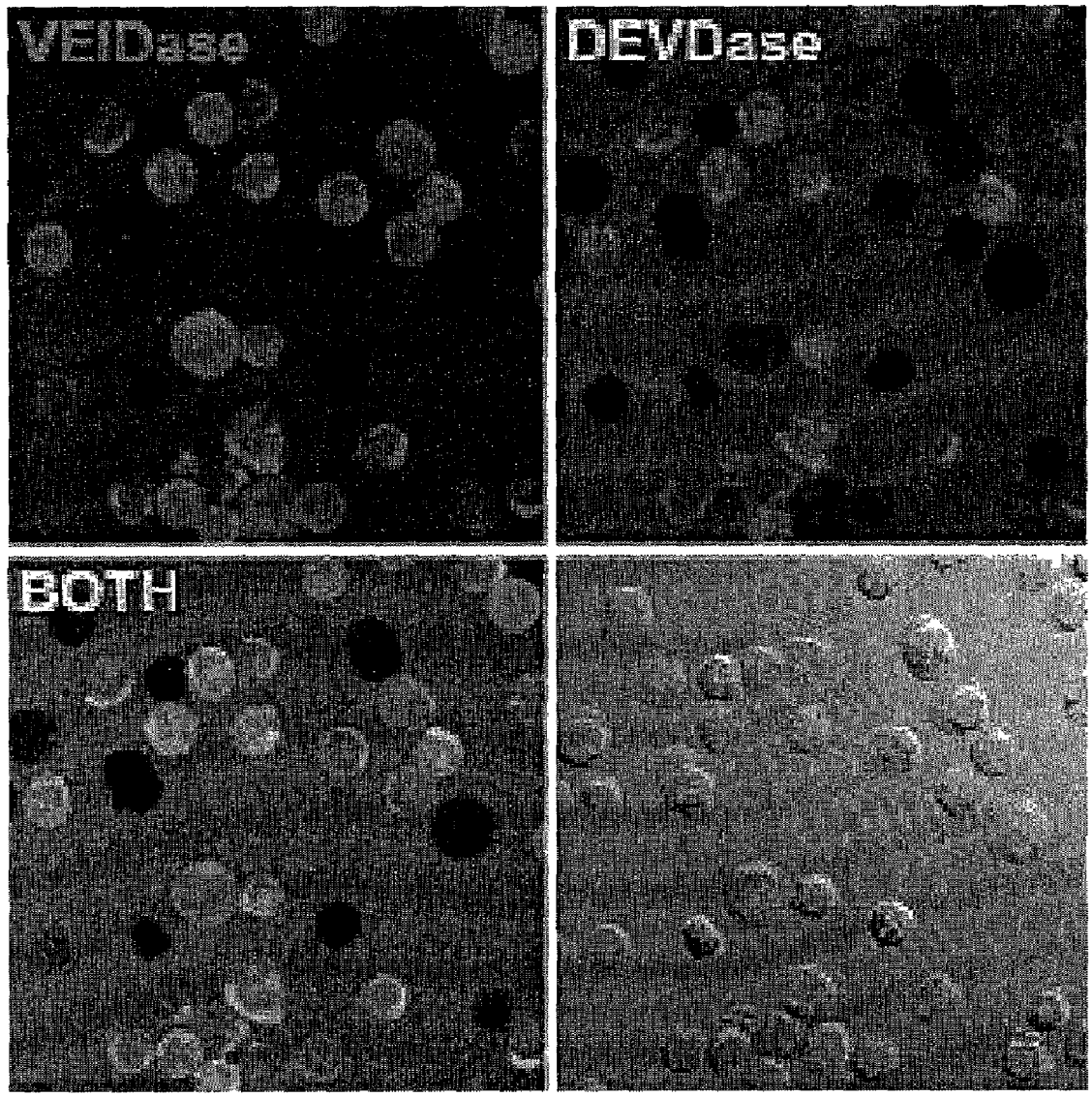
Figure 7C:
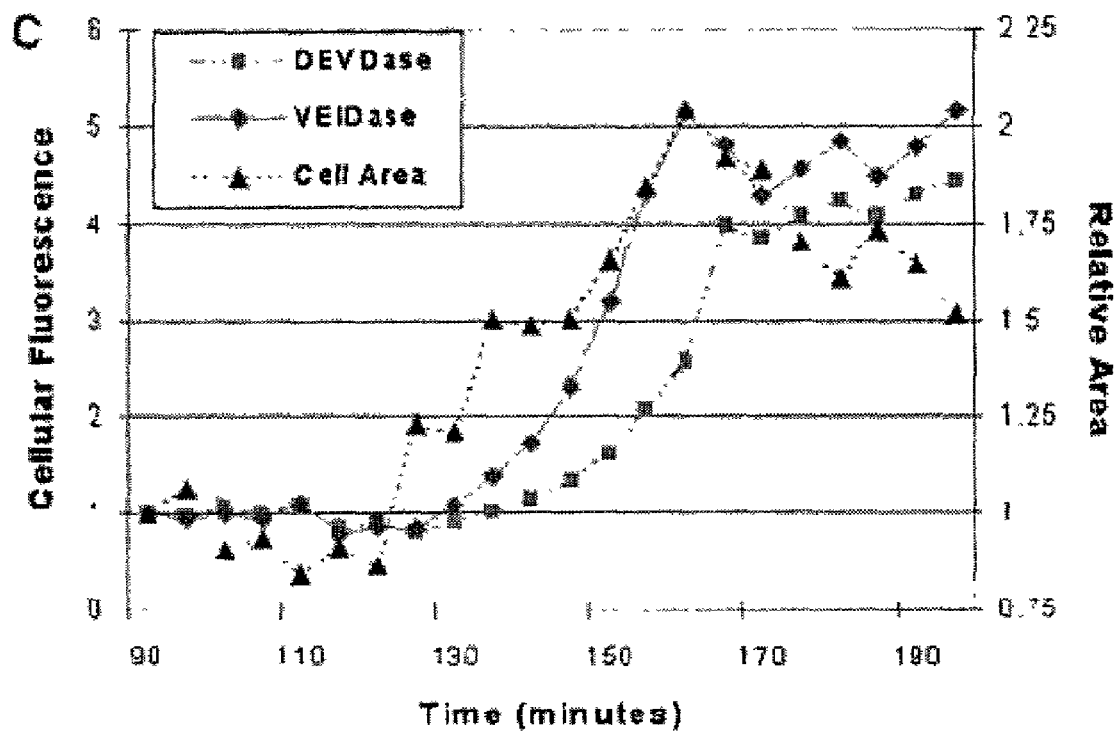
Figure 7C:

Because two recent studies with apoptotic Jurkat cell lysates showed that procaspase 6 was activated by caspase 3 (6, 7), the observation that VEIDase activity increased before the DEVDase activity in dexamethasonetreated thymocytes (FIG. 6A) was unexpected. The relative order of appearance of these two activities was addressed using con focal microscopy with cells continuously exposed to a mixture of the VEID and DEVD substrates derivatized with rhodamine green and tetramethyl rhodamine fluorophores, respectively, with dexamethasone added along with the substrates at time zero. Confocal images of these thymocytes at 20 min intervals are shown in FIG. 7A. The initial color appearing in individual cells from 90 to 190 min is invariably the green VEIDase activity. With increasing time, this VEIDase activity is replaced by the yellow color, signifying the presence of both VEIDase and DEVDase activities. Cells appearing red, indicative of DEVDase activity without accompanying VEIDase activity, are not obvious in any images. Thus, this independent approach using confocal microscopy confirms the VEIDase before DEVDase order found by flow cytometry for this apoptotic system. FIG. 7B also shows the separate images used to construct the frames of FIG. 7A, illustrating the distribution of fluorescent enzymatic products within these apoptotic thymocytes. It can be seen that the cells in the lower left panel with green VEIDase activity that have not yet become positive for red DEVDase display a relatively uniform distribution of fluorescence throughout the cells. However, those cells that have also become DEVDase positive and have therefore been VEIDase positive for some time appear yellow due to the accumulation of the green as well as red enzymatic products in cytoplasmic organelles. These more intensely stained cells seem likely to account for the highest intensity peak of VEIDase activity in FIG. 6A. FIG. 7C shows the result of quantitatively analyzing a representative individual cell from these confocal images. When examined on a frame by frame basis, the green and red fluorescent signals have distinct patterns of increase that cannot be accounted for by assuming that the red DEVDase activity is based on a less sensitive detection of the VEIDase activity.

Further examination of the images in FIG. 7 reveals an apparent size increase as the cells become caspase positive. This is best seen by finding a green cell in one frame of FIG. 7A and following it backward with time in the frames shown. In every case, the Nomarski images show that before becoming caspase positive, the thymocytes show a smaller diameter than the green (VEIDase only) cells. It appears in FIG. 7A that the yellow cells at 190 min may also be smaller than they were when they were green in earlier frames. Nomarski images of some of these large cells are suggestive of blebbing, with smooth round membranes. When projected as a timelapse sequence of Nomarski images without fluorescence overlay, the membranes and cytoplasmic organelles appear in vigorous motion suggestive of zeiosis (25; data not shown). FIG. 7C quantitates the size increase of one apoptotic thymocyte in this experiment, and shows that the onset of this increase precedes the appearance of caspase cleavage products. The increase in diameter seen in confocal images appears to be reflected in the small shift to the right in the forward scatter peak at 2 h as seen in FIG. 6A. This scatter shift was transient, as by 3 h or later the light scatter histogram returned nearly to that of the 1 h time point. It is only later, at 5-7 h, that the histograms show a peak of lower scattering particles building up that could be attributed to classical apoptotic cell shrinkage.

Pharmacological Target of ZVAD(OMe)FMK.

Figure 8:
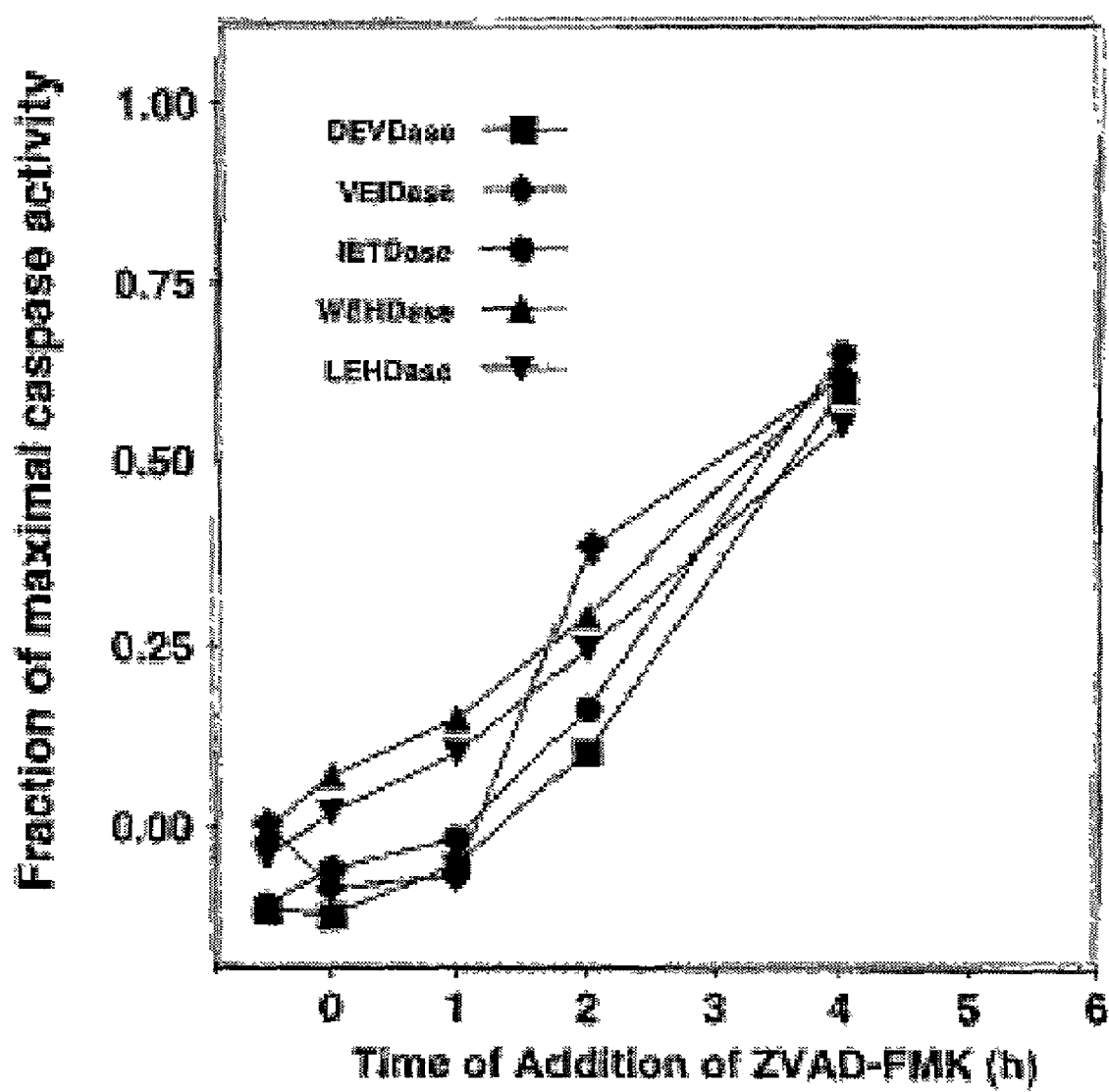
FIG. 8 shows the effect of ZVAD(OMe)FMK treatment on in situ caspase activation. Thymocytes were treated with 0.1 mM dexamethasone in vitro and analyzed after a total of 6 h incubation. The apoptosis inhibitor ZVAD(OMe)FMK was added at various times of incubation as indicated, and the caspase activities were assessed by flow cytometry. The results are expressed as ratios of mean fluorescence channel number comparing the activity in the presence of 50 mM ZVAD(OMe)FMK with the uninhibited sample for that substrate.

The ability to detect intracellular caspase activities allowed us to study the pharmacological target of the potent apoptosis inhibitor ZVAD(OMe)FMK. We have previously shown that ZVAD(OMe)FMK specifically blocks the appearance of dexamethasoneinduced apoptotic nuclear morphology and thymocyte death in vitro (26). In this experiment, we sought to identify which intracellular caspases were inactivated by ZVAD(OMe)FMK treatment of thymocytes. To this end, we added ZVAD(OMe)FMK to thymocytes at various times relative to the addition of dexamethasone and then examined caspase activity by flow cytometry at 6 h. Activity was assessed by the mean fluorescence channel number of PInegative cells. FIG. 8 shows the results of this experiment, which confirms that the addition of ZVAD (OMe)FMK blocks apoptosis when added before or simultaneously with dexamethasone. However, when addition of this inhibitor was delayed, the intracellular activity of all caspases detected rose, with no significant selective depletion of activity. When ZVAD(OMe)FMK was added at 4 h, the observed activity at 6 h of all caspases was 70-80% of uninhibited levels. As seen in FIG. 8, the time course for development of ZVAD(OMe)FMK-resistant caspase activity is strikingly parallel for the different substrates, and the constant difference between the activity ratios of the different substrates are accounted for by the method used to define caspase positivity. When thymocytes were pretreated with ZVAD(OMe)FMK followed by washing before dexamethasone addition, minimal inhibition was seen (data not shown). As discussed below, these data provide no evidence for significant inactivation of any of the detectable intracellular caspases by ZVAD(OMe) treatment of intact cells, but do suggest that ZVAD(OMe)FMK blocks an upstream component in the caspase activation cascade.

Discussion

Intracellular Caspase Substrates.

The cellpermeable fluorogenic substrates used this study (Table 7) are based on peptides of 18 amino acids containing central optimal tetrapeptide caspase recognition/cleavage sequences, with two identical fluorophores covalently attached near their termini. Previous studies have shown that in solution such substituted peptides assume an ovalshaped structure due to the formation of intramolecular excitonic Hdimers between the two fluorophores (27, 28). In such rhodamine derivatized dimers, the fluorophore fluorescence is quenched 90-99%. When a protease cleaves the peptide backbone of this complex, the cyclic structure incorporating the fluorophores is broken and two highly fluorescent substituted peptide fragments are generated. A surprising finding has been that caspase substrates of this design are permeable to cell membranes, thus allowing reporting of a variety of intracellular environments. While normally peptides of z18 amino acids are impermeable to cells without a specialized means of transport, we speculate that the headtohead complex of rhodamine fluorophores forms a hydrophobic surface capable of interacting with lipid bilayers to allow passive diffusion of these substrates across the bilayer. After intracellular cleavage, the rate of diffusion of the peptide-fluorophore reaction products across the membrane is significantly reduced since they lack the large hydrophobic surface provided by the fluorophore-fluorophore dimer of the substrate. The intracellular fluorescent signal generated by these substrates is predominantly due to the accumulation of fluorescent peptide cleavage products. Until the apoptotic loss of membrane integrity, this fluorescent signal reflects a balance between the rate of substrate hydrolysis and the rate of loss of peptide hydrolysis products from the cell. Although analyzing intracellular caspase activities using such substrates lacks many of the advantages of traditional biochemical approaches (e.g., limited numbers of purified components in dilute solutions), the ability to assess enzymatic activity in intact cells avoids some of the potential artifacts of such approaches and provides an important opportunity to test molecular models in a physiologically meaningful setting (29).

In the above description of our results, we have been careful to avoid ascribing the enzymatic activities with particular substrates to individual caspases, even though the substrates have been designed based on optimal caspase recognition motifs (Table 7). An initial question arises as to whether the activities seen represent caspases, as cleavage at any peptide bond between the lysines will give a signal with these substrates. Candidate cytoplasmic proteases that could be responsible for cleavage of these substrates include lysosomal cathepsins, the proteasome, and calpain. FIG. 5 shows that activity on the DEVDase substrate in apoptotic thymocyte extracts is specifically blocked by inhibitors targeted to caspase 3/7. Moreover, HPLC analysis of fluoro phorebearing peptide substrate fragments from intracellular digestion in apoptotic thymocytes shows that the initial primary cleavage is at the expected P1 aspartate (data not shown). It is clear that all the activities detected are caspase dependent, since ZVAD(OMe)FMK blocks their appearance (FIG. 8) as well as other detectable manifestations of dexamethasoneinduced thymocyte apoptosis (26). Thus, we conclude that activity on these protease substrates in intact apoptotic cells reflects caspases as opposed to other possible intracellular proteases.

Since the demonstrated peptide cleavage selectivity with recombinant caspases is not absolute, and the in situ intracellular activities of individual caspases have not been tested, the attribution of the activities observed to particular caspases must be made cautiously. We have carried out experiments with several recombinant caspases (3 and 6) to assess the specificity of some of the substrates used here, in particular the VEIDase and DEVDase. We have found that the peptide substrates in Table 7 demonstrate a far greater caspase selectivity than the tetrapeptide AMC substrates.

Caspase Activities in Intact Cells.

Analysis of intracellular caspase activity in dexamethasoneinduced apoptotic thymocytes by flow cytometry (FIG. 6A) strikingly shows a "quantal" distribution of caspase activity, with cells having either a background level of fluorescence due to uncleaved substrate or a 40 fold higher level of fluorescence, with few cells at an intermediate level. This quantal higher fluorescence level can most simply be explained as that achieved as a balance between maximal substrate hydrolysis and leakage of the fluorescent products out of the cell. The activity histograms for VEIDase after dexamethasone treatment as well as all five activities after antiFas treatment become trimodal, with an additional higher peak. This higher peak appears to correlate with the accumulation of intense fluorescence within intracellular organelles as seen in the microscope. The heterogeneity of the intracellular and intercellular caspase activities observed with these intracellular substrates is a novel observation, not readily detectable with other methods of measuring caspase activities.

Our results show that after dexamethasone treatment there is a pattern of progressive caspase activation with time, as expected for the caspase cascade proposed from traditional biochemical studies. As shown in FIG. 6A, this progression begins with LEHDase, followed by WEHDase, VEIDase, IETDase, and DEVDase. These activities correspond to the optimal tetrapeptide recognition sequences for caspases 9, 1, 6, 8, and 3/7, respectively (Table 7), and this order of caspase activation for dexamethasonetreated thymocytes is reasonable when compared with recent studies with enzyme inhibitors (26) and caspase knockout mice. This death pathway requires Apaf1 (17) and caspase 9 (18) but is independent of caspases 1 and 3 (30, 31) and FADD (32). Our observation that the first detectable caspase signal is the LEHDase activity is consistent with caspase 9 activation as the initiator of the caspase cascade in these cells. Although WEHDase activity seen in FIG. 6A could be due to caspase 1, it could also be due to caspases 4 or 5 (2), or potentially to newly described members of the ICE subfamily. While caspase 1 is presumably not part of the apoptotic death pathway, it is possible that it is responsible for processing cytokines such as IL1b in the dying cells (33).

The order of caspase activation for antiFas-treated thymocytes (FIG. 6B) is less clearcut but distinctly different from dexamethasonetreated thymocytes. The initial activity increases are in the order IETDase, WEHDase, DEVDase, LEHDase, and VEIDase. Since IETDase is the preferred substrate for caspase 8, which is activated by FADDinduced aggregation of its proenzyme (34), its early activation is consistent with current ideas about this pathway. The late activation of LEHDase, the preferred substrate for caspase 9, is consistent with the minor role of the Bid/mitochondrial amplification loop in the Fas death pathway in thymocytes (20) and the activation of caspase 9 by downstream caspases.

Studies in other laboratories on the relative order of activation of caspases 3 and 6 have yielded conflicting results, and our data show clearly that even in the same cells different triggering signals result in a different relative order of activation of these downstream caspases. Our observation that VEIDase activity appears before DEVDase activity in dexamethasonetreated thymocytes was unexpected given the studies of Slee et al. (7), which provided clear evidence that caspase 3 activity is upstream of caspase 6. They used Western blots to examine caspase activation/processing initiated by cytochrome c in Jurkat extracts, a model we considered relevant to thymocytes treated with dexamethasone. The most compelling experiments were those in which removal of individual caspases from the extracts blocked activation of other caspases, and it was particularly striking that depletion of caspase 3 abolished the ability of cytochrome c to trigger the processing of caspase 6, placing caspase 3 upstream of caspase 6. This same order was deduced from studies of the Fas death pathway (6) and are compatible with our observations of this pathway in thymocytes. On the other hand, an earlier study showed that addition of purified caspase 6 to a nonapoptotic extract triggered the processing of caspases 3 and 7, whereas addition of purified caspase 3 or 7 to a nonapoptotic extract failed to trigger the processing of caspase 6 (4). These results suggest that caspase 6 is upstream of caspases 3 and 7. Recently, Xanthoudakis et al. assayed camptothecintreated Jurkat extracts for an enzyme with procaspase 3 processing activity and found that this substrate formed a complex with Hsp60 which was then processed by caspase 6 (5). These results also favor the activation of caspase 6 before caspase 3 in the cascade. Our results argue against a common downstream module of caspase activation, suggesting that different upstream caspases trigger distinct downstream activation pathways.

The Pharmacological Target of ZVAD(OMe)FMK.

The finding in FIG. 8 that ZVAD(OMe)FMK treatment of apoptotic cells fails to significantly inactivate detectable caspase activity was unexpected. This compound was synthesized as a stable substitute for the ICE inhibitor ZVAD FMK, which has a half-life of, 1 h in aqueous solution (35). It has been widely and successfully used to block apoptosis in vitro, and has shown potency in animal models for diseases involving apoptosis (21, 22). ZVAD(OMe)FMK should be membrane permeable since it lacks charges, but for it to inactivate caspases intracellular esterases are required to remove the ester, forming the active site reagent ZVADFMK. Since this inhibitor lacks a P4 amino acid and is a potent upstream blocker of apoptotic pathways triggered by both death domain receptors and apaf1 (36), it is widely assumed that ZVADFMK is a general inhibitor of caspases. A recent solution study showed that ZVADFMK indeed irreversibly inactivates all of the individual recombinant caspases 1-9, but with a 1,000 fold range in reaction rates (35). Caspases 1, 5, 8, and 9 show rapid inactivation, with a t½ of several seconds at 1 mM ZVADFMK, whereas caspases 2, 4, and 6 react two to three orders of magnitude more slowly. Since caspases 8 and 9 are the initial caspases in the two major triggering pathways, these results appeared to account for the potent antiapoptotic activity of ZVAD (OMe)FMK. Thus, we expected to find the LEHDase and WEHDase activities in apoptotic thymocytes inactivated by ZVAD(OMe)FMK treatment. In the experiment shown in FIG. 8, we measured intracellular caspase activities at 6 h, when all substrates showed substantial activity. ZVAD (OMe)FMK totally blocked the activation of all detectable caspases when added before or at the time of dexamethasone addition, but after these caspases were activated (e.g., at 4 h), addition of ZVAD(OMe)FMK blocked only a minor component of the activities attributable to newly activated enzymes. There was no clear indication of a selective caspase inactivation predicted by the differing reaction rates with ZVADFMK (35), suggesting that ZVAD(OMe)FMK acts upstream of the measured components of the caspase cascade. Extrapolating results from the biochemical study of ZVADFMK reactivity is difficult, as its cytoplasmic concentration is not known.

There are several possible explanations for our failure to observe inactivation by ZVAD(OMe)FMK of previously activated caspases. Although we believe it unlikely for the reasons discussed, it is possible we are not measuring the caspases these substrates were designed for, and that the LEHDase activity observed is not due to caspase 9. Another possibility is that the major intracellular caspase activities are within membranebound organelles (as suggested by the confocal images) and thus not accessible to the active hydrophilic ZVADFMK inhibitor in the cytoplasm. A third possibility is that ZVAD(OMe)FMK or ZVADFMK could be reacting with a critical caspase we have not measured, or perhaps a cysteine protease that is not a caspase. In this respect, it is worth noting that the cathepsin B inhibitor carbobenzoxyphenylalanylalanylfluoromethyl ketone (ZFAFMK) does not block dexamethasoneinduced thymocyte apoptosis (26), suggesting a P1 amino acid specificity for the pharmacological target of ZVAD(OMe)FMK. It is possible that ZVADFMK blocks the putative critical upstream aggregation induced autoactivation of procaspase 9. This autoactivation activity, involving processing near the active site cysteine when the proenzymes are part of a multimeric complex, is not understood in detail but is presumably not measurable with the present fluorogenic substrates. ZVADFMK may selectively target this activity (and the homologous autoactivation of procaspase 8) more efficiently than it inactivates the mature caspases.

Regardless of its precise molecular target, the results in FIG. 8 clearly indicate that ZVAD(OMe)FMK acts at an early stage in the apoptotic pathway, either by inactivating an upstream caspase or another activity. The inability of ZVAD(OMe)FMK to significantly block caspase activation if added before dexamethasone and then washed out indicates that this activity is silent before apoptosis is induced. We thus conclude that the pharmacological target of ZVAD (OMe)FMK has the following properties: (a) it is activated early in the apoptosis cascade; (b) it is a common element in apoptotic pathways induced by many diverse triggers; and (c) it has the reactivity of a cysteine protease with selectivity for a P1 aspartic acid.

We believe that the ability to monitor enzyme activities in intact functioning cells is an important component of our efforts to apply the knowledge of enzyme biochemistry to physiological systems. The caspase substrates described here provide the first attempt to use this approach for apoptosis, where there is ample evidence for the importance of cellular organization in regulating these critical proteolytic mediators. Given the widespread interest in selectively modulating apoptosis in vivo, we believe that these are useful tools that can be applied to a variety of other apoptotic systems.

REFERENCES

1. Yuan, J., S. Shaham, S. Ledoux, H. M. Ellis, and H. R. Horvitz. 1993. The *C. elegans* cell death gene ced3 encodes a protein similar to mammalian interleukin 1b converting enzyme. *Cell.* 75:641-652.

2. Thornberry, N. A., T. A. Rano, E. P. Peterson, D. M. Rasper, T. Timkey, M. GarciaCalvo, V. M. Houtzager, P. A. Nordstrom, S. Roy, J. P. Vaillancourt, et al. 1997. A combinatorial approach defines specificities of members of the caspase family and granzyme B. Functional relationships established for key mediators of apoptosis. *J. Biol. Chem.* 272:17907-17911.

3. Rodriguez, J., and Y. Lazebnik. 1999. Caspase9 and APAF1 form an active holoenzyme. *Genes Dev.* 13:3179-3184.

4. Orth, K., K. O'Rourke, G. S. Salvesen, and V. M. Dixit. 1996. Molecular ordering of apoptotic mammalian CED3/ICElike proteases. *J. Biol. Chem.* 271:20977-20980.

5. Xanthoudakis, S., S. Roy, D. Rasper, T. Hennessey, Y. Aubin, R. Cassady, P. Tawa, R. Ruel, A. Rosen, and D. W. Nicholson. 1999. Hsp60 accelerates the maturation of procaspase 3 by upstream activator proteases during apoptosis. *EMBO (Eur. Mol. Biol. Organ.) J.* 18:2049-2056.

6. Hirata, H., A. Takahashi, S. Kobayashi, S. Yonehara, H. Sawai, T. Okazaki, K. Yamamoto, and M. Sasada. 1998. Caspases are activated in a branched protease cascade and control distinct downstream processes in fas-induced apoptosis. *J. Exp. Med.* 187:587-600.

7. Slee, E. A., M. T. Harte, R. M. Kluck, B. B. Wolf, C. A. Casiano, D. D. Newmeyer, H. G. Wang, J. C. Reed, D. W. Nicholson, E. S. Alnemri, et al. 1999. Ordering the cytochrome c-initiated caspase cascade: hierarchical activation of caspases-2, -3, -6, -7, -8, and -10 in a caspase-9-dependent manner. *J. Cell Biol.* 144:281-292.

8. Bossy-Wetzel, E., D. D. Newmeyer, and D. R. Green. 1998. Mitochondrial cytochrome c release in apoptosis occurs upstream of DEVD-specific caspase activation and independently of mitochondrial transmembrane depolarization. *EMBO (Eur. Mol. Biol. Organ.) J.* 17:37-49.

9. Susin, S. A., H. K. Lorenzo, N. Zamzami, I. Marzo, B. E. Snow, G. M. Brothers, J. Mangion, E. Jacotot, P. Costantini, M. Loeffler, et al. 1999. Molecular characterization of mitochondrial apoptosis-inducing factor. *Nature.* 397: 441-446.

10. Mancini, M., D. W. Nicholson, S. Roy, N. A. Thornberry, E. P. Peterson, L. A. Casciola-Rosen, and A. Rosen. 1998. The caspase-3 precursor has a cytosolic and mitochondrial distribution: implications for apoptotic signaling. *J. Cell Biol.* 140:1485-1495.

11. Susin, S. A., H. K. Lorenzo, N. Zamzami, I. Marzo, C. Brenner, N. Larochette, M. C. Prevost, P. M. Alzari, and G. Kroemer. 1999. Mitochondrial release of caspase-2 and -9 during the apoptotic process. *J. Exp. Med.* 189:381-394.

12. Nechushtan, A., C. L. Smith, Y. T. Hsu, and R. J. Youle. 1999. Conformation of the Bax C-terminus regulates subcellular location and cell death. *EMBO (Eur. Mol. Biol. Organ.) J.* 18:2330-2341.

13. Packard, B. Z., D. D. Toptygin, A. Komoriya, and L. Brand. 1997. Design of profluorescent protease substrates guided by exciton theory. *Methods Enzymol.* 278:15-23.

14. Packard, B. Z., D. D. Toptygin, A. Komoriya, and L. Brand. 1996. Profluorescent protease substrates: intramolecular dimers described by the exciton model. *Proc. Natl. Acad. Sci. USA.* 93:11640-11645.

15. Packard, B. Z., D. D. Toptygin, A. Komoriya, and L. Brand. 1997. Characterization of fluorescence quenching in bifluorophoric protease substrates. *Biophys. Chem.* 67:167-176.

16. Packard, B. Z., D. D. Toptygin, A. Komoriya, and L. Brand. 1998. Intramolecular resonance dipole-dipole interactions in a protease substrate. *J. Phys. Chem. B.* 102:752-758.

17. Yoshida, H., Y. Y. Kong, R. Yoshida, A. J. Elia, A. Hakem, R. Hakem, J. M. Penninger, and T. W. Mak. 1998. Apaf1 is required for mitochondrial pathways of apoptosis and brain development. *Cell.* 94:739-750. 18. Hakem, R., A. Hakem, G. S. Duncan, J. T. Henderson, M. Woo, M. S. Soengas, A. Elia, J. L. de la Pompa, D. Kagi, W. Khoo, et al. 1998. Differential requirement for caspase 9 in apoptotic pathways in vivo. *Cell.* 94:339-352.

19. Zhang, J., D. Cado, A. Chen, N. H. Kabra, and A. Winoto. 1998. Fas-mediated apoptosis and activation-induced T-cell proliferation are defective in mice lacking FADD/Mort1. *Nature.* 392:296-300.20. Yin, X. M., K. Wang, A. Gross, Y. Zhao, S. Zinkel, B. Klocke, K. A. Roth, and S. J. Korsmeyer. 1999. Bid-deficient mice are resistant to Fas-induced hepatocellular apoptosis. *Nature.* 400:886-891.

21. Rodriguez, I., K. Matsuura, C. Ody, S. Nagata, and P. Vas salli. 1996. Systemic injection of a tripeptide inhibits the intracellular activation of CPP32-like proteases in vivo and fully protects mice against Fas-mediated fulminant liver destruction and death. *J. Exp. Med.* 184:2067-2072.

22. Hara, H., R. M. Friedlander, V. Gagliardini, C. Ayata, K. Fink, Z. Huang, M. Shimizu-Sasamata, J. Yuan, and M. A. Moskowitz. 1997. Inhibition of interleukin 11 beta converting enzyme family proteases reduces ischemic and excitotoxic neuronal damage. *Proc. Natl. Acad. Sci. USA.* 94:2007-2012.

23. Enari, M., R. V. Talanian, W. W. Wong, and S. Nagata. 1996. Sequential activation of ICE-like and CPP32-like proteases during Fas-mediated apoptosis. *Nature.* 380:723-726.

24. Nicholson, D. W., A. Ali, N. A. Thornberry, J. P. Vaillancourt, C. K. Ding, M. Gallant, Y. Gareau, P. R. Griffin, M. Labelle, Y. A. Lazebnik, et al. 1995. Identification and inhibition of the ICE/CED-3 protease necessary for mammalian apoptosis. *Nature.* 376:37-43.

25. Majno, G., and I. Joris. 1995. Apoptosis, oncosis, and necrosis. An overview of cell death. *Am. J. Pathol.* 146:3-15. 26. Sarin, A., M. L. Wu, and P. A. Henkart. 1996. Different ICE-family protease requirements for the apoptotic death of T lymphocytes triggered by diverse stimuli. *J. Exp. Med.* 184: 2445-2450.

27. Packard, B. Z., A. Komoriya, D. D. Toptygin, and L. Brand. 1997. Structural characteristics of fluorophores which form intramolecular H-type dimers in a protease substrate. *J. Phys. Chem. B.* 101:50705074.

28. Packard, B. Z., A. Komoriya, V. Nanda, and L. Brand. 1998. Intramolecular excitonic dimers in protease substrates: modification of the backbone moiety to probe the H-dimer structure. *J. Phys. Chem. B.* 102:18201827.

29. Weng, G., U. S. Bhalla, and R. Iyengar. 1999. Complexity in biological signaling systems. *Science.* 284:92-96.

30. Kuida, K., J. A. Lippke, G. Ku, M. W. Harding, D. J. Livingston, M. S. S. Su, and R. A. Flavell. 1995. Altered cytokine export and apoptosis in mice deficient in interleukin-1b converting enzyme. *Science.* 267:2000-2003.

31. Kuida, K., T. S. Zheng, S. Na, C. Kuan, D. Yang, H. Karasuyama, P. Rakic, and R. A. Flavell. 1996. Decreased apoptosis in the brain and premature lethality in CPP32-deficient mice. *Nature.* 384:368-372.

32. Zornig, M., A. O. Hueber, and G. Evan. 1998. p53-dependent impairment of T-cell proliferation in FADD dominant-negative transgenic mice. *Curr. Biol.* 8:467470.

33. Miwa, K., M. Asano, R. Horai, Y. Iwakura, S. Nagata, and T. Suda. 1998. Caspase 1-independent IL-11 beta release and inflammation induced by the apoptosis inducer Fas ligand. *Nat. Med.* 4:1287-1292.

34. Wallach, D., E. E. Varfolomeev, N. L. Malinin, Y. V. Goltsev, A. V. Kovalenko, and M. P. Boldin. 1999. Tumor necrosis factor receptor and Fas signaling mechanisms. *Annu. Rev. Immunol.* 17:331-367.

35. Garcia-Calvo, M., E. P. Peterson, B. Leiting, R. Ruel, D. W. Nicholson, and N. A. Thornberry. 1998. Inhibition of human caspases by peptide-based and macromolecular inhibitors. *J. Biol. Chem.* 273:32608-32613.

36. Slee, E. A., H. J. Zhu, S. C. Chow, M. MacFarlane, D. W. Nicholson, and G. M. Cohen. 1996. Benzyloxycarbonyl-Val-Ala-Asp (OMe) fluoromethylketone (Z-VAD.FMK) inhibits apoptosis by blocking the processing of CPP32. *Biochem. J.* 315:21-24.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A fluorogenic composition for the detection of the activity of a protease, said composition having the formula:

$$F^1\text{-}aa^1_j\text{-}(aa^2\text{-}aa^3)_k\text{-}aa^4_l\text{-}aa^5\text{-}X_m\text{-}P\text{-}Y_n\text{-}aa^6\text{-}aa^7_o\text{-}(aa^8\text{-}aa^9)_p\text{-}aa^{10}_q\text{-}F^2$$
$$|\quad\quad\quad\quad\quad\quad\quad\quad\quad\quad\quad\quad\quad\quad\quad\quad\quad\quad\quad\quad\quad\quad\quad\quad\quad\quad|$$
$$(S^1)_i\quad\quad\quad\quad\quad\quad\quad\quad\quad\quad\quad\quad\quad\quad\quad\quad\quad\quad\quad\quad\quad\quad(S^2)_r$$

wherein, P is a peptide consisting of the amino acid sequence YVHDAPV (SEQ ID NO:210);

$F^1$ and $F^2$ are fluorophores and $F^1$ is attached to the amino terminal amino acid and $F^2$ is attached to the carboxyl terminal amino acid;

$S^1$ and $S^2$, when present, are peptide spacers ranging in length from 1 to about 50 amino acids and $S^1$, when present, is attached to the amino terminal amino acid and $S^2$, when present, is attached to the carboxyl terminal amino acid;

i, j, k, l, m, n, o, p, q, and r are independently 0 or 1;

$aa^1$ and $aa^{10}$ are independently selected from the group consisting of lysine, ornithine and cysteine;

-$aa^2$-$aa^3$-, and -$aa^8$-$aa^9$- are independently selected from the group consisting of an amino acid or a dipeptide where said amino acid or dipeptide consist of amino acids selected from the group consisting of Asp, Glu, Lys, Ornithine, Arg, Citulline, homocitrulline, Ser, homoserine, Thr, and Tyr;

$aa^5$, $aa^4$, $aa^6$, and $aa^7$ are independently selected from the group consisting of proline, 3,4-dehydroproline, hydroxyproline, alpha aminoisobutyric acid and N-methyl alanine;

X is selected from the group consisting of Gly, βAla, γAbu, Gly-Gly, Ahx, βAla-Gly, βAla-βAla, γAbu-Gly, βAla-γAbu, Gly-Gly-Gly, γAbu-γAbu, Ahx-Gly, βAla-Gly-Gly, Ahx-βAla, βAla-βAla-Gly, Gly-Gly-Gly-Gly, (SEQ ID NO:211), Ahx-γAbu, βAla-βAla-βAla, γAbu-βAla-Gly, γAbu-γAbu-Gly, Ahx-Ahx, γAbu-γAbu-βAla, and Ahx-Ahx-Gly;

Y is selected from the group consisting of Gly, βAla, γAbu, Gly-Gly, Ahx, Gly-βAla, βAla-βAla, Gly-γAbu, γAbu-βAla, Gly-Gly-Gly, γAbu-γAbu, Gly-Ahx, Gly-Gly-βAla, βAla-Ahx, Gly-βAla-βAla, Gly-Gly-Gly-Gly (SEQ ID NO: 211), γAbu-Ahx, βAla-βAla-βAla, Gly-βAla-γAbu, Gly-γAbu-γAbu, Ahx-Ahx, βAla-γAbu-γAbu, and Gly-Ahx-Ahx; and when i is 1, $S^1$ is joined to $aa^1$ by a peptide bond through a terminal alpha amino group of $aa^1$; and when r is 1, $S^2$ is joined to $aa^{10}$ by a peptide bond through a terminal alpha carboxyl group of $aa^{10}$.

2. The composition of claim 1, wherein the carboxyl terminal amino acid in which the carboxylic acid group is replaced with an amide.

3. The composition of claim 1, wherein:

r is zero; and $aa^{10}$ has a C-teminal amide group or free carboxylic acid group.

4. The composition of claim 1, comprising an amino acid sequence selected from the group consisting of KDPJGYVHDAPVGJPKGY, KDPJGYVHDAPVPKGY (SEQ ID NO:171), and KDPYVHDAPVGJPKGY (SEQ ID NO:172).

5. The composition of claim 4, wherein said composition has a terminal blocking group.

6. The composition of claim 4, wherein said composition has a terminal 9-fluoreneacetyl (Fa) group.

7. The composition of claim 4, wherein said composition has a terminal 9-fluorenylmethoxycarbonyl (Fmoc) group.

8. The composition of claim 1, wherein $F^1$ and $F^2$ are the same fluorophore.

9. The composition of claim 8, wherein said $F^1$ and $F^2$ have an excitation wavelength between about 315 nm and about 800 nm.

10. The composition of claim 8, wherein said composition bears a hydrophobic group.

11. The composition of claim 1, wherein the $F^1$ molecule is attached through either an α-amino group of the $aa^1$ amino acid or through a side chain amino group of the aa¹ amino acid, or through a sulfhydryl group of a side chain of the aa¹ amino acid.

12. The composition of claim 1, wherein the $F^2$ molecule is attached either through a side chain amino group of the $aa^{10}$ amino acid, through a carboxyl group of the $aa^{10}$ amino acid, or through a sulfhydryl group of a side chain of the $aa^{10}$ amino acid.

13. The composition of claim 1, wherein said fluorophore is selected from the group consisting of rhodamine X, 9-(2,5-dicarboxyphenyl)-3,6-bis(dimethylamino)xanthyliumhalide or other anion, 9-(2,6-dicarboxyphenyl)-3,6-bis(dimethylamino)xanthyliumhalide or other anion, 9-(2,5)-dicarboxyphenyl)-2,7-dimethyl-3,6-bis(ethylamino) xanthylium halide or other anion (Rh6G), 9-(2,6)-dicarboxyphenyl)-2,7-dimethyl-3,6-bis(ethylamino) xanthylium halide or other anion, 9-(2,5-dicarboxyphenyl)-3,6-bisamino-xanthylium halide or other anion (Rh110), 9-(2,6-dicarboxyphenyl)-3,6-bisamino-xanthylium halide or other anion (Rh110), 9-(2,5-dicarboxyphenyl)-3-amino-6-hydroxy-xanthylium halide or other anion (Blue Rh), 9-(2, 6-dicarboxyphenyl)-3-amino-6-hydroxy-xanthylium halide or other anion (Blue Rh), carboxytetramethylrhodamine, carboxyrhodamine-X, diethylaminocoumarin, 9-(2,5-dicarboxyphenyl)-3,6-bis-(dimethylamino)xanthylium chloride (5-TMR), 9-(2,6-dicarboxyphenyl)-3,6-bis-(dimethylamino)xanthylium chloride (6-TMR), 9-(2-carboxyphenyl)-2,7-dimethyl-3,6-bis(ethylamino)xanthylium, 9-(2-carboxyphenyl)-3,6-bis(dimethylamino)xanthylium, and 9-(2-carboxyphenyl)-xanthylium.

14. The composition of claim 1, wherein said fluorophore comprises a carbocyanine dye.

15. The composition of claim 1, wherein said composition bears a hydrophobic group.

16. The composition of claim 15, wherein said hydrophobic group is selected from the group consisting of: Fmoc, 9-fluoreneacetyl group (Fa), 1-fluorenecarboxylic group, 9-fluorenecarboxylic group, and 9-fluorenone-1-carboxylic group, benzyloxycarbonyl, Xanthyl (Xan), Trityl (Trt), 4-methyltrityl (Mtt), 4-methoxytrityl (Mint), 4-methoxy-2, 3,6-trimethyl-benzenesulphonyl (Mtr), Mesitylene-2-sulphonyl (Mts), Tosyl (Tos), 4,4-dimethoxybenzhydryl (Mbh), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridine-sulphenyl (Npys), 1-(4,4-dimethyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA).

17. The composition of claim 16, wherein said hydrophobic group is Fmoc.

18. The composition of claim 16, wherein said hydrophobic group is Fa.

19. The composition of claim 16, wherein said hydrophobic group is attached to the amino terminus of the molecule.

20. A fluorogenic composition for the detection of the activity of a protease, said composition having the formula:

$$F^1\text{-}aa^1_j\text{-}(aa^2\text{-}aa^3)_k\text{-}aa^4_l\text{-}aa^5\text{-}X_m\text{-}P\text{-}Y_n\text{-}aa^6\text{-}aa^7_o\text{-}(aa^8\text{-}aa^9)_p\text{-}aa^{10}_q\text{-}F^2$$
$$\phantom{F^1\text{-}aa^1_j}|\phantom{\text{-}(aa^2\text{-}aa^3)_k\text{-}aa^4_l\text{-}aa^5\text{-}X_m\text{-}P\text{-}Y_n\text{-}aa^6\text{-}aa^7_o\text{-}(aa^8\text{-}aa^9)_p\text{-}aa^{10}_q}|$$
$$\phantom{F^1\text{-}}(S^1)_i\phantom{aaaaaaaaaaaaaaaaaaaaaaaaaaaaaaaaaa}(S^2)_r$$

wherein, P is a peptide selected from the group consisting YVHDAPV (SEQ ID NO:216), and (dY)VHDAPV (SEQ ID NO:217);

$F^1$ and $F^2$ are fluorophores and $F^1$ is attached to the amino terminal amino acid and $F^2$ is attached to the carboxyl terminal amino acid;

$S^1$ and $S^2$, when present, are peptide spacers ranging in length from 1 to about 50 amino acids and $S^1$, when present, is attached to the amino terminal amino acid and $S^2$, when present, is attached to the carboxyl terminal amino acid;

i, j, k, l, m, n, o, p, q, and r are independently 0 or 1;

$aa^1$ and $aa^{10}$ are independently selected from the group consisting of lysine, ornithine and cysteine;

-$aa^2$-$aa^3$-, and -$aa^8$-$aa^9$- are independently selected from the group consisting of an amino acid or a dipeptide where said amino acid or dipeptide consist of amino acids selected from the group consisting of Asp, Glu, Lys, Ornithine, Arg, Citulline, homocitrulline, Ser, homoserine, Thr, and Tyr;

$aa^5$, $aa^4$, $aa^6$, and $aa^7$ are independently selected from the group consisting of proline, 3,4-dehydroproline, hydroxyproline, alpha aminoisobutyric acid and N-methyl alanine;

X is selected from the group consisting of Gly, βAla, γAbu, Gly-Gly, Ahx, βAla-Gly, βAla-βAla, γAbu-Gly, βAla-γAbu, Gly-Gly-Gly, γAbu-γAbu, Ahx-Gly, βAla-Gly-Gly, Ahx-βAla, βAla-βAla-Gly, Gly-Gly-Gly-Gly, (SEQ ID NO:211), Ahx-γAbu, βAla-βAla-βAla, γAbu-βAla-Gly, γAbu-γAbu-Gly, Ahx-Ahx, γAbu-γAbu-βAla, and Ahx-Ahx-Gly;

Y is selected from the group consisting of Gly, βAla, γAbu, Gly-Gly, Ahx, Gly-βAla, βAla-βAla, Gly-γAbu, γAbu-βAla, Gly-Gly-Gly, γAbu-γAbu, Gly-Ahx, Gly-Gly-βAla, βAla-Ahx, Gly-βAla-βAla, Gly-Gly-Gly-Gly (SEQ ID NO: 211), γAbu-Ahx, βAla-βAla-βAla, Gly-βAla-γAbu, Gly-γAbu-γAbu, Ahx-Ahx, βAla-γAbu-γAbu, and Gly-Ahx-Ahx; and when i is 1, $S^1$ is joined to $aa^1$ by a peptide bond through a terminal alpha amino group of $aa^1$; and when r is 1, $S^2$ is joined to $aa^{10}$ by a peptide bond through a terminal alpha carboxyl group of $aa^{10}$.

21. The composition of claim 20, wherein the carboxyl terminal amino acid in which the carboxylic acid group is replaced with an amide.

22. The composition of claim 20, wherein:
r is zero; and
$aa^{10}$ has a C-teminal amide group or free carboxylic acid group.

23. The composition of claim 20, comprising an amino acid sequence selected from the group consisting of KDBYVHDAPVPKGY (SEQ ID NO:218), KDBGYVHDAPVGPKGY (SEQ ID NO:219), KDBJGYVHDAPVGJPKGY (SEQ ID NO:220), and KDBJG(dY)VHDAPVGJPKGY (SEQ ID NO:221).

24. The composition of claim 23, wherein said composition has a terminal blocking group.

25. The composition of claim 23, wherein said composition has a terminal Fa group.

26. The composition of claim 23, wherein said composition has a terminal Fmoc group.

27. The composition of claim 20, wherein $F^1$ and $F^2$ are the same fluorophore.

28. The composition of claim 27, wherein $F^1$ and $F^2$ have an excitation wavelength between about 315 nm and about 800 nm.

29. The composition of claim 20, wherein the $F^1$ molecule is attached through either an α-amino group of the $aa^1$ amino acid or through a side chain amino group of the $aa^1$ amino acid, or through a sulfhydryl group of a side chain of the $aa^1$ amino acid.

30. The composition of claim 20, wherein the $F^2$ molecule is attached either through a side chain amino group of the $aa^{10}$ amino acid, through a carboxyl group of the $aa^{10}$ amino acid, or through a sulfhydryl group of a side chain of the $aa^{10}$ amino acid.

31. The composition of claim 20, wherein said fluorophore is selected from the group consisting of rhodamine X, 9-(2,5-dicarboxyphenyl)-3,6-bis(dimethylamino)xanthyliumhalide or other anion, 9-(2,6-dicarboxyphenyl)-3,6-bis(dimethylamino)xanthyliumhalide or other anion, 9-(2,5)-dicarboxyphenyl)-2,7-dimethyl-3,6-bis(ethylamino) xanthylium halide or other anion (Rh6G), 9-(2,6)-dicarboxyphenyl)-2,7-dimethyl-3,6-bis(ethylamino) xanthylium halide or other anion, 9-(2,5-dicarboxyphenyl)-3,6-bisamino-xanthylium halide or other anion (Rh110), 9-(2,6-dicarboxyphenyl)-3,6-bisamino-xanthylium halide or other anion (Rh110), 9-(2,5-dicarboxyphenyl)-3-amino-6-hydroxy-xanthylium halide or other anion (Blue Rh), 9-(2,6-dicarboxyphenyl)-3-amino-6-hydroxy-xanthylium halide or other anion (Blue Rh), carboxytetramethyirhodamine, carboxyrhodamine-X, diethylaminocoumarin, 9-(2,5-dicarboxyphenyl)-3,6-bis-(dimethylamino)xanthylium chloride (5-TMR), 9-(2,6-dicarboxyphenyl)-3,6-bis-(dimethylamino)xanthylium chloride (6-TMR), 9-(2-carboxyphenyl)-2,7-dimethyl-3,6-bis(ethylamino)xanthylium, 9-(2-carboxyphenyl)-3,6-bis(dimethylamino)xanthylium, and 9-(2-carboxyphenyl)-xanthylium.

32. The composition of claim 20, wherein said fluorophore comprises a carbocyanine dye.

33. The composition of claim 20, wherein said composition bears a hydrophobic group.

34. The composition of claim 33, wherein said hydrophobic group is selected from the group consisting of: Fmoc, 9-fluoreneacetyl group (Fa), 1-fluorenecarboxylic group, 9-fluorenecarboxylic group, and 9-fluorenone-1-carboxylic group, benzyloxycarbonyl, Xanthyl (Xan), Trityl (Trt), 4-methyltrityl (Mtt), 4-methoxytrityl (Mint), 4-methoxy-2,3,6-trimethyl-benzenesulphonyl (Mtr), Mesitylene-2-sulphonyl (Mts), Tosyl (Tos), 4,4-dimethoxybenzhydryl (Mbh), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridine-sulphenyl (Npys), 1-(4,4-dimethyl-2,6-diaxocyclohexylidene)ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA).

35. The composition of claim 34, wherein said hydrophobic group is Fmoc.

36. The composition of claim 34, wherein said hydrophobic group is Fa.

37. The composition of claim 34, wherein said hydrophobic group is attached to the amino terminus of the molecule.

\* \* \* \* \*

SEQUENCE LISTING

```
<160> NUMBER OF SEQ ID NOS: 221

<210> SEQ ID NO 1
<211> LENGTH: 9
<212> TYPE: PRT
<213> ORGANISM: Artificial Sequence
<220> FEATURE:
<223> OTHER INFORMATION: protease indicator
<221> NAME/KEY: misc_feature
<222> LOCATION: (5)..(5)
<223> OTHER INFORMATION: Xaa is norleucine (Nle)

<400> SEQUENCE: 1

Asn Ala Ile Pro Xaa Ser Ile Pro Cys
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib or Pro

<400> SEQUENCE: 2

Lys Asp Xaa Thr Gly Arg Thr Gly Pro Lys Gly Tyr
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide substrate
<221> NAME/KEY: Artificial
<222> LOCATION: (1)..(14)
<223> OTHER INFORMATION: Artificial protease substrate

<400> SEQUENCE: 3

Lys Asp Pro Pro Thr Gly Arg Thr Gly Pro Pro Lys Gly Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib or Pro
```

-continued

```
<400> SEQUENCE: 4

Lys Asp Xaa Asp Glu Val Asp Gly Ile Asp Pro Lys Gly Tyr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib or Pro

<400> SEQUENCE: 5

Lys Asp Xaa Asp Glu Val Asn Gly Ile Asp Pro Lys Gly Tyr
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib or Pro

<400> SEQUENCE: 6

Lys Asp Xaa Glu Val Asp Gly Ile Asp Pro Lys Gly Tyr
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (4)..(4)
<223> OTHER INFORMATION: X is Aib or Pro

<400> SEQUENCE: 7

Lys Asp Tyr Xaa Ala Asp Gly Ile Asp Pro Lys Gly Tyr
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: BLOCKED WITH FMOC
<221> NAME/KEY: MOD_RES
<222> LOCATION: (3)..(3)
<223> OTHER INFORMATION: X is Aib or Pro

<400> SEQUENCE: 8

Lys Asp Xaa Asp Glu Val Asp Gly Ile Asp Pro Lys Gly Tyr
1               5                   10

<210> SEQ ID NO 9
<211> LENGTH: 14
<212> TYPE: PRT
<213> ORGANISM: Artificial Sequence
<220> FEATURE:
```

```
<223> OTHER INFORMATION: Synthetic peptide substrate
<221> NAME/KEY: MOD_RES
<222> LOCATION: (1)..(1)
<223> OTHER INFORMATION: BLOCKED with Fmoc
<221> NAME/KEY: MOD_RES
<222> LOCATION: (3)..(3)
<223> OTHER INFORMATION: X is Aib or Pro

<400> SEQUENCE: 9

Lys Asp Xaa Asp Glu Val Asn Gly Ile Asp Pro Lys Gly Tyr
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: BLOCKED with Fmoc
<221> NAME/KEY: MOD_RES
<222> LOCATION: (3)..(3)
<223> OTHER INFORMATION: X is Aib or Pro

<400> SEQUENCE: 10

Lys Asp Xaa Glu Val Asp Gly Ile Asp Pro Lys Gly Tyr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: BLOCKED with Fmoc

<400> SEQUENCE: 11

Lys Asp Ala Ile Pro Met Ser Ile Pro Lys Gly Tyr
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: BLOCKED with Fmoc
<221> NAME/KEY: MOD_RES
<222> LOCATION: (6)..(6)
<223> OTHER INFORMATION: X is norleucine

<400> SEQUENCE: 12

Lys Asp Ala Ile Pro Xaa Ser Ile Pro Lys Gly Tyr
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: BLOCKED with Fmoc
<221> NAME/KEY: MOD_RES
<222> LOCATION: (3)..(3)
```

<223> OTHER INFORMATION: X is Aib or Pro

<400> SEQUENCE: 13

Lys Asp Xaa Gly Asp Glu Val Asp Gly Ile Asp Gly Pro Lys Gly Tyr
1               5                   10                  15

<210> SEQ ID NO 14
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: BLOCKED with Fmoc
<221> NAME/KEY: MOD_RES
<222> LOCATION: (14)..(14)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid
<221> NAME/KEY: MOD_RES
<222> LOCATION: (3)..(3)
<223> OTHER INFORMATION: X is Aib or Pro

<400> SEQUENCE: 14

Lys Asp Xaa Xaa Gly Asp Glu Val Asp Gly Ile Asp Gly Xaa Pro Lys
1               5                   10                  15

Gly Tyr

<210> SEQ ID NO 15
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: MODIFIED WITH benzyloxycarbonyl
<221> NAME/KEY: MOD_RES
<222> LOCATION: (14)..(14)
<223> OTHER INFORMATION: X is epsilon aminoacproic acid
<221> NAME/KEY: MOD_RES
<222> LOCATION: (3)..(3)
<223> OTHER INFORMATION: X is Aib or Pro
<221> NAME/KEY: MOD_RES
<222> LOCATION: (4)..(4)
<223> OTHER INFORMATION: X is epsilon aminoacproic acid

<400> SEQUENCE: 15

Lys Asp Xaa Xaa Gly Asp Glu Val Asp Gly Ile Asp Gly Xaa Pro Lys
1               5                   10                  15

Gly Tyr

<210> SEQ ID NO 16
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: BLOCKED with Fmoc

<400> SEQUENCE: 16

Lys Asp Tyr Asx Ala Asp Gly Ile Asp Pro Lys Gly Tyr
1               5                   10

<210> SEQ ID NO 17

```
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fa
<221> NAME/KEY: MOD_RES
<222> LOCATION: (4)..(4)
<223> OTHER INFORMATION: X is epsilon amino caproic acid

<400> SEQUENCE: 17

Lys Asp Pro Xaa Gly Asp Glu Val Asp Gly Ile Asn Gly Xaa Pro Lys
1               5                   10                  15

Gly Tyr

<210> SEQ ID NO 18
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc
<221> NAME/KEY: MOD_RES
<222> LOCATION: (4)..(4)
<223> OTHER INFORMATION: X is epsilon amino caproic acid
<221> NAME/KEY: MOD_RES
<222> LOCATION: (16)..(16)
<223> OTHER INFORMATION: Blocked with amide

<400> SEQUENCE: 18

Lys Asp Pro Xaa Gly Asp Glu Val Asp Gly Ile Asn Gly Xaa Pro Lys
1               5                   10                  15

<210> SEQ ID NO 19
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Residue blocked with Fmoc
<221> NAME/KEY: MOD_RES
<222> LOCATION: (4)..(4)
<223> OTHER INFORMATION: X is epsilon amino caproic acid
<221> NAME/KEY: MOD_RES
<222> LOCATION: (5)..(5)
<223> OTHER INFORMATION: X is d form tetrahydroisoquinoline-3-carboxylic
      acid

<400> SEQUENCE: 19

Lys Asp Pro Xaa Gly Xaa Asp Glu Val Asp Gly Ile Asn Gly Xaa Pro
1               5                   10                  15

Lys Gly Tyr

<210> SEQ ID NO 20
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc
<221> NAME/KEY: MOD_RES
<222> LOCATION: (4)..(4)
<223> OTHER INFORMATION: X is epsilon amino caproic acid
```

```
<400> SEQUENCE: 20

Lys Asp Pro Xaa Gly Asp Glu Val Asp Gly Ile Asn Gly Pro Lys Gly
1               5                   10                  15
Tyr

<210> SEQ ID NO 21
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc

<400> SEQUENCE: 21

Lys Asp Pro Gly Asp Glu Val Asp Gly Ile Asn Gly Xaa Pro Lys Gly
1               5                   10                  15
Tyr

<210> SEQ ID NO 22
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc
<221> NAME/KEY: MOD_RES
<222> LOCATION: (4)..(4)
<223> OTHER INFORMATION: X is epsilon amino caproic acid
<221> NAME/KEY: MOD_RES
<222> LOCATION: (16)..(16)
<223> OTHER INFORMATION: Blocked with amide

<400> SEQUENCE: 22

Lys Asp Pro Xaa Gly Asp Glu Val Asp Gly Ile Asp Gly Xaa Pro Lys
1               5                   10                  15

<210> SEQ ID NO 23
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc
<221> NAME/KEY: MOD_RES
<222> LOCATION: (4)..(4)
<223> OTHER INFORMATION: X is epsilon amino caproic acid

<400> SEQUENCE: 23

Lys Asp Pro Xaa Gly Glu Glu Val Glu Gly Ile Asn Gly Xaa Pro Lys
1               5                   10                  15
Gly Tyr

<210> SEQ ID NO 24
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc
```

```
<221> NAME/KEY: MOD_RES
<222> LOCATION: (4)..(4)
<223> OTHER INFORMATION: X is epsilon amino caproic acid

<400> SEQUENCE: 24

Lys Asp Pro Xaa Gly Asp Phe Val Asp Gly Ile Asn Gly Xaa Pro Lys
1               5                   10                  15

Gly Tyr

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc
<221> NAME/KEY: MOD_RES
<222> LOCATION: (4)..(4)
<223> OTHER INFORMATION: X is epsilon amino caproic acid

<400> SEQUENCE: 25

Lys Asp Pro Xaa Gly Asp Glu Val Asp Gly Ile Asn Gly Xaa Pro Lys
1               5                   10                  15

Gly Tyr

<210> SEQ ID NO 26
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc
<221> NAME/KEY: MOD_RES
<222> LOCATION: (4)..(4)
<223> OTHER INFORMATION: X is epsilon amino caproic acid

<400> SEQUENCE: 26

Lys Asp Pro Xaa Gly Asp Glu Val Asp Gly Ile Asn Gly Xaa Pro Lys
1               5                   10                  15

Gly Tyr

<210> SEQ ID NO 27
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc
<221> NAME/KEY: MOD_RES
<222> LOCATION: (4)..(4)
<223> OTHER INFORMATION: X is epsilon amino caproic acid

<400> SEQUENCE: 27

Lys Asp Xaa Xaa Gly Asp Glu Val Asn Gly Ile Asn Gly Xaa Pro Lys
1               5                   10                  15

Gly Tyr

<210> SEQ ID NO 28
<211> LENGTH: 18
<212> TYPE: PRT
<213> ORGANISM: Artificial Sequence
```

```
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc
<221> NAME/KEY: MOD_RES
<222> LOCATION: (3)..(3)
<223> OTHER INFORMATION: X is alpha aminoisobutyric acid
<221> NAME/KEY: MOD_RES
<222> LOCATION: (4)..(4)
<223> OTHER INFORMATION: X is epsilon amino caproic acid

<400> SEQUENCE: 28

Lys Asp Xaa Xaa Gly Asp Glu Val Asp Gly Ile Asp Gly Xaa Pro Lys
1               5                   10                  15

Gly Tyr

<210> SEQ ID NO 29
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc
<221> NAME/KEY: MOD_RES
<222> LOCATION: (3)..(3)
<223> OTHER INFORMATION: X is alpha aminoisobutyric acid
<221> NAME/KEY: MOD_RES
<222> LOCATION: (3)..(3)
<223> OTHER INFORMATION: X is alpha aminoisobutyric acid
<221> NAME/KEY: MOD_RES
<222> LOCATION: (4)..(4)
<223> OTHER INFORMATION: X is epsilon amino caproic acid

<400> SEQUENCE: 29

Lys Asp Xaa Xaa Gly Asp Glu Val Asp Gly Ile Asn Gly Xaa Pro Lys
1               5                   10                  15

Gly Tyr

<210> SEQ ID NO 30
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: Blocked with Fmoc
<221> NAME/KEY: MOD_RES
<222> LOCATION: (3)..(3)
<223> OTHER INFORMATION: X is alpha aminoisobutyric acid
<221> NAME/KEY: MOD_RES
<222> LOCATION: (4)..(4)
<223> OTHER INFORMATION: X is epsilon amino caproic acid

<400> SEQUENCE: 30

Lys Asp Xaa Xaa Gly Asp Glu Val Asn Gly Ile Asp Gly Xaa Pro Lys
1               5                   10                  15

Gly Tyr

<210> SEQ ID NO 31
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (4)..(5)
```

<223> OTHER INFORMATION: X is epsilon amino caproic acid
<221> NAME/KEY: MOD_RES
<222> LOCATION: (3)..(3)
<223> OTHER INFORMATION: X is alpha aminoisobutyric acid

<400> SEQUENCE: 31

Lys Asp Xaa Xaa Xaa Gly Asp Glu Val Asp Gly Ile Asp Xaa Xaa Pro
1               5                   10                  15

Lys Gly Tyr

<210> SEQ ID NO 32
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (4)..(4)
<223> OTHER INFORMATION: X is epsilon amino caproic acid
<221> NAME/KEY: MOD_RES
<222> LOCATION: (3)..(3)
<223> OTHER INFORMATION: X is alpha aminoisobutyric acid

<400> SEQUENCE: 32

Lys Asp Xaa Xaa Gly Asn Glu Val Asp Gly Ile Asp Gly Xaa Pro Lys
1               5                   10                  15

Gly Tyr

<210> SEQ ID NO 33
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (4)..(4)
<223> OTHER INFORMATION: X is epsilon amino caproic acid
<221> NAME/KEY: MOD_RES
<222> LOCATION: (3)..(3)
<223> OTHER INFORMATION: X is alpha aminoisobutyric acid

<400> SEQUENCE: 33

Lys Asp Xaa Xaa Gly Asp Glu Val Asp Gly Ile Asn Gly Xaa Pro Lys
1               5                   10                  15

Gly Tyr

<210> SEQ ID NO 34
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (4)..(4)
<223> OTHER INFORMATION: X is epsilon amino caproic acid
<221> NAME/KEY: MOD_RES
<222> LOCATION: (3)..(3)
<223> OTHER INFORMATION: X is alpha aminoisobutyric acid

<400> SEQUENCE: 34

Lys Asp Xaa Xaa Gly Asn Glu Val Asp Gly Ile Asn Gly Xaa Pro Lys
1               5                   10                  15

Gly Tyr

<210> SEQ ID NO 35
<211> LENGTH: 18
<212> TYPE: PRT

```
<213> ORGANISM: Artificial Sequence
<220> FEATURE:
<223> OTHER INFORMATION: Synthetic peptide substrate
<221> NAME/KEY: MOD_RES
<222> LOCATION: (4)..(4)
<223> OTHER INFORMATION: X is epsilon amino caproic acid
<221> NAME/KEY: MOD_RES
<222> LOCATION: (3)..(3)
<223> OTHER INFORMATION: X is alpha aminoisobutyric acid

<400> SEQUENCE: 35

Lys Asp Xaa Xaa Gly Asp Glu Val Asn Gly Ile Asn Gly Xaa Pro Lys
1               5                   10                  15

Gly Tyr

<210> SEQ ID NO 36
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (4)..(4)
<223> OTHER INFORMATION: X is epsilon amino caproic acid
<221> NAME/KEY: MOD_RES
<222> LOCATION: (3)..(3)
<223> OTHER INFORMATION: X is alpha aminoisobutyric acid

<400> SEQUENCE: 36

Lys Asp Xaa Xaa Gly Asn Glu Val Asn Gly Ile Asn Gly Xaa Pro Lys
1               5                   10                  15

Gly Tyr

<210> SEQ ID NO 37
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: Aib
<221> NAME/KEY: MOD_RES
<222> LOCATION: (6)..(6)
<223> OTHER INFORMATION: X is tetrahydroisoquinoline-3-carboxylic acid
<221> NAME/KEY: MOD_RES
<222> LOCATION: (15)..(15)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid

<400> SEQUENCE: 37

Lys Asp Xaa Xaa Gly Xaa Asp Glu Val Asp Gly Ile Asp Gly Xaa Pro
1               5                   10                  15

Lys Gly Lys

<210> SEQ ID NO 38
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (6)..(6)
<223> OTHER INFORMATION: X is D form tetrahydroisoquinoline-3-carboxylic
      acid
```

```
<221> NAME/KEY: MOD_RES
<222> LOCATION: (15)..(15)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid

<400> SEQUENCE: 38

Lys Asp Xaa Xaa Gly Xaa Asp Glu Val Asp Gly Ile Asp Gly Xaa Pro
1               5                   10                  15

Lys Gly Tyr

<210> SEQ ID NO 39
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (15)..(15)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid

<400> SEQUENCE: 39

Lys Asp Xaa Xaa Gly Trp Asp Glu Val Asp Gly Ile Asp Gly Xaa Pro
1               5                   10                  15

Lys Gly Tyr

<210> SEQ ID NO 40
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (6)..(6)
<223> OTHER INFORMATION: W is D form
<221> NAME/KEY: MOD_RES
<222> LOCATION: (15)..(15)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid

<400> SEQUENCE: 40

Lys Asp Xaa Xaa Gly Trp Asp Glu Val Asp Gly Ile Asp Gly Xaa Pro
1               5                   10                  15

Lys Gly Tyr

<210> SEQ ID NO 41
<211> LENGTH: 20
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (6)..(7)
<223> OTHER INFORMATION: X is D form tetrahydroisoquinoline-3-carboxylic
      acid
```

```
<221> NAME/KEY: MOD_RES
<222> LOCATION: (16)..(16)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid

<400> SEQUENCE: 41

Lys Asp Xaa Xaa Gly Xaa Xaa Asp Glu Val Asp Gly Ile Asp Gly Xaa
1               5                   10                  15

Pro Lys Gly Tyr
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (6)..(7)
<223> OTHER INFORMATION: W is D form
<221> NAME/KEY: MOD_RES
<222> LOCATION: (16)..(16)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid

<400> SEQUENCE: 42

Lys Asp Xaa Xaa Gly Trp Trp Asp Glu Val Asp Gly Ile Asp Gly Xaa
1               5                   10                  15

Pro Lys Gly Tyr
            20

<210> SEQ ID NO 43
<211> LENGTH: 14
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 43

Lys Asp Xaa Tyr Val Ala Asp Gly Ile Asp Pro Lys Gly Tyr
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 44

Lys Asp Xaa Tyr Val Ala Asp Gly Ile Asn Pro Lys Gly Tyr
1               5                   10

<210> SEQ ID NO 45
<211> LENGTH: 14
<212> TYPE: PRT
```

```
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 45

Lys Asp Xaa Tyr Val Ala Asn Gly Ile Asn Pro Lys Gly Tyr
1               5                   10

<210> SEQ ID NO 46
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 46

Lys Asp Xaa Gly Tyr Val Ala Asp Gly Ile Asp Gly Pro Lys Gly Tyr
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 47

Lys Asp Xaa Gly Tyr Val Ala Asp Gly Ile Asn Gly Pro Lys Gly Tyr
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 48

Lys Asp Xaa Gly Tyr Val Ala Asn Gly Ile Asn Gly Pro Lys Gly Tyr
1               5                   10                  15

<210> SEQ ID NO 49
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid

<400> SEQUENCE: 49
```

-continued

```
Lys Asp Xaa Xaa Gly Tyr Val Ala Asp Gly Ile Asp Gly Xaa Pro Lys
1               5                   10                  15

Gly Tyr

<210> SEQ ID NO 50
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid

<400> SEQUENCE: 50

Lys Asp Xaa Xaa Gly Tyr Val Ala Asn Gly Ile Asp Gly Xaa Pro Lys
1               5                   10                  15

Gly Tyr

<210> SEQ ID NO 51
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid

<400> SEQUENCE: 51

Lys Asp Xaa Xaa Gly Tyr Val Ala Asn Gly Ile Asn Gly Xaa Pro Lys
1               5                   10                  15

Gly Tyr

<210> SEQ ID NO 52
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid

<400> SEQUENCE: 52

Lys Asp Xaa Xaa Gly Tyr Val Ala Asp Gly Ile Asn Gly Xaa Pro Lys
1               5                   10                  15

Gly Tyr

<210> SEQ ID NO 53
```

-continued

```
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (6)..(6)
<223> OTHER INFORMATION: Y is D form
<221> NAME/KEY: MOD_RES
<222> LOCATION: (14)..(14)
<223> OTHER INFORMATION: X is epsilon aminocaproic acid
<221> NAME/KEY: MOD_RES
<222> LOCATION: (4)..(4)
<223> OTHER INFORMATION: X is epsilon aminocaproic acid

<400> SEQUENCE: 53

Lys Asp Xaa Xaa Gly Tyr Val Ala Asp Gly Ile Asn Gly Xaa Pro Lys
1               5                   10                  15

Gly Tyr

<210> SEQ ID NO 54
<211> LENGTH: 18
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (14)..(14)
<223> OTHER INFORMATION: Xaa is episilon-aminocaproic acid

<400> SEQUENCE: 54

Lys Asp Xaa Xaa Gly Tyr Val Ala Asp Gly Ile Asn Gly Xaa Pro Lys
1               5                   10                  15

Gly Tyr

<210> SEQ ID NO 55
<211> LENGTH: 14
<212> TYPE: PRT
<213> ORGANISM: Artificial Sequence
<220> FEATURE:
<223> OTHER INFORMATION: protease indicator
<221> NAME/KEY: misc_feature
<222> LOCATION: (3)..(3)
<223> OTHER INFORMATION: Xaa is alpha-aminoisobutyric acid

<400> SEQUENCE: 55

Lys Asp Xaa Tyr Val His Asp Ala Pro Val Pro Lys Gly Tyr
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (3)..(3)
<223> OTHER INFORMATION: Xaa is alpha-aminoisobutyric acid

<400> SEQUENCE: 56

Lys Asp Xaa Tyr Val His Asp Ala Pro Val Pro Lys Gly Tyr
1               5                   10

<210> SEQ ID NO 57
<211> LENGTH: 14
<212> TYPE: PRT
```

```
<213> ORGANISM: Artificial Sequence
<220> FEATURE:
<223> OTHER INFORMATION: Protease indicator
<221> NAME/KEY: misc_feature
<222> LOCATION: (3)..(3)
<223> OTHER INFORMATION: Xaa is alpha-aminoisobutyric acid

<400> SEQUENCE: 57

Lys Asp Xaa Tyr Val His Asp Ala Pro Val Pro Lys Gly Tyr
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (3)..(3)
<223> OTHER INFORMATION: Xaa is alpha-aminoisobutyric acid

<400> SEQUENCE: 58

Lys Asp Xaa Gly Tyr Val His Asp Ala Pro Val Gly Pro Lys Gly Tyr
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (3)..(3)
<223> OTHER INFORMATION: Xaa is alpha-aminoisobutyric acid

<400> SEQUENCE: 59

Lys Asp Xaa Gly Tyr Val His Asp Ala Pro Val Gly Pro Lys Gly Tyr
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (3)..(3)
<223> OTHER INFORMATION: Xaa is alpha-aminoisobutyric acid

<400> SEQUENCE: 60

Lys Asp Xaa Gly Tyr Val His Asp Ala Pro Val Gly Pro Lys Gly Tyr
1               5                   10                  15

<210> SEQ ID NO 61
<211> LENGTH: 17
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (3)..(3)
<223> OTHER INFORMATION: Xaa is alpha-aminoisobutyric acid
<221> NAME/KEY: misc_feature
<222> LOCATION: (4)..(4)
<223> OTHER INFORMATION: Xaa is episilon-aminocaproic acid

<400> SEQUENCE: 61

Lys Asp Xaa Xaa Gly Tyr Val His Asp Ala Pro Val Gly Pro Lys Gly
1               5                   10                  15
```

Tyr

<210> SEQ ID NO 62
<211> LENGTH: 17
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (3)..(3)
<223> OTHER INFORMATION: Xaa is alpha-aminoisobutyric acid
<221> NAME/KEY: misc_feature
<222> LOCATION: (4)..(4)
<223> OTHER INFORMATION: Xaa is episilon-aminocaproic acid

<400> SEQUENCE: 62

Lys Asp Xaa Xaa Gly Tyr Val His Asp Ala Pro Val Gly Pro Lys Gly
1               5                   10                  15

Tyr

<210> SEQ ID NO 63
<211> LENGTH: 17
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (3)..(3)
<223> OTHER INFORMATION: Xaa is alpha-aminoisobutyric acid
<221> NAME/KEY: misc_feature
<222> LOCATION: (4)..(4)
<223> OTHER INFORMATION: Xaa is episilon-aminocaproic acid

<400> SEQUENCE: 63

Lys Asp Xaa Xaa Gly Tyr Val His Asp Ala Pro Val Gly Pro Lys Gly
1               5                   10                  15

Tyr

<210> SEQ ID NO 64
<211> LENGTH: 17
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (3)..(3)
<223> OTHER INFORMATION: Xaa is alpha-aminoisobutyric acid
<221> NAME/KEY: misc_feature
<222> LOCATION: (4)..(4)
<223> OTHER INFORMATION: Xaa is episilon-aminocaproic acid

<400> SEQUENCE: 64

Lys Asp Xaa Xaa Gly Tyr Val His Asp Ala Pro Val Gly Pro Lys Gly
1               5                   10                  15

Tyr

<210> SEQ ID NO 65
<211> LENGTH: 17
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (3)..(3)
<223> OTHER INFORMATION: Xaa is alpha-aminoisobutyric acid
<221> NAME/KEY: misc_feature
<222> LOCATION: (4)..(4)
<223> OTHER INFORMATION: Xaa is episilon-aminocaproic acid

```
<400> SEQUENCE: 65

Lys Asp Xaa Xaa Gly Tyr Val His Asp Ala Pro Val Gly Pro Lys Gly
1               5                   10                  15

Tyr

<210> SEQ ID NO 66
<211> LENGTH: 18
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (3)..(3)
<223> OTHER INFORMATION: Xaa is alpha-aminoisobutyric acid
<221> NAME/KEY: misc_feature
<222> LOCATION: (4)..(4)
<223> OTHER INFORMATION: Xaa is episilon-aminocaproic acid

<400> SEQUENCE: 66

Lys Asp Xaa Xaa Gly Asp Tyr Val His Asp Ala Pro Val Gly Pro Lys
1               5                   10                  15

Gly Tyr

<210> SEQ ID NO 67
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 67

Lys Asp Pro Xaa Gly Leu Val Glu Ile Asp Asn Gly Xaa Pro Lys Gly
1               5                   10                  15

Tyr

<210> SEQ ID NO 68
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 68

Lys Asp Pro Xaa Gly Leu Val Glu Ile Glu Asn Gly Xaa Pro Lys Gly
1               5                   10                  15

Tyr

<210> SEQ ID NO 69
<211> LENGTH: 14
```

```
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 69

Lys Asp Xaa Leu Val Glu Ile Asp Asn Gly Pro Lys Gly Tyr
1               5                   10

<210> SEQ ID NO 70
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 70

Lys Asp Xaa Gly Leu Val Glu Ile Asp Asn Gly Gly Pro Lys Gly Tyr
1               5                   10                  15

<210> SEQ ID NO 71
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 71

Lys Asp Xaa Xaa Gly Leu Val Glu Ile Asp Asn Gly Gly Xaa Pro Lys
1               5                   10                  15

Gly Tyr

<210> SEQ ID NO 72
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 72

Lys Asp Xaa Xaa Gly Leu Val Glu Ile Asn Asn Gly Gly Xaa Pro Lys
1               5                   10                  15

Gly Tyr

<210> SEQ ID NO 73
```

<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 73

Lys Asp Pro Xaa Gly Ile Glu Thr Glu Ser Gly Val Gly Xaa Pro Lys
1               5                   10                  15

Gly Tyr

<210> SEQ ID NO 74
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (12)..(12)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 74

Lys Asp Pro Xaa Gly Ile Glu Thr Asp Ser Gly Xaa Pro Lys Gly Tyr
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (12)..(12)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 75

Lys Asp Pro Xaa Gly Ile Glu Thr Glu Ser Gly Xaa Pro Lys Gly Tyr
1               5                   10                  15

<210> SEQ ID NO 76
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 76

Lys Asp Xaa Gly Ile Glu Thr Asp Ser Gly Val Asp Pro Lys Gly
1               5                   10                  15

Tyr

<210> SEQ ID NO 77
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 77

Lys Asp Xaa Gly Ile Glu Thr Asn Ser Gly Val Asp Asp Pro Lys Gly
1               5                   10                  15

Tyr

<210> SEQ ID NO 78
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 78

Lys Asp Xaa Gly Gly Ile Glu Thr Asp Ser Gly Val Asp Asp Gly Pro
1               5                   10                  15

Lys Gly Tyr

<210> SEQ ID NO 79
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 79

Lys Asp Xaa Gly Gly Ile Glu Thr Asn Ser Gly Val Gly Pro Lys Gly
1               5                   10                  15

Tyr

<210> SEQ ID NO 80
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 80

Lys Asp Xaa Xaa Gly Ile Glu Thr Asp Ser Gly Val Xaa Pro Lys Gly

```
1               5                  10                 15
Tyr

<210> SEQ ID NO 81
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 81

Lys Asp Xaa Xaa Gly Ile Glu Thr Asn Ser Gly Val Xaa Pro Lys Gly
1               5                  10                 15

Tyr

<210> SEQ ID NO 82
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 82

Lys Asp Xaa Xaa Gly Gly Ile Glu Thr Asp Ser Gly Val Gly Xaa Pro
1               5                  10                 15

Lys Gly Tyr

<210> SEQ ID NO 83
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 83

Lys Asp Xaa Xaa Gly Gly Ile Glu Thr Asn Ser Gly Val Gly Xaa Pro
1               5                  10                 15

Lys Gly Tyr

<210> SEQ ID NO 84
<211> LENGTH: 19
```

```
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 84

Lys Asp Xaa Gly Ser Glu Ser Met Asp Ser Gly Ile Ser Leu Asp Pro
1               5                   10                  15

Lys Gly Tyr

<210> SEQ ID NO 85
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 85

Lys Asp Xaa Gly Gly Ser Glu Ser Met Asp Ser Gly Gly Pro Lys Gly
1               5                   10                  15

Tyr

<210> SEQ ID NO 86
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 86

Lys Asp Xaa Xaa Gly Gly Ser Glu Ser Met Asp Ser Gly Gly Xaa Pro
1               5                   10                  15

Lys Gly Tyr

<210> SEQ ID NO 87
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 87

Lys Asp Xaa Xaa Gly Asp Val Val Cys Cys Ser Met Ser Gly Xaa Pro
1               5                   10                  15
```

Lys Gly Tyr

<210> SEQ ID NO 88
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 88

Lys Asp Xaa Xaa Gly Asp Val Val Cys Asp Ser Met Ser Gly Xaa Pro
1               5                   10                  15

Lys Gly Tyr

<210> SEQ ID NO 89
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(12)
<223> OTHER INFORMATION: M is D form
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 89

Lys Asp Xaa Xaa Gly Asp Val Val Cys Cys Ser Met Ser Gly Xaa Pro
1               5                   10                  15

Lys Gly Tyr

<210> SEQ ID NO 90
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(12)
<223> OTHER INFORMATION: M is D form
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 90

Lys Asp Xaa Xaa Gly Asp Val Val Cys Asp Ser Met Ser Gly Xaa Pro
1               5                   10                  15

Lys Gly Tyr

<210> SEQ ID NO 91
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(12)
<223> OTHER INFORMATION: M is D form
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 91

Lys Asp Xaa Xaa Gly Asp Val Val Cys Cys Pro Met Ser Gly Xaa Pro
1               5                   10                  15

Lys Gly Tyr

<210> SEQ ID NO 92
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 92

Lys Asp Xaa Xaa Gly Glu Asp Val Val Cys Cys Ser Gly Xaa Pro Lys
1               5                   10                  15

Gly Tyr

<210> SEQ ID NO 93
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 93

Lys Asp Xaa Xaa Gly Glu Asp Val Val Cys Asp Ser Gly Xaa Pro Lys
1               5                   10                  15

Gly Tyr

<210> SEQ ID NO 94
<211> LENGTH: 18

```
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (8)..(8)
<223> OTHER INFORMATION: V is D form
<221> NAME/KEY: MOD_RES
<222> LOCATION: (4)..(4)
<223> OTHER INFORMATION: X is epsilon aminocaproic acid

<400> SEQUENCE: 94

Lys Asp Xaa Xaa Gly Glu Asp Val Val Cys Cys Pro Gly Xaa Pro Lys
1               5                   10                  15

Gly Tyr

<210> SEQ ID NO 95
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (8)..(8)
<223> OTHER INFORMATION: V is D form
<221> NAME/KEY: MOD_RES
<222> LOCATION: (4)..(4)
<223> OTHER INFORMATION: X is epsilon aminocaproic acid

<400> SEQUENCE: 95

Lys Asp Xaa Xaa Gly Glu Asp Val Val Cys Asp Pro Gly Xaa Pro Lys
1               5                   10                  15

Gly Tyr

<210> SEQ ID NO 96
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (12)..(12)
<223> OTHER INFORMATION: M is D form
<221> NAME/KEY: MOD_RES
<222> LOCATION: (7)..(7)
<223> OTHER INFORMATION: V is D form
<221> NAME/KEY: MOD_RES
<222> LOCATION: (4)..(4)
<223> OTHER INFORMATION: X is epsilon aminocaproic acid

<400> SEQUENCE: 96

Lys Asp Xaa Xaa Gly Asp Val Val Cys Cys Ser Met Ser Gly Xaa Pro
1               5                   10                  15
```

-continued

Lys Gly Tyr

<210> SEQ ID NO 97
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(12)
<223> OTHER INFORMATION: M is D form
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (8)..(8)
<223> OTHER INFORMATION: V is D form
<221> NAME/KEY: MOD_RES
<222> LOCATION: (4)..(4)
<223> OTHER INFORMATION: X is epsilon aminocaproic acid

<400> SEQUENCE: 97

Lys Asp Xaa Xaa Gly Asp Val Val Cys Asp Ser Met Ser Gly Xaa Pro
1               5                   10                  15

Lys Gly Tyr

<210> SEQ ID NO 98
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(12)
<223> OTHER INFORMATION: M is D form
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (7)..(7)
<223> OTHER INFORMATION: V is D form
<221> NAME/KEY: MOD_RES
<222> LOCATION: (4)..(4)
<223> OTHER INFORMATION: X is epsilon aminocaproic acid

<400> SEQUENCE: 98

Lys Asp Xaa Xaa Gly Asp Val Val Cys Cys Pro Met Ser Gly Xaa Pro
1               5                   10                  15

Lys Gly Tyr

<210> SEQ ID NO 99
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

```
<400> SEQUENCE: 99

Lys Asp Xaa Xaa Gly Asp Val Val Cys Cys Ser Met Gly Xaa Pro Lys
1               5                   10                  15

Gly Tyr

<210> SEQ ID NO 100
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 100

Lys Asp Xaa Xaa Gly Asp Val Val Cys Asp Ser Met Gly Xaa Pro Lys
1               5                   10                  15

Gly Tyr

<210> SEQ ID NO 101
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(12)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 101

Lys Asp Xaa Xaa Gly Val Cys Cys Ser Met Gly Xaa Pro Lys Gly Tyr
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(12)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 102

Lys Asp Xaa Xaa Gly Val Cys Asp Ser Met Gly Xaa Pro Lys Gly Tyr
1               5                   10                  15

<210> SEQ ID NO 103
<211> LENGTH: 19
<212> TYPE: PRT
```

```
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (4)..(4)
<223> OTHER INFORMATION: X is epsilon aminocaproic acid

<400> SEQUENCE: 103

Lys Asp Xaa Xaa Gly Asp Glu Met Glu Glu Cys Ser Gln His Leu Pro
1               5                   10                  15

Lys Gly Tyr

<210> SEQ ID NO 104
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (4)..(4)
<223> OTHER INFORMATION: X is epsilon aminocaproic acid

<400> SEQUENCE: 104

Lys Asp Xaa Xaa Gly Asp Glu Met Glu Glu Cys Pro Gln His Leu Pro
1               5                   10                  15

Lys Gly Tyr

<210> SEQ ID NO 105
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (4)..(4)
<223> OTHER INFORMATION: X is epsilon aminocaproic acid

<400> SEQUENCE: 105

Lys Asp Xaa Xaa Gly Asp Glu Met Glu Glu Asp Ser Gln His Leu Pro
1               5                   10                  15

Lys Gly Tyr

<210> SEQ ID NO 106
<211> LENGTH: 18
<212> TYPE: PRT
<213> ORGANISM: artificial sequence
<220> FEATURE:
<221> NAME/KEY: MOD_RES
<222> LOCATION: (3)..(3)
<223> OTHER INFORMATION: X is Aib
<221> NAME/KEY: MOD_RES
<222> LOCATION: (4)..(4)
<223> OTHER INFORMATION: X is epsilon aminocaproic acid

<400> SEQUENCE: 106

Lys Asp Xaa Xaa Gly Glu Met Glu Glu Cys Ser Gln His Leu Pro Lys
1               5                   10                  15

Gly Tyr
```

```
<210> SEQ ID NO 107
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (4)..(4)
<223> OTHER INFORMATION: X is epsilon aminocaproic acid

<400> SEQUENCE: 107

Lys Asp Xaa Xaa Gly Glu Met Glu Glu Cys Pro Gln His Leu Pro Lys
1               5                   10                  15

Gly Tyr

<210> SEQ ID NO 108
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (4)..(4)
<223> OTHER INFORMATION: X is epsilon aminocaproic acid

<400> SEQUENCE: 108

Lys Asp Xaa Xaa Gly Glu Met Glu Glu Asp Ser Gln His Leu Pro Lys
1               5                   10                  15

Gly Tyr

<210> SEQ ID NO 109
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (4)..(4)
<223> OTHER INFORMATION: X is epsilon aminocaproic acid

<400> SEQUENCE: 109

Lys Asp Xaa Xaa Gly Glu Met Glu Glu Cys Ser Gln His Leu Gly Pro
1               5                   10                  15

Lys Gly Tyr

<210> SEQ ID NO 110
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (4)..(4)
<223> OTHER INFORMATION: X is epsilon aminocaproic acid

<400> SEQUENCE: 110
```

```
-continued

Lys Asp Xaa Xaa Gly Glu Met Glu Glu Cys Pro Gln His Leu Gly Pro
1               5                   10                  15

Lys Gly Tyr

<210> SEQ ID NO 111
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (4)..(4)
<223> OTHER INFORMATION: X is epsilon aminocaproic acid

<400> SEQUENCE: 111

Lys Asp Xaa Xaa Gly Glu Met Glu Glu Asp Ser Gln His Leu Gly Pro
1               5                   10                  15

Lys Gly Tyr

<210> SEQ ID NO 112
<211> LENGTH: 20
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (16)..(16)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 112

Lys Asp Xaa Xaa Gly Glu Met Glu Glu Cys Ser Gln His Leu Gly Xaa
1               5                   10                  15

Pro Lys Gly Tyr
        20

<210> SEQ ID NO 113
<211> LENGTH: 20
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (16)..(16)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 113

Lys Asp Xaa Xaa Gly Glu Met Glu Glu Cys Pro Gln His Leu Gly Xaa
1               5                   10                  15

Pro Lys Gly Tyr
        20

<210> SEQ ID NO 114
<211> LENGTH: 20
```

```
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (16)..(16)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 114

Lys Asp Xaa Xaa Gly Glu Met Glu Glu Asp Ser Gln His Leu Gly Xaa
1               5                   10                  15

Pro Lys Gly Tyr
            20

<210> SEQ ID NO 115
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 115

Lys Asp Xaa Xaa Gly Val Met Thr Gly Arg Thr Gly Xaa Pro Lys Gly
1               5                   10                  15

Tyr

<210> SEQ ID NO 116
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (7)..(7)
<223> OTHER INFORMATION: M is D form
<221> NAME/KEY: MOD_RES
<222> LOCATION: (4)..(4)
<223> OTHER INFORMATION: X is epsilon aminocaproic acid

<400> SEQUENCE: 116

Lys Asp Xaa Xaa Gly Val Met Thr Gly Arg Thr Gly Xaa Pro Lys Gly
1               5                   10                  15

Tyr

<210> SEQ ID NO 117
<211> LENGTH: 17
<212> TYPE: PRT
<213> ORGANISM: Artificial Sequence
<220> FEATURE:
```

```
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 117

Lys Asp Xaa Xaa Gly Val Met Thr Gly Arg Thr Gly Xaa Pro Lys Gly
1               5                   10                  15

Tyr

<210> SEQ ID NO 118
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 118

Lys Asp Xaa Xaa Gly Val Met Thr Gly Arg Thr Gly Xaa Pro Lys Gly
1               5                   10                  15

Tyr

<210> SEQ ID NO 119
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(12)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 119

Lys Asp Xaa Xaa Gly Val Met Thr Gly Arg Gly Xaa Pro Lys Gly Tyr
1               5                   10                  15

<210> SEQ ID NO 120
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
```

<223> OTHER INFORMATION: X is epsilon aminocaproic acid

<400> SEQUENCE: 120

Lys Asp Xaa Xaa Gly Val Met Thr Gly Arg Gly Gly Xaa Pro Lys Gly
1               5                   10                  15

Tyr

<210> SEQ ID NO 121
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (7)..(7)
<223> OTHER INFORMATION: M is D form
<221> NAME/KEY: MOD_RES
<222> LOCATION: (4)..(4)
<223> OTHER INFORMATION: X is epsilon aminocaproic acid

<400> SEQUENCE: 121

Lys Asp Xaa Xaa Gly Val Met Thr Gly Arg Gly Gly Xaa Pro Lys Gly
1               5                   10                  15

Tyr

<210> SEQ ID NO 122
<211> LENGTH: 8
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (4)..(4)
<223> OTHER INFORMATION: X is epsilon aminocaproic acid
<221> NAME/KEY: MOD_RES
<222> LOCATION: (1)..(1)
<223> OTHER INFORMATION: K is blocked with Fmoc

<400> SEQUENCE: 122

Lys Asp Pro Xaa Thr Gly Arg Thr
1               5

<210> SEQ ID NO 123
<211> LENGTH: 11
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: D is blocked with Fmoc

<400> SEQUENCE: 123

Asp Pro Thr Gly Arg Thr Gly Pro Lys Gly Tyr
1               5                   10

<210> SEQ ID NO 124
<211> LENGTH: 15
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (11)..(11)
<223> OTHER INFORMATION: X is episilon-aminocaproic acid

<400> SEQUENCE: 124

Lys Asp Pro Val Met Thr Gly Arg Thr Gly Xaa Pro Lys Gly Tyr
1               5                   10                  15

<210> SEQ ID NO 125
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (9)..(9)
<223> OTHER INFORMATION: X is episilon-aminocaproic acid

<400> SEQUENCE: 125

Lys Asp Pro Thr Gly Arg Thr Gly Xaa Pro Lys Gly Tyr
1               5                   10

<210> SEQ ID NO 126
<211> LENGTH: 15
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (4)..(4)
<223> OTHER INFORMATION: X is epsilon aminocaproic acid
<221> NAME/KEY: MOD_RES
<222> LOCATION: (11)..(11)
<223> OTHER INFORMATION: X is episilon-aminocaproic acid

<400> SEQUENCE: 126

Lys Asp Pro Xaa Gly Thr Gly Arg Thr Gly Xaa Pro Lys Gly Tyr
1               5                   10                  15

<210> SEQ ID NO 127
<211> LENGTH: 14
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (4)..(4)
<223> OTHER INFORMATION: X is epsilon aminocaproic acid

<400> SEQUENCE: 127

Lys Asp Pro Xaa Gly Thr Gly Arg Thr Gly Pro Lys Gly Tyr
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES

```
<222> LOCATION: (1)..(1)
<223> OTHER INFORMATION: K is blocked with Fmoc

<400> SEQUENCE: 128

Lys Asp Pro Gly Thr Gly Arg Thr Gly Pro Lys Gly Tyr
1               5                   10

<210> SEQ ID NO 129
<211> LENGTH: 14
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (4)..(4)
<223> OTHER INFORMATION: X is epsilon aminocaproic acid
<221> NAME/KEY: MOD_RES
<222> LOCATION: (10)..(10)
<223> OTHER INFORMATION: X is episilon-aminocaproic acid

<400> SEQUENCE: 129

Lys Asp Pro Xaa Thr Gly Arg Thr Gly Xaa Pro Lys Gly Tyr
1               5                   10

<210> SEQ ID NO 130
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (4)..(4)
<223> OTHER INFORMATION: X is 4-aminobutyric acid

<400> SEQUENCE: 130

Lys Asp Pro Xaa Thr Gly Arg Thr Gly Pro Lys Gly Tyr
1               5                   10

<210> SEQ ID NO 131
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (4)..(4)
<223> OTHER INFORMATION: X is 8-aminobutyric acid

<400> SEQUENCE: 131

Lys Asp Pro Xaa Thr Gly Arg Thr Gly Pro Lys Gly Tyr
1               5                   10

<210> SEQ ID NO 132
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 132

Lys Asp Xaa Xaa Gly Val Met Thr Gly Arg Val Gly Xaa Pro Lys Gly
```

-continued

```
1               5                  10                 15
Tyr

<210> SEQ ID NO 133
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (7)..(7)
<223> OTHER INFORMATION: M is D form
<221> NAME/KEY: MOD_RES
<222> LOCATION: (4)..(4)
<223> OTHER INFORMATION: X is epsilon aminocaproic acid

<400> SEQUENCE: 133

Lys Asp Xaa Xaa Gly Val Met Thr Gly Arg Val Gly Xaa Pro Lys Gly
1               5                  10                 15
Tyr

<210> SEQ ID NO 134
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 134

Lys Asp Xaa Xaa Gly Val Met Thr Gly Arg Ala Gly Xaa Pro Lys Gly
1               5                  10                 15
Tyr

<210> SEQ ID NO 135
<211> LENGTH: 17
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (7)..(7)
<223> OTHER INFORMATION: M is D form
<221> NAME/KEY: MOD_RES
<222> LOCATION: (4)..(4)
<223> OTHER INFORMATION: X is epsilon aminocaproic acid

<400> SEQUENCE: 135

Lys Asp Xaa Xaa Gly Val Met Thr Gly Arg Ala Gly Xaa Pro Lys Gly
1               5                  10                 15
```

Tyr

<210> SEQ ID NO 136
<211> LENGTH: 26
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (4)..(4)
<223> OTHER INFORMATION: X is epsilon aminocaproic acid
<221> NAME/KEY: MOD_RES
<222> LOCATION: (22)..(22)
<223> OTHER INFORMATION: X is epsilon aminocaproic acid
<221> NAME/KEY: MOD_RES
<222> LOCATION: (1)..(1)
<223> OTHER INFORMATION: K is blocked with Fmoc

<400> SEQUENCE: 136

Lys Asp Pro Xaa Gly Ser Glu Val Lys Leu Asp Ala Glu Phe Gly Xaa
1               5                   10                  15

Pro Lys Gly Tyr Gly Xaa Pro Lys Gly Tyr
            20                  25

<210> SEQ ID NO 137
<211> LENGTH: 20
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (16)..(16)
<223> OTHER INFORMATION: X is episilon-aminocaproic acid
<221> NAME/KEY: MOD_RES
<222> LOCATION: (7)..(7)
<223> OTHER INFORMATION: E is D form
<221> NAME/KEY: MOD_RES
<222> LOCATION: (10)..(10)
<223> OTHER INFORMATION: L is D form
<221> NAME/KEY: MOD_RES
<222> LOCATION: (14)..(14)
<223> OTHER INFORMATION: F is D form
<221> NAME/KEY: MOD_RES
<222> LOCATION: (4)..(4)
<223> OTHER INFORMATION: X is epsilon aminocaproic acid

<400> SEQUENCE: 137

Lys Asp Pro Xaa Gly Ser Glu Val Lys Leu Asp Ala Glu Phe Gly Xaa
1               5                   10                  15

Pro Lys Gly Tyr
            20

<210> SEQ ID NO 138
<211> LENGTH: 20
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (16)..(16)
<223> OTHER INFORMATION: X is episilon-aminocaproic acid
<221> NAME/KEY: MOD_RES
<222> LOCATION: (7)..(7)
<223> OTHER INFORMATION: E is D form
<221> NAME/KEY: MOD_RES

```
<222> LOCATION: (10)..(10)
<223> OTHER INFORMATION: L is D form
<221> NAME/KEY: MOD_RES
<222> LOCATION: (14)..(14)
<223> OTHER INFORMATION: F is D form
<221> NAME/KEY: MOD_RES
<222> LOCATION: (4)..(4)
<223> OTHER INFORMATION: X is epsilon aminocaproic acid

<400> SEQUENCE: 138

Lys Asp Pro Xaa Gly Ser Glu Val Lys Leu Asp Ala Glu Phe Gly Xaa
1               5                   10                  15

Pro Lys Gly Tyr
            20

<210> SEQ ID NO 139
<211> LENGTH: 21
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (16)..(16)
<223> OTHER INFORMATION: X is episilon-aminocaproic acid
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (4)..(4)
<223> OTHER INFORMATION: X is epsilon aminocaproic acid

<400> SEQUENCE: 139

Lys Asp Xaa Xaa Gly Ser Glu Val Asn Leu Asp Ala Glu Phe Gly Xaa
1               5                   10                  15

Pro Lys Asp Asp Tyr
            20

<210> SEQ ID NO 140
<211> LENGTH: 21
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (16)..(16)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 140

Lys Asp Xaa Xaa Gly Ser Glu Val Lys Leu Asp Ala Glu Phe Gly Xaa
1               5                   10                  15

Pro Lys Asp Asp Tyr
            20

<210> SEQ ID NO 141
<211> LENGTH: 21
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
```

<223> OTHER INFORMATION: X is Aib
<221> NAME/KEY: MOD_RES
<222> LOCATION: (16)..(16)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 141

Lys Asp Xaa Xaa Gly Ser Glu Val Lys Met Asp Ala Glu Phe Gly Xaa
1               5                   10                  15

Pro Lys Asp Asp Tyr
            20

<210> SEQ ID NO 142
<211> LENGTH: 21
<212> TYPE: PRT
<213> ORGANISM: Artificial Sequence
<220> FEATURE:
<223> OTHER INFORMATION: Synthetic peptide substrate
<221> NAME/KEY: MOD_RS
<222> LOCATION: (3)..(3)
<223> OTHER INFORMATION: X is Aib
<221> NAME/KEY: MOD_RS
<222> LOCATION: (16)..(16)
<223> OTHER INFORMATION: X is episilon-aminocaproic acid
<221> NAME/KEY: MOD_RS
<222> LOCATION: (4)..(4)
<223> OTHER INFORMATION: X is epsilon aminocaproic acid

<400> SEQUENCE: 142

Lys Asp Xaa Xaa Gly Ser Glu Val Lys Met Asp Glu Phe Gly Xaa
1               5                   10                  15

Pro Lys Asp Asp Tyr
            20

<210> SEQ ID NO 143
<211> LENGTH: 21
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (16)..(16)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 143

Lys Asp Xaa Xaa Gly Ser Glu Val Asn Leu Asp Asp Glu Phe Gly Xaa
1               5                   10                  15

Pro Lys Asp Asp Tyr
            20

<210> SEQ ID NO 144
<211> LENGTH: 23
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (18)..(18)
<223> OTHER INFORMATION: X is episilon-aminocaproic acid

```
<221> NAME/KEY: MOD_RES
<222> LOCATION: (4)..(4)
<223> OTHER INFORMATION: X is epsilon aminocaproic acid

<400> SEQUENCE: 144

Lys Asp Xaa Xaa Gly Gly Val Val Ile Ala Thr Val Ile Val Ile Thr
1               5                   10                  15

Gly Xaa Pro Lys Asp Asp Tyr
            20

<210> SEQ ID NO 145
<211> LENGTH: 24
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (19)..(19)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 145

Lys Asp Xaa Xaa Gly Tyr Gly Val Val Ile Ala Thr Val Ile Val Ile
1               5                   10                  15

Thr Gly Xaa Pro Lys Asp Asp Tyr
            20

<210> SEQ ID NO 146
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 146

Lys Asp Xaa Xaa Gly Val Ile Ala Thr Val Ile Gly Xaa Pro Lys Asp
1               5                   10                  15

Asp Tyr

<210> SEQ ID NO 147
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 147
```

```
Lys Asp Xaa Xaa Asx Tyr Gly Val Val Ile Ala Gly Xaa Pro Lys Asp
1               5                   10                  15

Asp Tyr
```

<210> SEQ ID NO 148
<211> LENGTH: 15
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(13)
<223> OTHER INFORMATION: X is episilon-aminocaproic acid
<221> NAME/KEY: MOD_RES
<222> LOCATION: (4)..(5)
<223> OTHER INFORMATION: X is epsilon aminocaproic acid

<400> SEQUENCE: 148

```
Lys Asp Xaa Xaa Xaa Gln Gln Leu Leu His Asn Xaa Xaa Pro Lys
1               5                   10                  15
```

<210> SEQ ID NO 149
<211> LENGTH: 15
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 149

```
Lys Asp Xaa Xaa Gly Gln Gln Leu Leu His Asn Gly Xaa Pro Lys
1               5                   10                  15
```

<210> SEQ ID NO 150
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 150

```
Lys Asp Xaa Gly Gln Gln Leu Leu His Asn Gly Pro Lys
1               5                   10
```

<210> SEQ ID NO 151
<211> LENGTH: 11
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 151

```
Lys Asp Xaa Gln Gln Leu Leu His Asn Pro Lys
1               5                   10
```

<210> SEQ ID NO 152
<211> LENGTH: 15
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(13)
<223> OTHER INFORMATION: X is episilon-aminocaproic acid
<221> NAME/KEY: MOD_RES
<222> LOCATION: (4)..(5)
<223> OTHER INFORMATION: X is epsilon aminocaproic acid

<400> SEQUENCE: 152

```
Lys Asp Xaa Xaa Xaa Ser Ile Gln Tyr Thr Tyr Xaa Xaa Pro Lys
1               5                   10                  15
```

<210> SEQ ID NO 153
<211> LENGTH: 15
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 153

```
Lys Asp Xaa Xaa Gly Ser Ile Gln Tyr Thr Tyr Gly Xaa Pro Lys
1               5                   10                  15
```

<210> SEQ ID NO 154
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 154

```
Lys Asp Xaa Gly Ser Ile Gln Tyr Thr Tyr Gly Pro Lys
1               5                   10
```

<210> SEQ ID NO 155
<211> LENGTH: 11
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 155

```
Lys Asp Xaa Ser Ile Gln Tyr Thr Tyr Pro Lys
1               5                   10
```

```
<210> SEQ ID NO 156
<211> LENGTH: 15
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(13)
<223> OTHER INFORMATION: X is episilon-aminocaproic acid
<221> NAME/KEY: MOD_RES
<222> LOCATION: (4)..(5)
<223> OTHER INFORMATION: X is epsilon aminocaproic acid

<400> SEQUENCE: 156

Lys Asp Xaa Xaa Xaa Ser Ser Gln Tyr Ser Asn Xaa Xaa Pro Lys
 1               5                  10                  15

<210> SEQ ID NO 157
<211> LENGTH: 15
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 157

Lys Asp Xaa Xaa Gly Ser Ser Gln Tyr Ser Asn Gly Xaa Pro Lys
 1               5                  10                  15

<210> SEQ ID NO 158
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 158

Lys Asp Xaa Gly Ser Ser Gln Tyr Ser Asn Gly Pro Lys
 1               5                  10

<210> SEQ ID NO 159
<211> LENGTH: 11
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 159

Lys Asp Xaa Ser Ser Gln Tyr Ser Asn Pro Lys
 1               5                  10

<210> SEQ ID NO 160
<211> LENGTH: 15
```

```
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (12)..(13)
<223> OTHER INFORMATION: X is episilon-aminocaproic acid
<221> NAME/KEY: MOD_RES
<222> LOCATION: (4)..(5)
<223> OTHER INFORMATION: X is epsilon aminocaproic acid

<400> SEQUENCE: 160

Lys Asp Xaa Xaa Xaa Ser Ser Ile Tyr Ser Gln Xaa Xaa Pro Lys
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib
<221> NAME/KEY: MOD_RES
<222> LOCATION: (13)..(13)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 161

Lys Asp Xaa Xaa Gly Ser Ser Ile Tyr Ser Gln Gly Xaa Pro Lys
1               5                   10                  15

<210> SEQ ID NO 162
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 162

Lys Asp Xaa Gly Ser Ser Ile Tyr Ser Gln Gly Pro Lys
1               5                   10

<210> SEQ ID NO 163
<211> LENGTH: 11
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (3)..(3)
<223> OTHER INFORMATION: X is Aib

<400> SEQUENCE: 163

Lys Asp Xaa Ser Ser Ile Tyr Ser Gln Pro Lys
1               5                   10

<210> SEQ ID NO 164
<211> LENGTH: 20
<212> TYPE: PRT
<213> ORGANISM: Artificial Sequence
<220> FEATURE:
```

```
<223> OTHER INFORMATION: Synthetic peptide substrate
<221> NAME/KEY: MOD_RES
<222> LOCATION: (4)..(4)
<223> OTHER INFORMATION: X is epsilon aminocaproic acid
<221> NAME/KEY: MOD_RES
<222> LOCATION: (16)..(16)
<223> OTHER INFORMATION: X is episilon-aminocaproic acid
<221> NAME/KEY: MOD_RES
<222> LOCATION: (1)..(1)
<223> OTHER INFORMATION: K is blocked with Fmoc

<400> SEQUENCE: 164

Lys Asp Pro Xaa Gly Ser Glu Val Asn Leu Asp Ala Glu Phe Gly Xaa
1               5                   10                  15

Pro Lys Gly Tyr
            20

<210> SEQ ID NO 165
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 165

Lys Asp Pro Xaa Gly Leu Glu His Asp Gly Ile Asn Gly Xaa Pro Lys
1               5                   10                  15

Gly Tyr

<210> SEQ ID NO 166
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 166

Lys Asp Pro Xaa Gly Leu Glu Thr Asp Gly Ile Asn Gly Xaa Pro Lys
1               5                   10                  15

Gly Tyr

<210> SEQ ID NO 167
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmco
<221> NAME/KEY: MOD_RES
<222> LOCATION: (14)..(14)
```

```
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 167

Lys Asp Pro Xaa Gly Trp Glu His Asp Gly Ile Asn Gly Xaa Pro Lys
1               5                   10                  15

Gly Tyr

<210> SEQ ID NO 168
<211> LENGTH: 15
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (11)..(11)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 168

Lys Asp Pro Xaa Gly Tyr Val His Asp Gly Xaa Pro Lys Gly Tyr
1               5                   10                  15

<210> SEQ ID NO 169
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 169

Lys Asp Pro Xaa Gly Tyr Val His Asp Gly Ile Asn Gly Xaa Pro Lys
1               5                   10                  15

Gly Tyr

<210> SEQ ID NO 170
<211> LENGTH: 18
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is epsilon aminocaproic acid (Ahx)
<221> NAME/KEY: misc_feature
<222> LOCATION: (14)..(14)
<223> OTHER INFORMATION: Xaa is epsilon aminocaproic acid (Ahx)

<400> SEQUENCE: 170

Lys Asp Pro Xaa Gly Tyr Val His Asp Ala Pro Val Gly Xaa Pro Lys
1               5                   10                  15

Gly Tyr
```

<210> SEQ ID NO 171
<211> LENGTH: 18
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is episilon aminocaproic acid (Ahx)
<221> NAME/KEY: misc_feature
<222> LOCATION: (14)..(14)
<223> OTHER INFORMATION: Xaa is episilon aminocaproic acid (Ahx)

<400> SEQUENCE: 171

Lys Asp Pro Xaa Gly Tyr Val His Asp Ala Pro Val Gly Xaa Pro Lys
1               5                   10                  15

Gly Tyr

<210> SEQ ID NO 172
<211> LENGTH: 16
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is episilon aminocaproic acid (Ahx)
<221> NAME/KEY: misc_feature
<222> LOCATION: (12)..(12)
<223> OTHER INFORMATION: Xaa is episilon aminocaproic acid (Ahx)

<400> SEQUENCE: 172

Lys Asp Pro Xaa Val His Asp Ala Pro Val Gly Xaa Pro Lys Gly Tyr
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is episilon aminocaproic acid (Ahx)
<221> NAME/KEY: misc_feature
<222> LOCATION: (12)..(12)
<223> OTHER INFORMATION: Xaa is episilon aminocaproic acid (Ahx)

<400> SEQUENCE: 173

Lys Asp Pro Xaa Gly Tyr Val His Asp Ala Gly Xaa Pro Lys Gly Tyr
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (12)..(12)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 174

Lys Asp Pro Xaa Gly Ile Glu Pro Asp Ser Gly Xaa Pro Lys Gly Tyr

<210> SEQ ID NO 175
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 175

Lys Asp Pro Xaa Gly Pro Leu Gly Ile Ala Gly Ile Gly Xaa Pro Lys
1               5                   10                  15

Gly Tyr

<210> SEQ ID NO 176
<211> LENGTH: 19
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (15)..(15)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 176

Lys Asp Pro Xaa Gly Ser Gln Asn Tyr Pro Ile Val Gln Gly Xaa Pro
1               5                   10                  15

Lys Gly Tyr

<210> SEQ ID NO 177
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fa
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is epsilon aminocaproic acid

<400> SEQUENCE: 177

Lys Asp Pro Xaa Gly Glu Asp Val Val Cys Cys Ser Gly Xaa Pro Lys
1               5                   10                  15

Gly Tyr

<210> SEQ ID NO 178
<211> LENGTH: 10
<212> TYPE: PRT
<213> ORGANISM: Artificial Sequence

```
<220> FEATURE:
<223> OTHER INFORMATION: Peptide spacer

<400> SEQUENCE: 178

Asp Gly Ser Gly Gly Gly Glu Asp Glu Lys
1               5                   10

<210> SEQ ID NO 179
<211> LENGTH: 7
<212> TYPE: PRT
<213> ORGANISM: Artificial Sequence
<220> FEATURE:
<223> OTHER INFORMATION: peptide spacer

<400> SEQUENCE: 179

Lys Glu Asp Gly Gly Asp Lys
1               5

<210> SEQ ID NO 180
<211> LENGTH: 8
<212> TYPE: PRT
<213> ORGANISM: Artificial Sequence
<220> FEATURE:
<223> OTHER INFORMATION: Peptide spacer
<221> NAME/KEY: Artificial
<222> LOCATION: (1)..(8)
<223> OTHER INFORMATION: Spacer

<400> SEQUENCE: 180

Asp Gly Ser Gly Glu Asp Glu Lys
1               5

<210> SEQ ID NO 181
<211> LENGTH: 9
<212> TYPE: PRT
<213> ORGANISM: Artificial Sequence
<220> FEATURE:
<223> OTHER INFORMATION: Peptide spacer
<221> NAME/KEY: Artificial
<222> LOCATION: (1)..(9)
<223> OTHER INFORMATION: Spacer

<400> SEQUENCE: 181

Lys Glu Asp Glu Gly Ser Gly Asp Lys
1               5

<210> SEQ ID NO 182
<211> LENGTH: 8
<212> TYPE: PRT
<213> ORGANISM: Artificial Sequence
<220> FEATURE:
<223> OTHER INFORMATION: protease inhibitor

<400> SEQUENCE: 182

Asp Val Val Cys Cys Ser Met Ser
1               5

<210> SEQ ID NO 183
<211> LENGTH: 7
<212> TYPE: PRT
<213> ORGANISM: Artificial Sequence
<220> FEATURE:
<223> OTHER INFORMATION: protease inhibitor
<221> NAME/KEY: MOD_RES
<222> LOCATION: (6)..(6)
<223> OTHER INFORMATION: d amino acid

<400> SEQUENCE: 183
```

```
Asp Val Val Cys Pro Met Ser
1               5
```

<210> SEQ ID NO 184
<211> LENGTH: 9
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (5)..(5)
<223> OTHER INFORMATION: X is norleucine

<400> SEQUENCE: 184

```
Asp Ala Ile Pro Xaa Ser Ile Pro Cys
1               5
```

<210> SEQ ID NO 185
<211> LENGTH: 11
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (5)..(5)
<223> OTHER INFORMATION: X is norleucine

<400> SEQUENCE: 185

```
Asp Ala Ile Pro Xaa Ser Ile Pro Lys Gly Tyr
1               5                   10
```

<210> SEQ ID NO 186
<211> LENGTH: 11
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: Artificial  = synthetic protease indicator
<221> NAME/KEY: MOD_RES
<222> LOCATION: (9)..(9)
<223> OTHER INFORMATION: K is derivatized with fluorophore
<221> NAME/KEY: MOD_RES
<222> LOCATION: (1)..(1)
<223> OTHER INFORMATION: D is derivatized with fluorophore

<400> SEQUENCE: 186

```
Asp Glu Val Asp Gly Ile Asp Pro Lys Gly Tyr
1               5                   10
```

<210> SEQ ID NO 187
<211> LENGTH: 12
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: Artificial = synthetic protease indicator
<221> NAME/KEY: MOD_RES
<222> LOCATION: (1)..(1)
<223> OTHER INFORMATION: P is derivatized with fluorophore
<221> NAME/KEY: MOD_RES
<222> LOCATION: (10)..(10)
<223> OTHER INFORMATION: K is derivatized with fluorophore

<400> SEQUENCE: 187

```
Pro Asp Glu Val Asp Gly Ile Asp Pro Lys Gly Tyr
1               5                   10
```

<210> SEQ ID NO 188

```
<211> LENGTH: 12
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: Artificial sequence = synthetic protease
      indicator
<221> NAME/KEY: MOD_RES
<222> LOCATION: (6)..(6)
<223> OTHER INFORMATION: X is norleucine (Nlu)
<221> NAME/KEY: MOD_RES
<222> LOCATION: (10)..(10)
<223> OTHER INFORMATION: K is derivatized with fluorophore
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (1)..(1)
<223> OTHER INFORMATION: K is derivatized with fluorophore

<400> SEQUENCE: 188

Lys Asp Ala Ile Pro Xaa Ser Ile Pro Lys Gly Tyr
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: Artificial sequence = synthetic protease
      indicator
<221> NAME/KEY: MOD_RES
<222> LOCATION: (1)..(1)
<223> OTHER INFORMATION: K is derivatized with fluorophore
<221> NAME/KEY: MOD_RES
<222> LOCATION: (10)..(10)
<223> OTHER INFORMATION: K is derivatized with fluorophore
<221> NAME/KEY: MOD_RES
<222> LOCATION: (6)..(6)
<223> OTHER INFORMATION: X is norleucine (Nlu)

<400> SEQUENCE: 189

Lys Asp Ala Ile Pro Xaa Ser Ile Pro Lys Gly Tyr
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: Artificial Sequence = synthetic protease
      indicator
<221> NAME/KEY: MOD_RES
<222> LOCATION: (1)..(1)
<223> OTHER INFORMATION: D is blocked wiht Fmoc
<221> NAME/KEY: MOD_RES
<222> LOCATION: (5)..(5)
<223> OTHER INFORMATION: X is norleucine (Nlu)
<221> NAME/KEY: MOD_RES
<222> LOCATION: (9)..(9)
<223> OTHER INFORMATION: K is derivatized with fluorophore

<400> SEQUENCE: 190

Asp Ala Ile Pro Xaa Ser Ile Pro Lys Gly Tyr
1               5                   10

<210> SEQ ID NO 191
<211> LENGTH: 14
```

```
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: ARTIFICIAL = synthetic protease indicator
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (1)..(1)
<223> OTHER INFORMATION: K is derivatized with fluorophore
<221> NAME/KEY: MOD_RES
<222> LOCATION: (12)..(12)
<223> OTHER INFORMATION: K is derivatized with fluorophore

<400> SEQUENCE: 191

Lys Asp Asx Asp Glu Val Asp Gly Ile Asp Pro Lys Gly Tyr
1               5                   10

<210> SEQ ID NO 192
<211> LENGTH: 14
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: Artificial = synthetic protease
      indicator
<221> NAME/KEY: misc_feature
<222> LOCATION: (1)..(1)
<223> OTHER INFORMATION: K is derivatized with fluorophore
<221> NAME/KEY: misc_feature
<222> LOCATION: (12)..(12)
<223> OTHER INFORMATION: K is derivatized with fluorophore

<400> SEQUENCE: 192

Lys Asp Asx Asp Glu Val Asp Gly Ile Asp Pro Lys Gly Tyr
1               5                   10

<210> SEQ ID NO 193
<211> LENGTH: 14
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: ARTIFICIAL/UNKNOWN = synthetic protease
      indicator
<221> NAME/KEY: MOD_RES
<222> LOCATION: (1)..(1)
<223> OTHER INFORMATION: K is derivatized with fluroophore
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (12)..(12)
<223> OTHER INFORMATION: K is derivatized with fluroophore

<400> SEQUENCE: 193

Lys Asp Asx Asp Glu Val Asn Gly Ile Asp Pro Lys Gly Tyr
1               5                   10

<210> SEQ ID NO 194
<211> LENGTH: 14
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: ARTIFICIAL/UNKNOWN = synthetic protease
      indicator
<221> NAME/KEY: misc_feature
```

```
<222> LOCATION: (1)..(1)
<223> OTHER INFORMATION: K is derivatized with fluorophore
<221> NAME/KEY: misc_feature
<222> LOCATION: (12)..(12)
<223> OTHER INFORMATION: K is derivatized with fluorophore

<400> SEQUENCE: 194

Lys Asp Asx Asp Glu Val Asn Gly Ile Asp Pro Lys Gly Tyr
1               5                   10

<210> SEQ ID NO 195
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: ARTIFICIAL/UNKNOWN = synthetic protease
      indicator
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (11)..(11)
<223> OTHER INFORMATION: K is derivatized with fluorophore

<400> SEQUENCE: 195

Lys Asp Asx Glu Val Asp Gly Ile Asp Pro Lys Gly Tyr
1               5                   10

<210> SEQ ID NO 196
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: ARTIFICIAL/UNKNOWN = synthetic protease
      indicator
<221> NAME/KEY: MOD_RES
<222> LOCATION: (1)..(1)
<223> OTHER INFORMATION: K is derivatized with fluorophore
<221> NAME/KEY: MOD_RES
<222> LOCATION: (11)..(11)
<223> OTHER INFORMATION: K is derivatized with fluorophore

<400> SEQUENCE: 196

Lys Asp Tyr Asx Ala Asp Gly Ile Asp Pro Lys Gly Tyr
1               5                   10

<210> SEQ ID NO 197
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: ARTIFICIAL/UNKNOWN = synthetic protease
      indicator
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (1)..(1)
<223> OTHER INFORMATION: K is derivatized with fluorophore
<221> NAME/KEY: MOD_RES
<222> LOCATION: (14)..(14)
<223> OTHER INFORMATION: K is derivatized with fluorophore

<400> SEQUENCE: 197

Lys Asp Asx Gly Asp Glu Val Asp Gly Ile Asp Gly Pro Lys Gly Tyr
1               5                   10                  15
```

```
<210> SEQ ID NO 198
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: ARTIFICIAL/UNKNOWN = synthetic protease
      indicator
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (1)..(1)
<223> OTHER INFORMATION: K is derivatized with fluorophore
<221> NAME/KEY: MOD_RES
<222> LOCATION: (16)..(16)
<223> OTHER INFORMATION: K is derivatized with fluorophore
<221> NAME/KEY: MOD_RES
<222> LOCATION: (14)..(14)
<223> OTHER INFORMATION: X is episilon aminocaproic acid
<221> NAME/KEY: MOD_RES
<222> LOCATION: (4)..(4)
<223> OTHER INFORMATION: X is episilon aminocaproic acid

<400> SEQUENCE: 198

Lys Asp Asx Xaa Gly Asp Glu Val Asp Gly Ile Asp Gly Xaa Pro Lys
1               5                   10                  15

Gly Tyr

<210> SEQ ID NO 199
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is derivatized with  benzyloxycarbonyl group
<221> NAME/KEY: MOD_RES
<222> LOCATION: (4)..(4)
<223> OTHER INFORMATION: X is episilon aminocaproic acid
<221> NAME/KEY: MOD_RES
<222> LOCATION: (14)..(14)
<223> OTHER INFORMATION: X is episilon aminocaproic acid
<221> NAME/KEY: misc_feature
<223> OTHER INFORMATION: ARTIFICIAL/UNKNOWN = synthetic protease
      indicator
<221> NAME/KEY: MOD_RES
<222> LOCATION: (1)..(1)
<223> OTHER INFORMATION: K is derivatized with  fluorophore
<221> NAME/KEY: MOD_RES
<222> LOCATION: (16)..(16)
<223> OTHER INFORMATION: K is derivatized with  fluorophore

<400> SEQUENCE: 199

Lys Asp Asx Xaa Gly Asp Glu Val Asp Gly Ile Asp Gly Xaa Pro Lys
1               5                   10                  15

Gly Tyr

<210> SEQ ID NO 200
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: ARTIFICIAL/UNKNOWN = synthetic protease
      indicator
<221> NAME/KEY: MOD_RES
<222> LOCATION: (1)..(1)
```

-continued

```
<223> OTHER INFORMATION: K is blocked with Fmoc
<221> NAME/KEY: MOD_RES
<222> LOCATION: (1)..(1)
<223> OTHER INFORMATION: K is derivatized with fluorophore
<221> NAME/KEY: MOD_RES
<222> LOCATION: (11)..(11)
<223> OTHER INFORMATION: K is derivatized with fluorophore

<400> SEQUENCE: 200

Lys Asp Tyr Asx Ala Asp Gly Ile Asp Pro Lys Gly Tyr
1               5                   10

<210> SEQ ID NO 201
<211> LENGTH: 13
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: ARTIFICIAL/UNKNOWN = synthetic protease
      indicator
<221> NAME/KEY: MOD_RES
<222> LOCATION: (1)..(1)
<223> OTHER INFORMATION: K is derivatized with fluorophore
<221> NAME/KEY: MOD_RES
<222> LOCATION: (11)..(11)
<223> OTHER INFORMATION: K is derivatized with fluorophore

<400> SEQUENCE: 201

Lys Asp Asx Glu Val Asp Gly Ile Asp Pro Lys Gly Tyr
1               5                   10

<210> SEQ ID NO 202
<211> LENGTH: 12
<212> TYPE: PRT
<213> ORGANISM: Artificial Sequence
<220> FEATURE:
<223> OTHER INFORMATION: Synthetic peptide substrate
<221> NAME/KEY: misc_feature
<223> OTHER INFORMATION: Artificial/Unknown = synthetic protease
      indicator
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (1)..(1)
<223> OTHER INFORMATION: K is derivatized with fluorophore
<221> NAME/KEY: MOD_RES
<222> LOCATION: (10)..(10)
<223> OTHER INFORMATION: K is derivatized with fluorophore
<221> NAME/KEY: MOD_RES
<222> LOCATION: (6)..(6)
<223> OTHER INFORMATION: X is norleucine (Nlu)

<400> SEQUENCE: 202

Lys Asp Ala Ile Pro Xaa Ser Ile Pro Lys Gly Tyr
1               5                   10

<210> SEQ ID NO 203
<211> LENGTH: 18
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is epsilon-aminocaproic acid
<221> NAME/KEY: misc_feature
<222> LOCATION: (14)..(14)
<223> OTHER INFORMATION: Xaa is epsilon-aminocaproic acid

<400> SEQUENCE: 203
```

```
Lys Asp Pro Xaa Gly Asp Glu Val Asp Gly Ile Asp Gly Xaa Pro Lys
1               5                   10                  15

Gly Tyr

<210> SEQ ID NO 204
<211> LENGTH: 18
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is episilon-aminocaproic acid
<221> NAME/KEY: misc_feature
<222> LOCATION: (14)..(14)
<223> OTHER INFORMATION: Xaa is episilon-aminocaproic acid

<400> SEQUENCE: 204

Lys Asp Pro Xaa Gly Ile Glu Thr Asp Ser Gly Val Gly Xaa Pro Lys
1               5                   10                  15

Gly Tyr

<210> SEQ ID NO 205
<211> LENGTH: 18
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is episilon-aminocaproic acid
<221> NAME/KEY: misc_feature
<222> LOCATION: (14)..(14)
<223> OTHER INFORMATION: Xaa is episilon-aminocaproic acid

<400> SEQUENCE: 205

Lys Asp Pro Xaa Gly Leu Val Glu Ile Asp Asn Gly Gly Xaa Pro Lys
1               5                   10                  15

Gly Tyr

<210> SEQ ID NO 206
<211> LENGTH: 18
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is episilon-aminocaproic acid
<221> NAME/KEY: misc_feature
<222> LOCATION: (14)..(14)
<223> OTHER INFORMATION: Xaa is episilon-aminocaproic acid

<400> SEQUENCE: 206

Lys Asp Pro Xaa Gly Leu Glu His Asp Gly Ile Asn Gly Xaa Pro Lys
1               5                   10                  15

Gly Tyr

<210> SEQ ID NO 207
<211> LENGTH: 18
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is episilon-aminocaproic acid
<221> NAME/KEY: misc_feature
```

```
<222> LOCATION: (14)..(14)
<223> OTHER INFORMATION: Xaa is epsilon-aminocaproic acid

<400> SEQUENCE: 207

Lys Asp Pro Xaa Gly Trp Glu His Asp Gly Ile Asn Gly Xaa Pro Lys
1               5                   10                  15

Gly Tyr

<210> SEQ ID NO 208
<211> LENGTH: 7
<212> TYPE: PRT
<213> ORGANISM: Artificial Sequence
<220> FEATURE:
<223> OTHER INFORMATION: Synthetic peptide substrate

<400> SEQUENCE: 208

Ile Glu Thr Asp Ser Gly Val
1               5

<210> SEQ ID NO 209
<211> LENGTH: 9
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: X is D form of
      tetrahydroisoquinoline-3-carboxylic acid

<400> SEQUENCE: 209

Ser Glu Val Asn Leu Asp Ala Glu Phe
1               5

<210> SEQ ID NO 210
<211> LENGTH: 7
<212> TYPE: PRT
<213> ORGANISM: Artificial Sequence
<220> FEATURE:
<223> OTHER INFORMATION: Synthetic peptide substrate
<221> NAME/KEY: Artificial
<222> LOCATION: (1)..(7)
<223> OTHER INFORMATION: Artificial protease substrate

<400> SEQUENCE: 210

Tyr Val His Asp Ala Pro Val
1               5

<210> SEQ ID NO 211
<211> LENGTH: 4
<212> TYPE: PRT
<213> ORGANISM: Artificial Sequence
<220> FEATURE:
<223> OTHER INFORMATION: domaine of protease indicator

<400> SEQUENCE: 211

Gly Gly Gly Gly
1

<210> SEQ ID NO 212
<211> LENGTH: 18
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
```

```
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (4)..(4)
<223> OTHER INFORMATION: X is episilon-aminocaproic acid

<400> SEQUENCE: 212

Lys Asp Pro Xaa Gly Tyr Val His Asp Ala Pro Val Gly Xaa Pro Lys
1               5                   10                  15

Gly Tyr

<210> SEQ ID NO 213
<211> LENGTH: 15
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (4)..(4)
<223> OTHER INFORMATION: X is episilon-aminocaproic acid
<221> NAME/KEY: MOD_RES
<222> LOCATION: (14)..(14)
<223> OTHER INFORMATION: X is episilon-aminocaproic acid
<221> NAME/KEY: MOD_RES
<222> LOCATION: (15)..(15)
<223> OTHER INFORMATION: K is blocked with amide

<400> SEQUENCE: 213

Lys Asp Pro Xaa Gly Tyr Val His Asp Ala Pro Val Lys Gly Tyr
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Synthetic peptide substrate
<221> NAME/KEY: MOD_RES
<222> LOCATION: (1)..(1)
<223> OTHER INFORMATION: K is blocked with Fmoc
<221> NAME/KEY: MOD_RES
<222> LOCATION: (6)..(6)
<223> OTHER INFORMATION: X is D form tetrahydroisoquinoline-3-carboxylic
    acid
<221> NAME/KEY: MOD_RES
<222> LOCATION: (4)..(4)
<223> OTHER INFORMATION: X is episilon-aminocaproic acid
<221> NAME/KEY: MOD_RES
<222> LOCATION: (15)..(15)
<223> OTHER INFORMATION: X is episilon-aminocaproic acid

<400> SEQUENCE: 214

Lys Asp Pro Tyr Val His Asp Ala Pro Val Gly Lys Pro Lys Gly Tyr
1               5                   10                  15

<210> SEQ ID NO 215
<211> LENGTH: 21
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is episilon-aminocaproic acid
<221> NAME/KEY: misc_feature
<222> LOCATION: (16)..(16)
<223> OTHER INFORMATION: Xaa is episilon-aminocaproic acid
```

```
<400> SEQUENCE: 215

Lys Asp Asx Xaa Gly Ser Glu Val Asn Leu Asp Ala Glu Phe Gly Xaa
1               5                   10                  15

Pro Lys Asp Asp Tyr
            20

<210> SEQ ID NO 216
<211> LENGTH: 7
<212> TYPE: PRT
<213> ORGANISM: Artificial Sequence
<220> FEATURE:
<223> OTHER INFORMATION: Protease indicator

<400> SEQUENCE: 216

Tyr Val His Asp Ala Pro Val
1               5

<210> SEQ ID NO 217
<211> LENGTH: 7
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (1)..(1)
<223> OTHER INFORMATION: Y is "D" form amino acid

<400> SEQUENCE: 217

Tyr Val His Asp Ala Pro Val
1               5

<210> SEQ ID NO 218
<211> LENGTH: 14
<212> TYPE: PRT
<213> ORGANISM: Artificial Sequence
<220> FEATURE:
<223> OTHER INFORMATION: Protease indicator

<400> SEQUENCE: 218

Lys Asp Asx Tyr Val His Asp Ala Pro Val Pro Lys Gly Tyr
1               5                   10

<210> SEQ ID NO 219
<211> LENGTH: 16
<212> TYPE: PRT
<213> ORGANISM: Artificial Sequence
<220> FEATURE:
<223> OTHER INFORMATION: Protease indicator

<400> SEQUENCE: 219

Lys Asp Asx Gly Tyr Val His Asp Ala Pro Val Gly Pro Lys Gly Tyr
1               5                   10                  15

<210> SEQ ID NO 220
<211> LENGTH: 18
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is episilon-aminocaproic acid
<221> NAME/KEY: misc_feature
<222> LOCATION: (14)..(14)
<223> OTHER INFORMATION: Xaa is episilon-aminocaproic acid

<400> SEQUENCE: 220
```

```
-continued

Lys Asp Asx Xaa Gly Tyr Val His Asp Ala Pro Val Gly Xaa Pro Lys
1               5                   10                  15
Gly Tyr

<210> SEQ ID NO 221
<211> LENGTH: 18
<212> TYPE: PRT
<213> ORGANISM: Artificial Sequence
<220> FEATURE:
<223> OTHER INFORMATION: Protease indicator
<221> NAME/KEY: misc_feature
<222> LOCATION: (4)..(4)
<223> OTHER INFORMATION: Xaa is episilon-aminocaproic acid
<221> NAME/KEY: misc_feature
<222> LOCATION: (6)..(6)
<223> OTHER INFORMATION: Y is "D" form amino acid
<221> NAME/KEY: misc_feature
<222> LOCATION: (14)..(14)
<223> OTHER INFORMATION: Xaa is episilon-aminocaproic acid

<400> SEQUENCE: 221

Lys Asp Asx Xaa Gly Tyr Val His Asp Ala Pro Val Gly Xaa Pro Lys
1               5                   10                  15
Gly Tyr
```